United States Patent
Bamford et al.

(10) Patent No.: US 9,765,080 B2
(45) Date of Patent: Sep. 19, 2017

(54) TRIAZOLO[4,5-D] PYRAMIDINE DERIVATIVES AND THEIR USE AS PURINE RECEPTOR ANTAGONISTS

(71) Applicant: Vernalis (R&D) Limited, Winnersh (GB)

(72) Inventors: Samantha Jane Bamford, Winnersh (GB); Roger John Gillespie, Winnersh (GB); Richard Simon Todd, Winnersh (GB)

(73) Assignee: Vernalis (R&D) Limited, Winniersh (GB)

( * ) Notice: Subject to any disclaimer, the term of this patent is extended or adjusted under 35 U.S.C. 154(b) by 0 days.

(21) Appl. No.: 15/172,126

(22) Filed: Jun. 2, 2016

(65) Prior Publication Data

US 2017/0088552 A1    Mar. 30, 2017

Related U.S. Application Data

(60) Continuation of application No. 14/618,829, filed on Feb. 10, 2015, now Pat. No. 9,376,443, which is a continuation of application No. 13/889,921, filed on May 8, 2013, now Pat. No. 8,987,279, which is a division of application No. 12/997,721, filed as application No. PCT/GB2009/001605 on Jun. 25, 2009, now Pat. No. 8,450,328.

(60) Provisional application No. 61/075,538, filed on Jun. 25, 2008.

(30) Foreign Application Priority Data

Apr. 16, 2009 (GB) .................................. 0906579.8

(51) Int. Cl.
| C07D 471/00 | (2006.01) |
| C07D 487/00 | (2006.01) |
| C07D 487/04 | (2006.01) |
| C07D 405/12 | (2006.01) |

(52) U.S. Cl.
CPC ......... *C07D 487/04* (2013.01); *C07D 405/12* (2013.01)

(58) Field of Classification Search
None
See application file for complete search history.

(56) References Cited

U.S. PATENT DOCUMENTS

| 4,739,053 A | 4/1988 | Albert et al. |
| 5,204,353 A | 4/1993 | Meier |
| 5,747,496 A | 5/1998 | Cox et al. |
| 6,107,301 A | 8/2000 | Aldrich et al. |
| 6,124,300 A | 9/2000 | Rajagopalan et al. |
| 6,197,788 B1 | 3/2001 | Fletcher et al. |
| 6,583,156 B1 | 6/2003 | Gillespie et al. |
| 6,608,085 B1 | 8/2003 | Gillespie et al. |
| 6,787,541 B1 | 9/2004 | Gillespie et al. |
| 7,141,575 B2 | 11/2006 | Gillespie et al. |
| 7,405,219 B2 | 7/2008 | Gillespie et al. |
| 7,589,097 B2 | 9/2009 | Gillespie et al. |
| 8,450,328 B2 | 5/2013 | Bamford et al. |

FOREIGN PATENT DOCUMENTS

| EP | 1 221 444 A1 | 7/2002 |
| EP | 1 300 147 A1 | 4/2003 |
| JP | 56/131586 | 10/1981 |
| JP | 56/131587 | 10/1981 |
| JP | 59/062595 | 4/1984 |
| JP | 60/140335 | 7/1985 |
| WO | WO 98/08847 | 3/1998 |
| WO | WO 99/01439 A | 1/1999 |
| WO | WO 99/21617 A | 5/1999 |
| WO | WO 02/055083 A1 | 7/2002 |

OTHER PUBLICATIONS

Albert et al., v-Triazolo[4,5-d]pyrimidines (8-Azapurines , Part IX, J. Chem. Soc. (Perkin Trans 1), 1972, pp. 457-461, 4.
Albert et al., v-Triazolo[4,5-d]pyrimidines (8-Azapurines , Part XIV, J. Chem. Soc. (Perkin Trans 1), 1973, pp. 2037-2041, 19.
Albert et al., v-Triazolo[4,5-d]pyrimidines (8-Azapurines), Part XVI, J. Chem. Soc. (Perkin Trans 1), 1975, pp. 345-349, 4.
Albert et al., J. Chem. Soc. (Perkin Trans 1), 1977, pp. 1819-1822, 16.
Albert et al., v-Triazolo[4,5-d]pyrimidines (8-Azapurines , Part 22, J. Chem. Soc. (Perkin Trans 1), 1980, pp. 2918-2922, 12.
Author Unknown, Developments in the Treatment of Parkinson's Disease, *Drug and Therapeutic Bulletin*, No. 35, pp. 36-40 (1999).
Bailey et al., "Changes in spinal δ- and κ-opioid systems in mice deficient in the A2A receptor gene", *Journal of Neuroscience*, vol. 22, No. 21, 2002 (pp. 9210-9220). [Abstract Only].

(Continued)

*Primary Examiner* — Jeffrey H Murray
(74) *Attorney, Agent, or Firm* — Foley & Lardner LLP

(57) ABSTRACT

Compounds of formula (I) that are capable of acting as purine receptor antagonists, pharmaceutical compositions including the compounds, and methods of making the compounds, are. disclosed. The compounds and compositions can be used in treating or preventing disorders related to purine receptor hyperfunctioning.

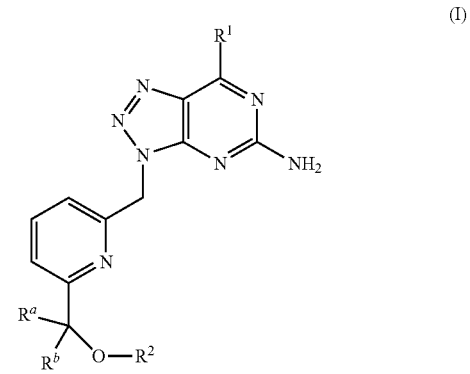

4 Claims, No Drawings

(56) References Cited

OTHER PUBLICATIONS

Bakavoli, et al., Synthesis of 4,4-bis-pyrimidines and some related bis-fused pyrimidines, J. Sci. Islamic Repub. Iran, 1995, pp. 158-162, 6(3) (Abstract).
Baker et al., Irreversibel Enzyme Inhibitors 98, J. Pharm. Sci., 1967, pp. 1075-1081, 56(9).
Banker et al., "Modern Pharmaceutics," pp. 451 and 596 (1996).
Bara-Jimenez et al., "Adenosine A2A receptor antagonist treatment of Parkinson's disease", Neurology, vol. 61, No. 3, 2003 (pp. 293-296) [Abstract Only].
Bastia et al., "Effects of $A_1$ and $A_{2A}$ adenosine receptor ligands in mouse acute models of pain", Neuroscience Letters 328, 2002 (pp. 241-244).
Behan et al., "Enhanced, neuronal damage by co-administration of quinolinic acid and free radicals, and protection by adenosine $A_{2A}$ receptor antagonists", British Hournal of Pharmacology, vol. 135, 2002 (pp. 1435-1442).
Bertorelli et al., "Effects of Selective Agonists and Antagonists for $A_1$ or $A_{2A}$ Adenosine Receptors on Sleep-Waking Patterns in Rats", Drug Development Research, vol. 37, 1996 (pp. 65-72).
Bibbiani et al., "A2A Antagonist Prevents Dopamine Agonist-Induced Motor Complications in Animal Models of Parkinson's Disease," Exper. Neurology, vol. 184, pp. 285-294 (2003).
Carter et al., "Characterization of Progressive Motor Deficits in Miche Transgenic for the Human Huntington's Disease Mutation," The Journ. of Neuroscience, vol. 19, No. 8, pp. 3248-3257 (1999).
Chase et al., "Translating $A_{2A}$ antagonist KW6002 from animal models to parkinsonian patients", Neurology, vol. 61, (11, Suppl. 6), (pp. S107-S111), (2003) [Abstract Only].
Chorvat, et al., Synthesis, Corticotropin-Releasing Factor Receptor Binding Affinity, and Pharmacokinetic Properties of Triazolo-Imidazo-, and Pyrrolopyrimidines and pyridines, J. Med. Chem., 1999, pp. 833-848, 42.
Dall'Lgna et al., "Neuroprotection by caffeine and adenosine $A_{2A}$ receptor blockade of β-amyloid neurotoxicity", British Journal of Pharmacology, vol. 138, 2003 (pp. 1207-1209).
El Yacoubi et al., "Adenosine $A_{2A}$ receptor antagonists are potential antidepressants: evidence based on pharmacology and $A_{2A}$ receptor knockout mice", British Journal of Pharmacology, vol. 134, No. 1, 2001. (pp. 68-77).
Fredholm, et al "Actions of Caffeine in the Brain with Special References to Factors That Contribute to Its widespread Use", Pharmacological Reviews, vol. 51, No. 1, 1999 (pp. 83-133).
Garfinkel, et al., "Responses to Methylphenidate and Varied Doses of Caffeine in Children with Attention Deficit Disorder", Can. J. Psychiatry, vol. 26, No. 6, Oct. 1981 (pp. 395-401).
González-Benítez et al., "Regulation of glycogen metabolism in hepatocytes through adenosine receptors. Role of $Ca^{2+}$ and cAMP", European Journal of Pharmacology, vol. 437, 2002 (pp. 105-111).
Gordeev et al., SSSR Ser. Khim, 1990, pp. 1392-1397, 6 (Russian language document ; English language abstract supplied).
Hauser et al., "Randomized trial of the adenosine A2A receptor antagonist istradefylline in advanced PD", Neurology, vol. 61, No. 3, 2003 (pp. 297-303). [Abstract Only].
Hellier et al., "Assessment of Inhibition and Epileptiform Activity in the Septal Dentate Gyrus of Freely Behaving Rats During the First Week After Kainate Treatment," The Journ. of Neuroscience, vol. 19, No. 22, pp. 10053-10064 (1999).
Hess, "Recent advances in adenosine receptor antagonist research", Review, Monthly Focus: Central and Peripheral Nervous Systems, 2001 (pp. 1533-1561).
Higashino et al., The Photochem Ical Transformation of 3-phenyl-3H-1, 2, 3-triazolo[4,5-d]pyrimidines into 9H-pyrimido[4,5-b]Indoles, Heterocycles, 1981, pp. 483-487, 15(1).
Higashino et al., Yakugaku Zasshi, 1979, pp. 1031-1036, 99(10) (Abstract).
Higashino, et al., On 3-Methyl- and 3-Phenyl-3H-1,2,3-triazolo[4,5-d]pyrimidines, >> Chem. Pharm. Bull, 1979, pp. 2431-2436, 27(10).
Higashino, et al., The Grignard Reaction of 3-Substituted 3H-1,2,3-Triazolo[4,5-d]pyrimidines, Chem. Pharm. Bull, 1979, pp. 3176-3179, 27(12).
Higashino, et al., Triazolo[4,5-d]pyrimidines. VI. 3-Phenyl-3H-1,2,3-triazolo[4,5-d]-pyrimidine-7-carbonitrile and Related Compounds, Chem. Pharm. Bull, 1980, pp. 255-261, 28(1).
Higashino, et al., The Nucleophilic Sustitution of 7-chloro- and 7-(p-Tolylsulfonyl)-3-phenyl-3H-1,2,3-triazolo[4,5-d]pyrimidines, Chem. Pharm, Bull, 1980, pp. 337-343, 28(1).
Higashino, et al., Triazolo[4,5-dpyrimidines. VIII. Aryl Migration of 7-Aroyl-3H-1,2,3-triazolo[4,5-d]pyrimidines to 7-Aryl-3H-1,2,3-triazolo[4,5-d]pyrimidines, Chem. Pharm. Bull, 1985, pp. 1395-1399, 33(4).
Higashino, et al., Reactions of the Anion of Quinazoine Reissert Compound (3-Benzoyl-3,4-dihydro-4-quinazolinecarbonitrile) with Electrophiles, Chem. Pharm. Bull, 1985, pp. 950-961, 33(3).
Higashino, et al., Studies of Pyrazolo[3,4-d]pyrimidine Derivatives. XVI. Preparation of Reissert Compounds from Condensed Pyrimidine Systems, Chem. Pharm. Bull, 1987, pp. 4803-4812, 35(12).
Higashino, et al., Fukusokan Kagaku Toronkai Koen Yoshishu, 12th, 1979, 171-5 (Japanese Language Conference Report ; English language abstract supplied).
Ikeda et al., "Neuroprotection by adenosine $A_{2A}$ receptor blockade in experimental models of Parkinson's disease", Journal of Neurochemistry, vol. 80, No. 2, Jan. 2002 (pp. 262-270).
Jenner et al., "Istradefylline, a Novel Adenosinde A2A Receptor Antagonist, for the Treatment of Parkinson's Disease," Expert. Opin. Investig. Drugs, vol. 14, No. 6, pp. 729-738 (2005).
Kase, "New aspects of physiological and pathophsiological function of adenosine A2A receptor in basal ganglia", Biochemistry, vol. 65, No. 7, 2001 (pp. 1447-1457). [Abstract Only].
Konitsiotis, "Novel pharmacological strategies for motor complications in Parkinson's Disease," Expert. Opin. Investig. Drugs, vol. 14, pp. 377-392 (2005).
Kulisevsky et al., "A Double-Blind Crossover, Placebo-Controlled Study of the Adenosine A2A Antagonist Theophylline in Parkinson's Disease," Clinical Neuropharmacology, vol. 25, No. 1, pp. 25-31 (2001) [Abstract Only].
Kopf et al., "Adenosine and memory storage: effect of $A_1$ and $A_2$ receptor antagonists", Psychopharmacology, vol. 146, No. 2, Sep. 11, 1999 (pp. 214-219).
Ledent et al., "Aggressiveness, hypoalgesia and high blood pressure in mice lacking the adenosine A2a receptor", Nature, vol. 388(6643), Aug. 14, 1997 (pp. 674-678). [Abstract Only].
LeWitt, "New Drugs for the Treatment of Parkinson's Disease," Pharmacotherapy, pp. 26S-32S, (2000).
Li et al., "Differing Roles of Adenosine Receptor Subtypes in Retinal Ischemia-Reperfusion Injury in the Rat", Exp. Eye Res., vol. 68, 1999 (pp. 9-17).
Loscher, "Animal models of epilepsy for the development of antiepileptogenic and disease-modifying drugs. A comparison of the pharmacology of kindling and post-status epilepticus models of temporal lobe epilepsy," Epilepsy Research, vol. 50, pp. 105-123 (2002).
Mally et al., "Potential of Adenosine $A_{2A}$ Receptor Antagonists in the Treatment of Movement Disorders", CNS Drugs, vol. 10, No. 5, Nov. 1998 (pp. 311-320).
Miyashita, et al., Ring Transformation of Condensed Pyrimidines by Enamines and Ynamines. Formation of Condensed Pyridines and Condences Diazocines, Chem. Pharm. Bull, 1991, pp. 282-287, 39(2).
Miyashita et al., Catalytic Action of Azolium Salts.IX. Synthesis of 6-Aroyl-9H-purines and Their Analogues by Nucleophilic Aroylation Catalyzed by Imidazolium or Benzimidazolium Salt, Chem. Pharm. Bull, 1998, pp. 390-399, 46(3).
Miyashita, et al., Preparation of Heteroarenecarbonitriles by Reaction of Haloheteroarenes with Potassium Cyanide Catalyzed by Sodium p-Toluenesulfinate, Heterocycles, 1994, pp. 345-356, 39(1).
Miyashita, et al., Ring opening of 4-chloroquinazoline into 2-arylmethyleneaminobenzonitrile by grignard reaction, Heterocycles, 1994, pp. 823-831, 37(2).

(56) References Cited

OTHER PUBLICATIONS

Miyashita, et al., Carbon-Carbon Bond Cleavage of )α-hydroxybenzyl Heterocycles to ketones and heteroarenes by catalytic action of cyanide ion based on retro-benzoin condensation, 1997, pp. 1-5, 45(1).
Miyashita, et al., Synthesis and Reactivities of 1,3-dimethyl-2)(α-hydroxybenzyl) Imidazolium and 1,3-dimethyl-2-Heterocycles )(α-hydroxybenzyl), benzimidazolium Iodides, 1997, pp. 417-426, 44.
Miyashita, et al., Several Approaches to Cyanide Ion-Catalyzed Synthesis of 4-aroyl-1-phenyl-1H-Pyrazolo[3,4-d]pyrimidines, Heterocycles, 1998, pp. 407-414, 47(1).
Molina et al., Fused Pyrimidines by a Tandem Aza-Wittig/Electrocyclic Ring Closure Strategy, J. Org. Chem., 1988, pp. 4654-4663, 53(20).
Molina et al., Tandem AZA-Wittig Reaction/Electrocyclic Ring-Closure a Facile Entry to the Synthesis of Fused Pyrimidines, Tetrahedron Lett., 1987, pp. 4451-4454, 28(38).
Monopoli et al., "Blockade of adenosine $A_{2A}$ receptors by SCH 58261 results in neuroprotective effects in cerebral ischaemia in rats", Neuropharmacology, vol. 9, No. 17, Dec. 1, 1998 (pp. 3955-3959).
Monopoli et al., "Cardiovascular Pharmacology of the $A_{2A}$ Adenosine Receptor Antagonist, SCH 58261, in the Rat", The Journal of Pharmacology and Experimental Therapeutics, vol. 285, No. 1, 1998.
Morelli, "Adenosine A2A Antagonist: potential preventive and palliative treatment for Parkinson's Disease," Experimental Neurology, No. 184, pp. 20-23 (2003).
Ongini et al., "Dual Actions of $A_{2A}$ Adenosine Receptor Antagonists on Motor Dysfunction and Neurodegenerative Processes", Drug Development Research, vol. 52, No. ½, 2001 (pp. 379-386).
Osborne et al., "Optic Nerve and Neuroprotection Strategies," Eye, vol. 18, pp. 1075-1084 (2004).
Popoli et al., "Blockade of Striatal Adenosine $A_{2A}$ Receptor Reduces, through a Presynaptic Mechanism, Quinolinic Acid-Induced Excitotoxicity: Possible Relevance to Neuroprotective Interventions in Neurodegenerative Diseases of the Striatum", The Journal of Neuroscience, vol. 22, No. 5, Mar. 1, 2002 (pp. 1967-1975).
Satoh et al., "Involvement of adenosine $A_{2A}$ receptor in sleep promotion", European Journal of Pharmacology, vol. 351, 1998 (pp. 155-162).
Scammell et al., "An Adenosine A2a Agonist Increases Sleep and Induces FOS in Ventrolateral Preoptic Neurons", Neuroscience, vol. 107 No. 4, 2001 (pp. 653-663).
Schechter, M.D. et al., "Objectively Measured Hyperactivity—II. Caffeine and Amphetamine Effects", J. Clin. Pharmacol., vol. 25, 1985 (pp. 276-280).
Stone et al., "Neuroprotection by $A_{2A}$ Receptor Antagonists", Drug Development Research, vol. 52 No. ½, 2001 (pp. 323-330).
Suzuki, et al., Carbon-Carbon Bond Cleavage of α-hydroxybenzylheteroarenes Catalyzed by Cyanide Ion : Retro-Benzoin Condensation Affords Ketones and Heteroareness and Benzyl Migration Affords Benzylheteroarenes and Arenecarbaldehydes, Chem. Pharm. Bull, 1998, pp. 199-206, 46(2).
Svenningsson, P. et al., "Distribution, Biochemistry and Function of Striatal Adenosine $A_{2A}$ Receptors", Progress in Neurobiology, vol. 59, 1999 (pp. 355-396).
Tanji, et al., Reactions of 5-Chloro-and 5-(Methylsulfonyl)-3-phenyl-3H-1,2,3-triazolo[4,5-d]pyrimidines with C-Nucleophiles, Chem. Pharm. Bull, 1989, pp. 1731-1734, 37(7).
Tanji, et al., Halogen-Metal Exchange Reaction of 7-Halo-3-phenyl-3H-1,2,3-triazolo[4,5-d]pyrimidines with Butyllithium, Chem. Pharm. Bull, 1991, pp. 2793-2796, 39(11).
Tanji, et al., Halogen-Metal Exchange Reaction of 5-Halo-3H-1,2,3-triazolo-[4,5-d]pyrimidines with Butyllithium, Chem. Pharm. Bull, 1991, pp. 3037-3040, 39(11).
Tanji, Reactions of 6-Benzoyl-6, 7-dehydro-3-phenyl-3H-1,2,3-triazolo-[4,5-d]pyrimidines (Triazolopyrimidine Reissert Compounds) with Acid, Base, and Electrophile, et al., Chem. Pharm. Bull, 1992, pp. 513-517, 40(2).
Tuite et al., Recent Developments in the Pharmacological Treatment of Parkinson's Disease, Expert. Opin. Investig. Drugs, vol. 12, pp. 1335-1352 (2003).
Urade et al., "Sleep regulation in adenosine $A_{2A}$ receptor-deficient mice", Neurology, vol. 61(11, Suppl. 6), (pp. S94-S96). [Abstract Only).
Varani et al., "Aberrant $A_{2A}$ receptor function in peripheral blood cells in Huntington's disease", FASEB Journal, vol. 17, No. 14, 2003 (pp. 2148-2150). [Abstract Only].
Varani et al., "Adenosine $A_{2A}$ Antagonists and Huntington's disease", Colloque Scientifique sur le Café, 2001, $19^{th}$ (pp. 51-58).
Vippagunta et al., Advanced Drug Delivery Reviews 48, pp. 3-26 (2001).
Wenning et al., "Neural Transplantation in animal models of multiple system atrophy : A Review," J. Neural. Transm. Suppl., vol. 55, pp. 103-113 (1999).
Wolff et al., "Burger's Medicinal Chemistry and Drug Discovery," pp. 975-977 (1995).
Yanamoto et al., "Evaluation of MCAO Stroke Models in Normotensive Rats : Standardized Neocortical Infarction by the 3VO Technique," Exp. Neurol., vol. 182, No. 2, pp. 261-274 (2003).
Yacoubi et al., "Adenosine A2A receptor antagonists are potential antidepressants : evidence based on pharmacology and A2A receptor knockout mice," British Journ. of Pharmacology, vol. 134, pp. 68-77 (2001).
Wusong et al., "Adenosine and Receptor Thereof and Brain Injury," Foreign Medical Sciences, Section of Physiology and Pathology, vol. 18, No. 1, pp. 55-58 (1998).
International Search Report cited in related International Patent Application No. PCT/GB2009/001605, completed Aug. 24, 2009.
Written Opinion cited in related International Patent Application No. PCT/GB2009/001605, completed Aug. 24, 2009.

TRIAZOLO[4,5-D] PYRAMIDINE DERIVATIVES AND THEIR USE AS PURINE RECEPTOR ANTAGONISTS

This application is a continuation of U.S. patent application Ser. No. 14/618,829, filed Feb. 10, 2015, which is a continuation of U.S. patent application Ser. No. 13/889,921, filed May 8, 2013, now U.S. Pat. No. 8,987,279, which is a divisional of U.S. patent application Ser. No. 12/997,721, filed Mar. 31, 2011, now U.S. Pat. No. 8,450,328, which is the National Phase of International Patent Application No. PCT/GB2009/001605, filed Jun. 25, 2009, which claims priority from U.S. Provisional Patent Application No. 61/075,538, filed Jun. 25, 2008, and Great Britain Patent Application No. 0906579.8, filed Apr. 16, 2009. The contents of these applications are incorporated herein by reference in their entirety.

TECHNICAL FIELD

The present invention relates to pharmaceutical compositions and methods, and methods of making and using the same.

BACKGROUND TO THE INVENTION

Movement disorders constitute a serious health problem, especially among the elderly. These movement disorders can often be the result of brain lesions. Disorders involving the basal ganglia which result in movement disorders include Parkinson's disease, Huntington's chorea and Wilson's disease. Furthermore, dyskinesias often arise as sequelae of cerebral ischaemia and other neurological disorders.

There are four classic symptoms of Parkinson's disease: tremor, rigidity, akinesia and postural changes. The disease is also commonly associated with depression, dementia and overall cognitive decline. Parkinson's disease has a prevalence of 1 per 1,000 of the total population. The incidence increases to 1 per 100 for those aged over 60 years. Degeneration of dopaminergic neurons in the substantia nigra and the subsequent reductions in interstitial concentrations of dopamine in the striatum are critical to the development of Parkinson's disease. Some 80% of cells from the substantia nigra can be destroyed before the clinical symptoms of Parkinson's disease become apparent.

Some strategies for the treatment of Parkinson's disease are based on transmitter replacement therapy (L-dihydroxyphenylacetic acid (L-DOPA)), inhibition of monoamine oxidase (e.g., Deprenyl™), dopamine receptor agonists (e.g., bromocriptine and apomorphine) and anticholinergics (e.g., benztrophine, orphenadrine). Transmitter replacement therapy may not provide consistent clinical benefit, especially after prolonged treatment when "on-off" symptoms develop. Furthermore, such treatments have also been associated with involuntary movements of athetosis and chorea, nausea and vomiting. Additionally, current therapies do not treat the underlying neurodegenerative disorder resulting in a continuing cognitive decline in patients.

Blockade of $A_2$ adenosine receptors has been implicated in the treatment of movement disorders such as Parkinson's disease, Restless legs syndrome, nocturnal myoclonus and in the treatment of cerebral ischemia. See, for example, WO 02/055083; Richardson, P. J. et al., *Trends Pharmacol. Sci.* 1997, 18, 338-344; and Gao, Y. and Phillis, J. W., *Life Sci.* 1994, 55, 61-65, each of which is incorporated by reference in its entirety. Adenosine $A_{2A}$ receptor antagonists have potential use in the treatment of movement disorders such as Parkinson's Disease (Mally, J. and Stone, T. W., *CNS Drugs*, 1998, 10, 311-320, which is incorporated by reference in its entirety).

Adenosine is a naturally occurring purine nucleoside which has a wide variety of well-documented regulatory functions and physiological effects. The central nervous system (CNS) effects of this endogenous nucleoside have attracted particular attention in drug discovery, because of the therapeutic potential of purinergic agents in CNS disorders (Jacobson, K. A. et al., *J. Med. Chem* 1992, 35, 407-422, and Bhagwhat, S. S.; Williams, M. E. *Opin. Ther. Patents* 1995, 5, 547-558, each which is incorporated by reference in its entirety).

Adenosine receptors represent a subclass ($P_1$) of the group of purine nucleotide and nucleoside receptors known as purinoreceptors. The main pharmacologically distinct adenosine receptor subtypes are known as $A_1$, $A_{2A}$, $A_{2B}$ (of high and low affinity) and $A_3$ (Fredholm, B. B., et al., *Pharmacol. Rev.* 1994, 46, 143-156, which is incorporated by reference in its entirety). The adenosine receptors are present in the CNS (Fredholm, B. B., *News Physiol. Sci.*, 1995, 10, 122-128, which is incorporated by reference in its entirety).

$P_1$ receptor-mediated agents can be useful in the treatment of cerebral ischemia or neurodegenerative disorders, such as Parkinson's disease (Jacobson, K. A., Suzuki, F., *Drug Dev. Res.*, 1997, 39, 289-300; Baraldi, P. G. et al., *Curr. Med. Chem.* 1995, 2, 707-722; and Williams, M. and Bumnstock, G. *Purinergic Approaches Exp. Ther.* (1997), 3-26. Editor. Jacobson, Kenneth A.; Jarvis, Michael F. Publisher: Wileyliss, New York, N.Y., which is incorporated by reference in its entirety).

It has been speculated that xanthine derivatives such as caffeine may offer a form of treatment for attention-deficit hyperactivity disorder (ADHD). A number of studies have demonstrated a beneficial effect of caffeine on controlling the symptoms of ADHD (Garfinkel, B. D. et al., *Psychiatry*, 1981, 26, 395-401, which is incorporated by reference in its entirety). Antagonism of adenosine receptors is thought to account for the majority of the behavioral effects of caffeine in humans and thus blockade of adenosine $A_{2A}$ receptors may account for the observed effects of caffeine in ADHD patients. Therefore a selective adenosine $A_{2A}$ receptor antagonist may provide an effective treatment for ADHD but with decreased side-effects.

Adenosine receptors can play an important role in regulation of sleep patterns, and indeed adenosine antagonists such as caffeine exert potent stimulant effects and can be used to prolong wakefulness (Porkka-Heiskanen, T. et al., *Science*, 1997, 276, 1265-1268, which is incorporated by reference in its entirety). Adenosine's sleep regulation can be mediated by the adenosine $A_{2A}$ receptor (Satoh, S., et al., *Proc. Natl. Acad. Sci., USA,* 1996, 93: 5980-5984, which is incorporated by reference in its entirety). Thus, a selective adenosine $A_{2A}$ receptor antagonist may be of benefit in counteracting excessive sleepiness in sleep disorders such as hypersomnia or narcolepsy.

Patients with major depression demonstrate a blunted response to adenosine agonist-induced stimulation in platelets, suggesting that a dysregulation of adenosine $A_{2A}$ receptor function may occur during depression (Berk, M. et al., 2001, *Eur. Neuropsycophannacol.* 11, 183-186, which is incorporated by reference in its entirety). Experimental evidence in animal models has shown that blockade of adenosine $A_{2A}$ receptor function confers antidepressant activity (El Yacoubi, M et al., *Br. J. Pharmacol.* 2001, 134, 68-77, which is incorporated by reference in its entirety).

Thus, adenosine $A_{2A}$ receptor antagonists may be useful in treatment of major depression and other affective disorders in patients.

The pharmacology of adenosine $A_{2A}$ receptors has been reviewed (Ongini, E.; Fredholm, B. B. *Trends Pharmacol. Sci.* 1996, 17(10), 364-372, which is incorporated by reference in its entirety). One possible mechanism in the treatment of movement disorders by adenosine $A_{2A}$ antagonists is that $A_{2A}$ receptors may be functionally linked dopamine $D_2$ receptors in the CNS. See, for example, Ferre, S. et al., *Proc. Natl. Acad. Sci. USA* 1991, 88, 7238-7241; Puxe, K. et al., *Adenosine Adenine Nucleotides Mol. Biol. Integr. Physiol.*, (*Proc. Int. Symp.*), 5th (1995), 499-507. Editors: Belardinelr, Luiz; Pelleg, Amir. Publisher: Kluwer, Boston, Mass.; and Ferre, S. et al., *Trends Neurosci.* 1997, 20, 482-487, each of which is incorporated by reference in its entirety.

Interest in the role of adenosine $A_{2A}$ receptors in the CNS, due in part to in vivo studies linking $A_{2A}$ receptors with catalepsy (Ferre et al., *Neurosci. Lett.* 1991, 130, 1624; and Mandhane, S. N. et al., *Eur. J. Pharmacol.* 1997, 328, 135-141, each of which is incorporated by reference in its entirety), has prompted investigations into agents that selectively bind to adenosine $A_{2A}$ receptors.

One advantage of adenosine $A_{2A}$ antagonist therapy is that the underlying neurodegenerative disorder may also be treated. See, e.g., Ongini, E.; Adami, M.; Ferri, C.; Bertorelli, R., *Ann. N.Y. Acad. Sci.* 1997, 825 (Neuroprotective Agents), 3048, which is incorporated by reference in its entirety. In particular, blockade of adenosine $A_{2A}$ receptor function confers neuroprotection against MPTP-induced neurotoxicity in mice (Chen, J-F., *J. Neurosci.* 2001, 21, RC143, which is incorporated by reference in its entirety). In addition, consumption of dietary caffeine (a known adenosine $A_{2A}$ receptor antagonist), is associated with a reduced risk of Parkinson's disease (Ascherio, A. et al, *Ann. Neurot.*, 2001, 50, 56-63; and Ross G. W., et al., *JAMA*, 2000, 283, 2674-9, each of which is incorporated by reference in its entirety). Thus, adenosine $A_{2A}$ receptor antagonists may confer neuroprotection in neurodegenerative diseases such as Parkinson's disease.

Xanthine derivatives have been disclosed as adenosine $A_{2A}$ receptor antagonists for treating various diseases caused by hyperfunctioning of adenosine $A_2$ receptors, such as Parkinson's disease (see, for example, EP-A-565377, which is incorporated by reference in its entirety). One prominent xanthine-derived adenosine $A_{2A}$ selective antagonist is CSC [8-(3-chlorostyryl)caffeine] (Jacobson et al., *FEBS Lett.*, 1993, 323, 141-144, which is incorporated by reference in its entirety).

Theophylline (1,3-dimethylxanthine), a bronchodilator drug which is a mixed antagonist at adenosine $A_1$ and $A_{2A}$ receptors, has been studied clinically. To determine whether a formulation of this adenosine receptor antagonist would be of value in Parkinson's disease an open trial was conducted on 15 Parkinsonian patients, treated for up to 12 weeks with a slow release oral theophylline preparation (150 mg/day), yielding serum theophylline levels of 4.44 mg/L after one week. The patients exhibited significant improvements in mean objective disability scores and 11 reported moderate or marked subjective improvement (Mally, J., Stone, T. W. *J. Pharm. Pharmacol.* 1994, 46, 515-517, which is incorporated by reference in its entirety).

KF 17837 (E-8-(3,4dimethoxystyryl)-1,3-dipropyl-7-methylxanthine) is a selective adenosine $A_{2A}$ receptor antagonist which on oral administration significantly ameliorated the cataleptic responses induced by intracerebroventricular administration of an adenosine $A_{2A}$ receptor agonist, CGS 21680. KF 17837 also reduced the catalepsy induced by haloperidol and reserpine. Moreover, KF 17837 potentiated the anticataleptic effects of a subthreshold dose of L-DOPA plus benserazide, suggesting that KF 17837 is a centrally active adenosine $A_{2A}$ receptor antagonist and that the dopaminergic function of the nigrostriatal pathway is potentiated by adenosine $A_{2A}$ receptor antagonists (Kanda, T. et al., *Eur. J. Pharmacol.* 1994, 256, 263-268, which is incorporated by reference in its entirety). The structure activity relationship (SAR) of KF 17837 has been published (Shimada, J. et al., *Bioorg. Med. Chem. Lett.* 1997, 7, 2349-2352, which is incorporated by reference in its entirety). Recent data has also been provided on the adenosine $A_{2A}$ receptor antagonist KW-6002 (Kuwana, Y et al., Soc. *Neurosci. Abstr.* 1997, 23, 119.14; and Kanda, T. et al., *Ann. Neurol.* 1998, 43(4), 507-513, each of which is incorporated by reference in its entirety).

Non-xanthine structures sharing these pharmacological properties include SCH 58261 and its derivatives (Baraldi, P. G. et al., *J. Med Chem.* 1996, 39, 1164-71, which is incorporated by reference in its entirety). SCH 58261 (7-(2-phenylethyl)-5-amino-2-(2-furyl)-pyrazolo-[4,3-e]-1,2,4triazolo[1,5-c]pyrimidine) is reported as effective in the treatment of movement disorders (Ongini, E. *Drug Dev. Res.* 1997, 42(2), 63-70, which is incorporated by reference in its entirety) and has been followed up by a later series of compounds (Baraldi, P. G. et al., *J. Med. Chem.* 1998, 41(12), 2126-2133, which is incorporated by reference in its entirety).

Accordingly, blocking of purine receptors, particularly adenosine receptors, and more particularly adenosine $A_{2A}$ receptors may be beneficial in treatment or prevention of movement disorders such as Parkinson's disease, Restless leg syndrome and nocturnal myoclonus, or disorders such as depression, cognitive, or memory impairment, acute and chronic pain, ADHD or narcolepsy, or for neuroprotection in a subject.

A number of adenosine $A_{2A}$ antagonists are described in International Patent Application Publication WO 02/055083 A1, which is incorporated by reference in its entirety.

DESCRIPTION OF THE INVENTION

The compounds of the present invention are selective adenosine $A_{2A}$ antagonists. Thus, they have particular affinity for the adenosine $A_{2A}$ receptor and demonstrate selectivity for this receptor over the other types of adenosine receptors ($A_1$, $A_{2B}$, $A_3$). Significantly, the compounds of the present invention show greater selectivity for the adenosine $A_{2A}$ receptor than for the adenosine $A_{2B}$ receptor when compared to known adenosine $A_{2A}$ receptor antagonists. Selectivity over the adenosine $A_{2B}$ receptor is advantageous for the reasons discussed below.

The adenosine $A_{2B}$ receptor is highly abundant in bone marrow macrophages and vascular smooth muscle. $A_{2B}$ receptor knockout studies have demonstrated that removal of the $A_{2B}$ receptor in mice produces a higher level of vascular injury following femoral artery injury than seen in wild-type mice, the signal for which originates from bone marrow cells (Yang et al., 2008). Vascular injury represents a critical initiating event in the pathogenesis of various vascular diseases, including atherosclerosis, restenosis and sepsis. It is therefore likely that sustained antagonism of adenosine $A_{2B}$ receptors increases the likelihood of vascular injury, and provokes the onset of various vascular diseases. A high degree of selectivity for antagonism of adenosine $A_{2A}$ versus $A_{2B}$ receptors is therefore a highly desirable feature, especially in an anti-Parkinson's treatment, the target disease population for which is likely to be elderly and at risk of developing vascular disease heart disease (Yang D, Koupenova M, McCrann D J, Kopeikina K J, Kagan H M, Schreiber B M, and Ravid K (2008) "The A2b adenosine receptor protects against vascular injury", Proc. Natl. Acad Sci. 105(2): 792-796).

As previously mentioned, the compounds of the present invention also show greater selectivity for the adenosine $A_{2A}$ receptor than for the adenosine $A_3$ receptor. Again, this selectivity has significant benefits, as discussed below.

Adenosine released during cardiac ischemia exerts a potent, protective effect in the heart. There is strong evidence that activation of adenosine $A_3$ receptors plays a large part in mediating this protection (Liang and Jacobson, 1998). It is likely therefore that sustained blockade of adenosine $A_3$ receptors might increase the likelihood of complications resulting from any pre-existing or developing ischaemic heart disease, such as angina or heart failure. A high degree of selectivity for antagonism of adenosine $A_{2A}$ versus $A_3$ receptors is therefore a highly desirable feature, especially in an anti-Parkinson's treatment, the target disease population for which is likely to be elderly and at risk of ischaemic heart disease (Liang B T and Jacobson K A (1998). A physiological role of the adenosine $A_3$ receptor: Sustained cardioprotection. Proc. Natl. Acad. Sci. 95 (12): 6995-9).

In an aspect, the present invention provides compounds of formula (I):

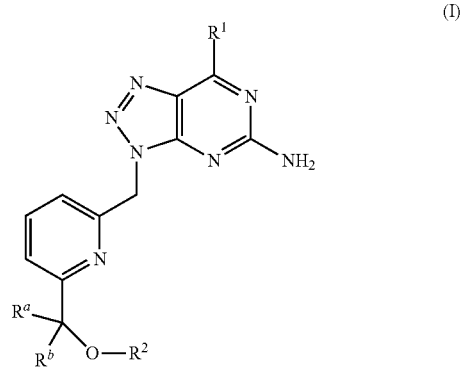

wherein:
$R^1$ is phenyl or heteroaryl, wherein said phenyl or said heteroaryl group may be optionally substituted with alkyl, alkoxy, halo or —CN;
$R^a$ is H or alkyl;
$R^b$ is H or alkyl;
or $R^a$ and $R^b$ together with the atom to which they are attached form a 3 to 8 membered saturated or partially saturated hydrocarbon ring or form a 4 to 8 membered saturated or partially saturated heterocylic ring comprising a ring member selected from O, N($R^3$) and S;
$R^2$ is H, alkyl or heterocycloalkyl, wherein said alkyl may optionally be substituted with halo, alkoxy or heterocycloalkyl;
provided that $R^2$ is selected from heterocycloalkyl and alkyl substituted by halo, alkoxy or heterocycloalkyl, when $R^1$ is furan-2-yl or 5-methyl-furan-2-yl and $R^a$ and $R^b$ are both H;
$R^3$ is H or alkyl;

wherein:
heteroaryl is a 5 or 6 membered aromatic ring, comprising one or two ring members selected from N, N($R^4$), S and O;
alkyl (or the alkyl group of the alkoxy group) is a linear or branched saturated hydrocarbon containing up to 10 carbon atoms;
heterocycloalkyl is a C-linked or N-linked 3 to 10 membered non-aromatic, monocyclic ring, wherein said heterocycloalkyl ring comprises 1, 2 or 3 ring members independently selected from N, N($R^4$), S(O)$_q$ and O;
$R^4$ is H or alkyl;
q is 0, 1 or 2;
and tautomers, stereoisomers, pharmaceutically acceptable salts and solvates thereof.

In an aspect the present invention provides a prodrug of a compound of formula (I) as herein defined, or a pharmaceutically acceptable salt thereof.

In an aspect the present invention provides an N-oxide of a compound of formula (I) as herein defined, or a prodrug or pharmaceutically acceptable salt thereof.

It will be understood that certain compounds of the present invention may exist in solvated, for example hydrated, as well as unsolvated forms. It is to be understood that the present invention encompasses all such solvated forms.

In an aspect, the present invention provides a pharmaceutical composition includes a pharmaceutically acceptable carrier and a compound of formula (I) as defined above, or a pharmaceutically acceptable salt or solvate thereof.

In an aspect, the present invention provides a method of treating a disorder comprising administering an effective dose of a compound of formula (I), or a pharmaceutically acceptable salt or solvate thereof, to a subject in need of treatment of a disorder treatable by purine receptor blocking.

In an aspect, the present invention provides a compound of formula (I), or a pharmaceutically acceptable salt or solvate thereof, for use in the treatment of a disorder treatable by purine receptor blocking.

In an aspect, the present invention provides for the use of a compound of formula (I), or a pharmaceutically acceptable salt or solvate thereof, in the manufacture of a medicament for the treatment of a disorder treatable by purine receptor blocking.

The disorder can be related to hyper functioning of purine receptors. The subject can be in need of adenosine receptor blocking. The purine receptors can be adenosine $A_{2A}$ receptors. The disorder can be a movement disorder. The movement disorder can be Parkinson's disease, Restless legs syndrome or nocturnal myoclonus; or the movement disorder can be drug-induced Parkinsonism, post-encephalitic Parkinsonism, Parkinsonism induced by poisoning or post-traumatic Parkinson's disease. The movement disorder can be progressive supernuclear palsy, Huntington's disease, multiple system atrophy, corticobasal degeneration, Wilson's disease, Hallerrorden-Spatz disease, progressive pallidal atrophy, Dopa-responsive dystonia-Parkinsonism, spasticity or other disorders of the basal ganglia which result in dyskinesias.

The treatment can include administering to the subject an additional drug useful in the treatment of movement disorders. The additional drug useful in the treatment of movement disorders can be a drug useful in the treatment of Parkinson's disease, such as, for example, L-DOPA or a dopamine agonist. The disorder can be depression, a cognitive or memory impairment disorder, acute or chronic pain, ADHD or narcolepsy. The cognitive or memory impairment disorder can be Alzheimer's disease.

In an aspect, the present invention provides subset of the compounds of formula (I), wherein:

$R^1$ is selected from the group consisting of 5-methyl-furan-2-yl, phenyl and 4-methylthiazol-2-yl;

$R^a$ is H or alkyl;

$R^b$ is H or alkyl;

or $R^a$ and $R^b$ together with the atom to which they are attached form a 4 to 6 membered saturated hydrocarbon ring or form a 5 or 6 membered saturated heterocyclic ring comprising a ring member selected from O, $N(R^3)$ and S;

$R^2$ is H, alkyl, alkoxyalkyl- or heterocycloalkyl;

provided that $R^2$ is H, alkoxyalkyl- or heterocycloalkyl when $R^1$ is 5-methyl-furan-2-yl and $R^a$ and $R^b$ are both H;

$R^3$ is H or alkyl;

wherein heteroaryl, alkyl (or the alkyl group of the alkoxy or alkoxyalkyl group) and heterocycloalkyl are as previously defined;

and tautomers, stereoisomers, pharmaceutically acceptable salts and solvates thereof.

The present invention also comprises the following aspects and combinations thereof:

In an aspect, the present invention provides a compound of formula (I) wherein $R^1$ is selected from phenyl and heteroaryl, wherein said phenyl or said heteroaryl may be optionally substituted with alkyl or alkoxy.

In an aspect, the present invention provides a compound of formula (I) wherein $R^1$ is selected from phenyl, thienyl, furanyl, pyrrolyl, pyrazolyl, imidazoyl, oxazolyl, isoxazolyl and thiazolyl, wherein each may be optionally substituted with alkyl or alkoxy.

In an aspect, the present invention provides a compound of formula (I) wherein $R^1$ is selected from phenyl, 2-furanyl, 2-pyrrolyl, 2-imidazoyl, 2-oxazolyl, and 2-thiazolyl, wherein each may be optionally substituted with alkyl or alkoxy.

In an aspect, the present invention provides a compound of formula (I) wherein $R^1$ is selected from 5-methyl-furan-2-yl, phenyl and 4-methylthiazol-2-yl.

In an aspect, the present invention provides a compound of formula (I) wherein $R^1$ is 5-methyl-furan-2-yl.

In an aspect, the present invention provides a compound of formula (I) wherein $R^a$ and $R^b$ together with the atom to which they are attached form a 4 to 6 membered saturated hydrocarbon ring or form a 5 or 6 membered saturated heterocylic ring comprising a ring member selected from O and $N(R^3)$; wherein $R^3$ is as previously defined.

In an aspect, the present invention provides a compound of formula (I) wherein $R^a$ and $R^b$ together with the atom to which they are attached form a tetrahydropyryl ring, a cyclobutyl ring, a cyclopentyl ring or a cyclohexyl ring.

In an aspect, the present invention provides a compound of formula (I) wherein $R^a$ and $R^b$ are independently selected from H and $(C_1-C_6)$alkyl.

In an aspect, the present invention provides a compound of formula (I) wherein $R^a$ and $R^b$ are independently selected from H and methyl.

In an aspect, the present invention provides a compound of formula (I) wherein $R^a$ and $R^b$ are both H.

In an aspect, the present invention provides a compound of formula (I) wherein $R^2$ is selected from H, $(C_1-C_6)$alkyl and heterocycloalkyl, wherein said $(C_1-C_6)$alkyl may optionally be substituted with fluoro, $(C_1-C_6)$alkoxy, tetrahydrofuranyl, tetrahydropyranyl, pyrrolidinyl and piperidinyl.

In an aspect, the present invention provides a compound of formula (I) wherein $R^2$ is selected from H, $(C_1-C_4)$alkyl and tetrahydrofuranyl, wherein said $(C_1-C_4)$alkyl may optionally be substituted with fluoro, $(C_1-C_3)$alkoxy and tetrahydrofuranyl.

In an aspect, the present invention provides a compound of formula (I) wherein $R^2$ is selected from H and tetrahydrofuranyl.

In an aspect, heteroaryl is a 5 membered aromatic ring, containing one or two N atoms, or one N atom and one $NR^4$ atom, or one $NR^4$ atom and one S or one O atom; wherein $R^4$ is as previously defined.

In an aspect, heterocycloalkyl is a C-linked 5 or 6 membered non-aromatic, monocyclic ring, wherein said ring comprises 1 or 2 ring members independently selected from $NR^4$ and O; wherein $R^4$ is as previously defined.

In an aspect, the present invention provides a compound of formula (I) selected from:

7-(5-methylfuran-2-yl)-3-(6-[2-isopropyloxyethyoxy] oxymethylpyrid-2-ylmethyl)-3H-[1,2,3]triazolo[4,5-d]pyrimidin-5-amine;

7-(5-methylfuran-2-yl)-3-(6-[1-hydroxy-1-methylethyl] pyrid-2-ylmethyl)-3H-[1,2,3]triazolo[4,5-d]pyrimidin-5-amine;

7-(5-methylfuran-2-yl)-3-(6-[1-hydroxy-1-cyclopentyl] pyrid-2-ylmethyl)-3H-[1,2,3]triazolo[4,5-d]pyrimidin-5-amine;

7-(5-methylfuran-2-yl)-3-(6-[4-hydroxytetrahydropyran-4-yl]pyrid-2-ylmethyl)-3H-[1,2,3]triazolo[4,5-d]pyrimidin-5-amine;

S-7-phenyl-3-(6-[tetrahydrofuran-3-yl]oxymethylpyrid-2-ylmethyl)-3H-[1,2,3]triazolo[4,5-d]pyrimidin-5-amine;

7-phenyl-3-(6-[1-hydroxy-1-methylethyl]pyrid-2-ylmethyl)-3H-[1,2,3]triazolo[4,5-d]pyrimidin-5-amine;

7-phenyl-3-(6-[1-hydroxy-1-cyclopentyl]pyrid-2-ylmethyl)-3H-[1,2,3]triazolo[4,5-d]pyrimidin-5-amine;

7-phenyl-3-(6-[1-hydroxycyclobutyl]pyrid-2-ylmethyl)-3H-[1,2,3]triazolo[4,5-d]pyrimidin-5-amine;

7-phenyl-3-(6-[methoxymethyl]pyrid-2-ylmethyl)-3H-[1,2,3]triazolo[4,5-d]pyrimidin-5-amine;

S-7-(3-methoxyphenyl)-3-(6-[tetrahydrofuran-3-yl] oxymethylpyrid-2-ylmethyl)-3H-[1,2,3]triazolo[4,5-d]pyrimidin-5-amine;

S-7-(5-methylfuran-2-yl)-3-(6-[tetrahydrofuran-3-yl] oxymethylpyrid-2-ylmethyl)-3H-[1,2,3]triazolo[4,5-d]pyrimidin-5-amine;

7-(3-methoxyphenyl)-3-(6-[1-hydroxy-1-cyclopentyl] pyrid-2-ylmethyl)-3H-[1,2,3]triazolo[4,5-d]pyrimidin-5-amine;

7-(3-methoxyphenyl)-3-(6-[4-hydroxytetrahydropyran-4-yl]pyrid-2-ylmethyl)-3H-[1,2,3]triazolo[4,5-d]pyrimidin-5-amine;

7-(3-methoxyphenyl)-3-(6-[1-hydroxycyclobutyl]pyrid-2-ylmethyl)-3H-[1,2,3]triazolo[4,5-d]pyrimidin-5-amine;

7-(3-methoxyphenyl)-3-(6-[methoxymethyl]pyrid-2-ylmethyl)-3H-[1,2,3]triazolo[4,5-d]pyrimidin-5-amine;

7-(5-methylfuran-2-yl)-3-(6-[1-hydroxy-1-cyclohexyl] pyrid-2-ylmethyl)-3H-[1,2,3]triazolo[4,5-d]pyrimidin-5-amine;

S-7-(3-cyanophenyl)-3-(6-[tetrahydrofuran-3-yl]oxymethylpyrid-2-ylmethyl)-3H-[1,2,3]triazolo[4,5-d]pyrimidin-5-amine;

7-(3-cyanophenyl)-3-(6-[1-hydroxy-1-methylethyl]pyrid-2-ylmethyl)-3H-[1,2,3]triazolo[4,5-d]pyrimidin-5-amine;

7-(3-cyanophenyl)-3-(6-[4-hydroxytetrahydropyran-4-yl] pyrid-2-ylmethyl)-3H-[1,2,3]triazolo[4,5-d]pyrimidin-5-amine;

7-(3-cyanophenyl)-3-(6-[1-hydroxycyclobutyl]pyrid-2-ylmethyl)-3H-[1,2,3]triazolo[4,5-d]pyrimidin-5-amine;

7-(3-methoxyphenyl)-3-(6-[1-hydroxy-1-methylethyl]pyrid-2-ylmethyl)-3H-[1,2,3]triazolo[4,5-d]pyrimidin-5-amine;

7-(3-cyanophenyl)-3-(6-[methoxymethyl]pyrid-2-ylmethyl)-3H-[1,2,3]triazolo[4,5-d]pyrimidin-5-amine;

S-7-(4-methylthiazol-2-yl)-3-(6-[tetrahydrofuran-3-yl]oxymethylpyrid-2-ylmethyl)-3H-[1,2,3]triazolo[4,5-d]pyrimidin-5-amine;

7-(4-methylthiazol-2-yl)-3-(6-[1-hydroxy-1-cyclopentyl]pyrid-2-ylmethyl)-3H-[1,2,3]triazolo[4,5-d]pyrimidin-5-amine;

7-(4-methylthiazol-2-yl)-3-(6-[4-hydroxytetrahydropyran-4-yl]pyrid-2-ylmethyl)-3H-[1,2,3]triazolo[4,5-d]pyrimidin-5-amine;

7-(5-methylfuran-2-yl)-3-(6-[1-hydroxycyclobutyl]pyrid-2-ylmethyl)-3H-[1,2,3]triazolo[4,5-d]pyrimidin-5-amine;

7-(4-methylthiazol-2-yl)-3-(6-[1-hydroxycyclobutyl]pyrid-2-ylmethyl)-3H-[1,2,3]triazolo[4,5-d]pyrimidin-5-amine;

7-(4-methylthiazol-2-yl)-3-(6-[methoxymethyl]pyrid-2-ylmethyl)-3H-[1,2,3]triazolo[4,5-d]pyrimidin-5-amine;

7-(5-methylfuran-2-yl)-3-(6-[difluoromethyloxymethyl]-pyrid-2-ylmethyl)-3H-[1,2,3]triazolo[4,5-d]pyrimidin-5-amine;

7-phenyl-3-(6-[4-hydroxytetrahydropyran-4-yl]pyrid-2-ylmethyl)-3H-[1,2,3]triazolo[4,5-d]pyrimidin-5-amine;

7-(5-methylfuran-2-yl)-3-(6-[2-ethoxyethoxymethyl]pyrid-2-ylmethyl)-3H-[1,2,3]triazolo[4,5-d]pyrimidin-5-amine;

7-(5-methylfuran-2-yl)-3-(6-[tetrahydrofuran-2-ylmethyl]oxymethylpyrid-2-ylmethyl)-3H-[1,2,3]triazolo[4,5-d]pyrimidin-5-amine;

7-(5-methylfuran-2-yl)-3-(6-[tetrahydrofuran-3-ylmethyl]oxymethylpyrid-2-ylmethyl)-3H-[1,2,3]triazolo[4,5-d]pyrimidin-5-amine;

7-(5-methylfuran-2-yl)-3-(6-[1-methoxy-1-methylethyl]oxymethylpyrid-2-ylmethyl)-3H-[1,2,3]triazolo[4,5-d]pyrimidin-5-amine;

7-(3-cyanophenyl)-3-(6-[1-hydroxy-1-cyclopentyl]pyrid-2-ylmethyl)-3H-[1,2,3]triazolo[4,5-d]pyrimidin-5-amine;

7-(5-methylfuran-2-yl)-3-(6-[2,2,2-trifluoroethyl]oxymethylpyrid-2-ylmethyl)-3H-[1,2,3]triazolo[4,5-d]pyrimidin-5-amine;

S-7-(thiazol-2-yl)-3-(6-[tetrahydrofuran-3-yl]oxymethylpyrid-2-ylmethyl)-3H-[1,2,3]triazolo[4,5-d]pyrimidin-5-amine;

7-(4-methylthiazol-2-yl)-3-(6-[1-hydroxy-1-methylethyl]pyrid-2-ylmethyl)-3H-[1,2,3]triazolo[4,5-d]pyrimidin-5-amine;

and pharmaceutically acceptable salts and solvates thereof.

The skilled person will appreciate that each of the compounds identified above, or identified in the Examples provided herein below, taken alone or with any combination of the other identified compounds represents an independent aspect of the invention.

Definitions:

The term "alkyl" is as previously defined and denotes saturated hydrocarbon residues including:

linear groups up to 10 atoms ($C_1$-$C_{10}$), or of up to 6 atoms ($C_1$-$C_6$), or of up to 4 atoms ($C_1$-$C_4$). Examples of such alkyl groups include, but are not limited to, $C_1$-methyl, $C_2$-ethyl, $C_3$-propyl and $C_4$-n-butyl.

branched groups of between 3 and 10 atoms ($C_3$-$C_{10}$), or of up to 7 atoms ($C_3$-$C_7$), or of up to 4 atoms ($C_3$-$C_4$). Examples of such alkyl groups include, but are not limited to, $C_3$-iso-propyl, $C_4$-sec-butyl, $C_4$-iso-butyl, $C_4$-tert-butyl and $C_5$-neo-pentyl.

The term "alkoxy" denotes O-linked hydrocarbon residues including:

linear groups of between 1 and 6 atoms ($C_1$-$C_6$), or of between 1 and 4 atoms ($C_1$-$C_4$). Examples of such alkoxy groups include, but are not limited to, $C_1$-methoxy, $C_2$-ethoxy, $C_3$-n-propoxy and $C_4$-n-butoxy.

branched groups of between 3 and 6 atoms ($C_3$-$C_6$) or of between 3 and 4 atoms ($C_3$-$C_4$). Examples of such alkoxy groups include, but are not limited to, $C_3$-iso-propoxy, and $C_4$-sec-butoxy and tert-butoxy.

The term "alkoxyalkyl-" denotes an alkyl-O-alkyl-group in which alkyl is as described below. Examples of suitable alkoxyalkyl-groups include, but are not limited to, methoxymethyl ($CH_3OCH_2$—) and ethoxymethyl ($C_2H_5OCH_2$—).

The term "halo" denotes a halogen atom selected from Cl, F, Br and I.

The term "heterocycloalkyl" is as defined above. Examples of suitable heterocycloalkyl groups include oxiranyl, aziridinyl, azetidinyl, tetrahydrofuranyl, pyrrolidinyl, tetrahydropyranyl, piperidinyl, N-methylpiperidinyl, morpholinyl, N-methyl morpholinyl, thiomorpholinyl, thiomorpholinyl-1-oxide, thiomorpholinyl-1,1-dioxide, piperazinyl, N-methylpiperazinyl, azepinyl oxazepinyl, diazepinyl, and 1,2,3,4-tetrahydropyridinyl.

The term "heteroaryl" is as defined above. Examples of suitable heteroaryl groups include thienyl, furanyl, pyrrolyl, pyrazolyl, imidazoyl, oxazolyl, isoxazolyl, thiazolyl, isothiazolyl, pyridinyl, pyridazinyl, pyrimidinyl and pyrazinyl.

The term "C-linked", such as in "C-linked heterocycloalkyl", means that the heterocycloalkyl group is joined to the remainder of the molecule via a ring carbon atom.

The term "N-linked", such as in "N-linked heterocycloalkyl", means that the heterocycloalkyl group is joined to the remainder of the molecule via a ring nitrogen atom.

The term "O-linked", such as in "O-linked hydrocarbon residue", means that the hydrocarbon residue is joined to the remainder of the molecule via an oxygen atom.

In groups such as "alkoxyalkyl-" and "—CN", the symbol "-" denotes the point of attachment of the group to the remainder of the molecule.

"Pharmaceutically acceptable salt" means a physiologically or toxicologically tolerable salt and includes, when appropriate, pharmaceutically acceptable base addition salts and pharmaceutically acceptable acid addition salts. Hemisalts of acids and bases can also be formed, for example, hemisulfate and hemicalcium salts. For a review of suitable salts, see "Handbook of Pharmaceutical Salts: Properties, Selection and Use" by Stahl and Wermuth (Wiley-VCH, Weinheim, Germany, 2002).

"Prodrug" refers to a compound which is convertible in vivo by metabolic means (e.g. by hydrolysis, reduction or oxidation) to a compound of the invention. Suitable groups for forming pro-drugs are described in "The Practice of Medicinal Chemistry, $2^{nd}$ Ed. pp 561-585 (2003) and in F. J. Leinweber, *Drug Metab. Res.*, 1987, 18, 379.

The compounds of the invention can exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when the solvent is water.

Where compounds of the invention exist in one or more geometrical, optical, enantiomeric, diastereomeric and tautomeric forms, including but not limited to cis- and trans-forms, E- and Z-forms, R-, S- and meso-forms, keto-, and enol-forms. Unless otherwise stated a reference to a particular compound includes all such isomeric forms, including racemic and other mixtures thereof. Where appropriate such isomers can be separated from their mixtures by the application or adaptation of known methods (e.g. chromatographic techniques and recrystallisation techniques). Where appropriate such isomers can be prepared by the application or adaptation of known methods (e.g. asymmetric synthesis).

For example, the use of certain combinations of substituents $R^a$ and $R^b$ can generate chiral compounds of the present invention such as:

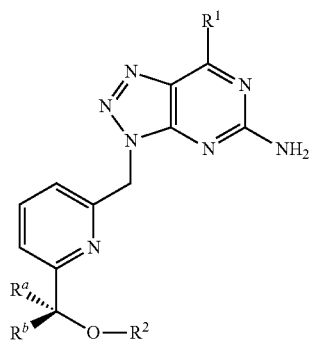

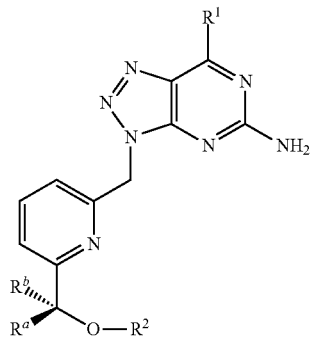

Similarly, the use of certain $R^2$ substituents can generate chiral compounds of the present invention such as:

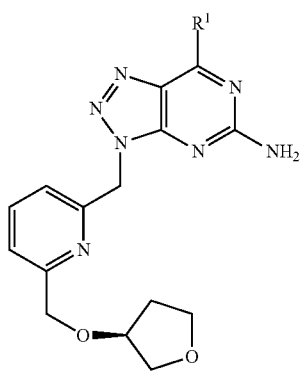

-continued

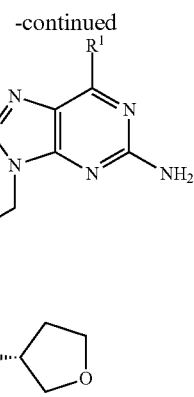

In the context of the present invention, references herein to "treatment" include references to curative, palliative and prophylactic treatment.

Therapeutic Applications

The compounds of the present invention are useful as purine receptor antagonists, for example, as adenosine $A_{2A}$ antagonists.

Pharmaceutically acceptable salts of the compounds of the present invention are also suitable as purine receptor antagonists, for example, as adenosine $A_{2A}$ antagonists.

The compounds of the present invention can be used for treating or preventing a disorder in which the blocking of purine receptors, particularly adenosine receptors and more particularly adenosine $A_{2A}$ receptors, may be beneficial. The compounds can be administered to a subject in need of such treatment. For example, an effective dose of a compound of formula (I) or a pharmaceutically acceptable salt or prodrug thereof can be administered to a subject. The disorder may be caused by the hyperfunctioning of the purine receptors.

Disorders of particular interest include those in which the blocking of purine receptors, particularly adenosine receptors and more particularly adenosine $A_{2A}$ receptors, may be beneficial. These include movement disorders such as Parkinson's disease, drug-induced Parkinsonism, post-encephalitic Parkinsonism, Parkinsonism induced by poisoning (for example MlP, manganese, carbon monoxide) and post-traumatic Parkinson's disease (punch-drunk syndrome).

Other movement disorders in which the blocking of purine receptors, may be of benefit include progressive supernuclear palsy, Huntingtons disease, multiple system atrophy, corticobasal degeneration, Wilsons disease, Hallerrorden-Spatz disease, progressive pallidal atrophy, Dopa-responsive dystonia-Parkinsonism, spasticity or other disorders of the basal ganglia which result in abnormal movement or posture. The present invention may also be effective in treating Parkinson's with on-off phenomena; Parkinson's with freezing (end of dose deterioration); and Parkinson's with prominent dyskinesias.

The compounds of formula (I) may be used or administered in combination with one or more additional drugs useful in the treatment of movement disorders, such as L-DOPA or a dopamine agonist, the components being in the same formulation or in separate formulations for administration simultaneously or sequentially.

Other disorders in which the blocking of purine receptors, particularly adenosine receptors and more particularly adenosine $A_{2A}$, receptors may be beneficial include acute and chronic pain; for example neuropathic pain, cancer pain, trigeminal neuralgia, migraine and other conditions associated with cephalic pain, primary and secondary hyperalgesia, inflammatory pain, nociceptive pain, tabes *dorsalis*, phantom limb pain, spinal cord injury pain, central pain, post-herpetic pain and HIV pain; affective disorders including mood disorders such as bipolar disorder, seasonal affective disorder, depression, manic depression, atypical depression and monodepressive disease; central and peripheral nervous system degenerative disorders including corticobasal degeneration, demyelinating disease (multiple sclerosis, disseminated sclerosis), Friedrich's ataxia, motoneuron disease (amyotrophic lateral sclerosis, progressive bulbar atrophy), multiple system atrophy, myelopathy, radiculopathy, peripheral neuropathy (diabetic neuropathy, tabes dorsalis, drug induced neuropathy, vitamin deficiency), systemic lupus erythamatosis, granulomatous disease, olivoponto-cerebellar atrophy, progressive pallidal atrophy, progressive supranuclear palsy, spasticity; schizophrenia and related psychoses; cognitive disorders including dementia, Alzheimer's Disease, Frontotemporal dementia, multi-infarct dementia, AIDS dementia, dementia associated with Huntington's Disease, Lewy body dementia, senile dementia, age-related memory impairment, cognitive impairment associated with dementia, Korsakoff syndrome, dementia pugilans; attention disorders such as attention-deficit hyperactivity disorder (ADHD), attention deficit disorder, minimal brain dysfunction, brain-injured child syndrome, hyperkinetic reaction childhood, and hyperactive child syndrome; central nervous system injury including traumatic brain injury, neurosurgery (surgical trauma), neuroprotection for head injury, raised intracranial pressure, cerebral edema, hydrocephalus, spinal cord injury; cerebral ischemia including transient ischemic attack, stroke (thrombotic stroke, ischemic stroke, embolic stroke, hemorrhagic stroke, lacunar stroke) subarachnoid hemorrhage, cerebral vasospasm, neuroprotection for stroke, peri-natal asphyxia, drowning, cardiac arrest, subdural hematoma; myocardial ischemia; muscle ischemia; sleep disorders such as hypersomnia and narcolepsy; eye disorders such as retinal ischemia-reperfusion injury and diabetic neuropathy; cardiovascular disorders such as claudication and hypotension; and diabetes and its complications.

Synthetic Methods

Compounds of formula (I) may be prepared according to conventional synthetic methods. For example compounds of formula (I) may be synthesized by methods such as those illustrated in Reaction Scheme 1. In this scheme R represents —$(CR^aR^b)$—O—$R^2$.

Compounds of formula (4) may be prepared from compounds of formula (3) by standard methods such as reaction with an appropriate alkyl halide, or substituted alkyl halide (e.g., an arylalkyl halide) in the presence of a suitable base such as sodium hydride.

Compounds of formula (3) may be prepared from the known chloro compound of formula (2) by standard methods such as phenyl or heteroaryl coupling reactions. Suitable phenyl or heteroaryl coupling reactions would include reaction with an appropriate phenyl- or heteroaryl-boronic acid derivative, an phenyl- or heteroaryl-trialkylstannane derivative or an phenyl- or heteroaryl-zinc halide derivative in the presence of a suitable catalyst such as a palladium complex.

Compounds of formula (3) may also be prepared from compounds of formula (7) by standard methods such as treatment with isoamyl nitrite or sodium nitrite. Compounds of formula (7) are either known in the literature or can be prepared from compounds of formula (6) by standard methods such as reduction with hydrogen in the presence of a suitable catalyst such as Pd. Compounds of formula (6) are either known in the literature or can be prepared from the known compound of formula (5) by standard methods such as phenyl or heteroaryl coupling reactions as described above.

Compounds of formula (I) may also be synthesized by standard methods such as those illustrated in Reaction Scheme 2. In this scheme R represents —$(CR^aR^b)$—O—$R^2$.

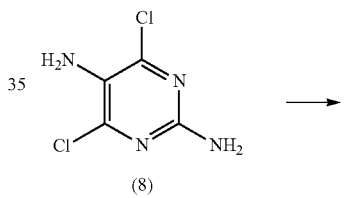

Reaction Scheme 2

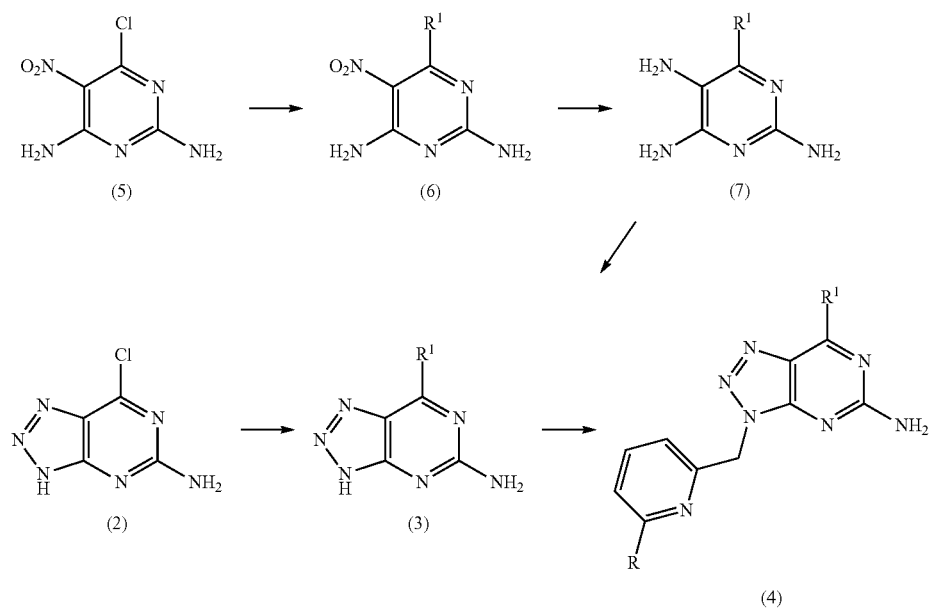

Reaction Scheme 1

-continued

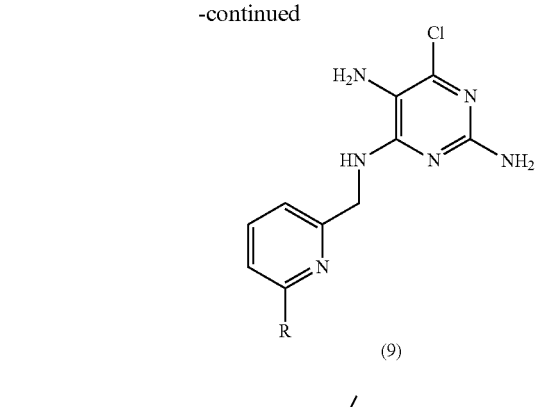

(9)

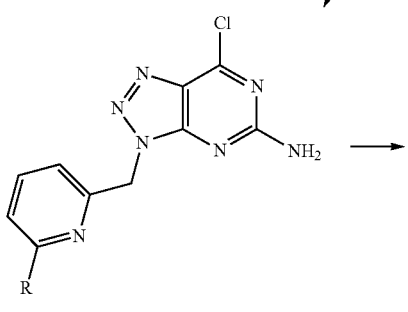

(10)

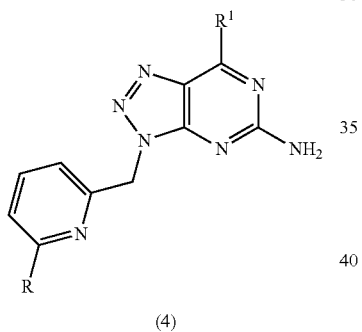

(4)

literature such as the treatment of the compound of formula (8) with an appropriate amine in a suitable solvent at elevated temperature.

Compounds of formula (10) can also be prepared by a modified version of Reaction Scheme 2, in which the 5-amino group of compound (8) is protected, as shown in Reaction Scheme 2A. In this scheme R represents —(CR$^a$R$^b$)—O—R$^2$ and PG represents a protecting group.

Reaction Scheme 2A:

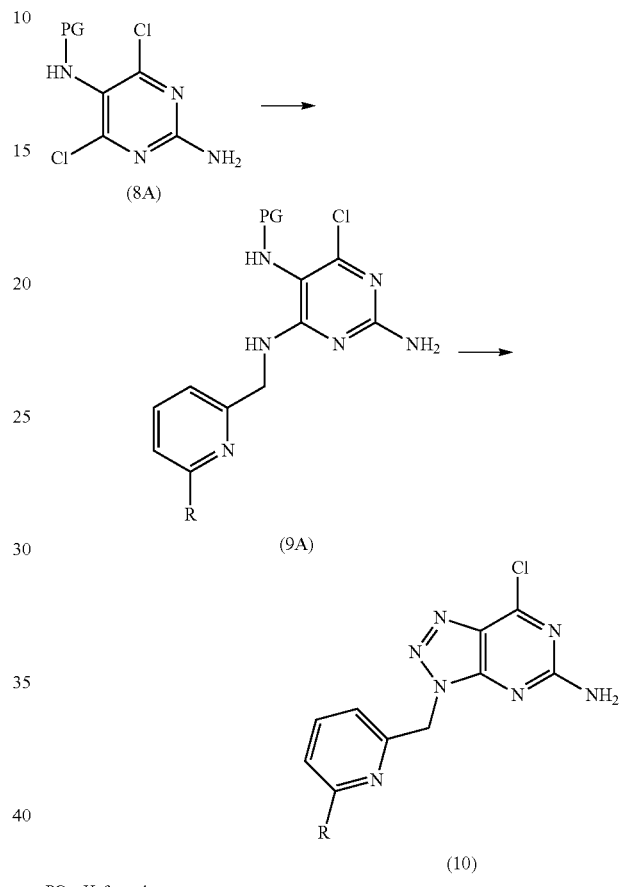

PG = H, formyl

Compounds of formula (4) may be prepared from compounds of formula (10) by standard methods such as phenyl or heteroaryl coupling reactions as described above. Compounds of formula (10) can be prepared by methods analogous to those described in the literature. For example compounds of formula (10) may be prepared from compounds of formula (9) by standard methods such as treatment with isoamyl nitrite or sodium nitrite. Compounds of formula (9) can be prepared by methods described in the Compounds of formula (10) can be prepared from compounds of formula (9A) by standard methods such as treatment with isoamyl nitrite or sodium nitrite. Compounds of formula (9A) can be prepared by methods such as the treatment of the compound of formula (8A) with an appropriate amine in a suitable solvent at elevated temperature.

Compounds of formula (I) may also be synthesized by standard methods such as those illustrated in Reaction Scheme 3. In this scheme R represents —(CR$^a$R$^b$)—O—R$^2$.

Reaction Scheme 3

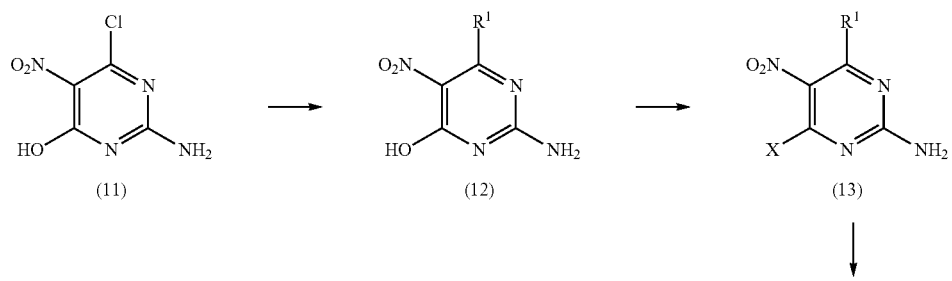

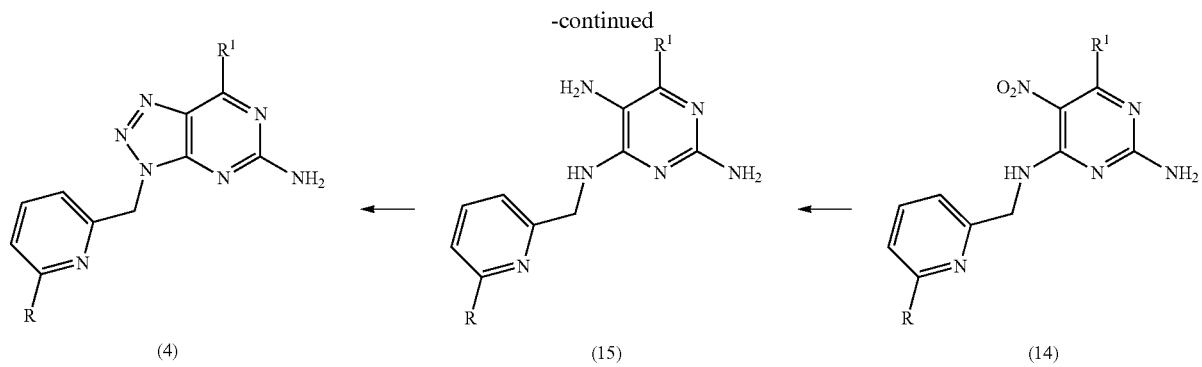

Compounds of formula (4) can be prepared from compounds of formula (15) by standard methods such as treatment with isoamyl nitrite. Compounds of formula (15) may be prepared from compounds of formula (14) by standard methods such as reduction with hydrogen in the presence of a suitable catalyst such as Pd. Compounds of formula (14) may be prepared from compounds of formula (13), where X is a suitable leaving group such as a tosylate or triflate group, by standard methods such as treatment with a suitable amine in the presence of a suitable base such as triethylamine. Compounds of formula (13) where X is a suitable leaving group are either known in the literature or may be prepared from compounds of formula (12) by standard methods such as treatment with tosyl chloride or triflic anhydride in the presence of a suitable base such as triethylamine or 2,6-dimethylpyridine. Compounds of formula (12) are either known in the literature or may be prepared from the known compound of formula (11) by standard methods such as phenyl or heteroaryl coupling reactions as described above.

Compounds of formula (I) can be used in the form of pharmaceutically acceptable salts derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compound may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Pharmaceutical compositions can include a compound of formula (I), or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant.

The pharmaceutical compositions can be orally administered in any orally acceptable dosage form including, but not limited to, capsules, tablets, aqueous suspensions or solutions.

In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

A pharmaceutical composition can include an effective amount of a compound of formula (I). An effective amount is defined as the amount which is required to confer a therapeutic effect on the treated patient, and will depend on a variety of factors, such as the nature of the inhibitor, the size of the patient, the goal of the treatment, the nature of the pathology to be treated, the specific pharmaceutical composition used, and the judgment of the treating physician. For reference, see Freireich et al., Cancer Chemother. Rep. 1966, 50, 219 and Scientific Tables, Geigy Pharmaceuticals, Ardley, N.Y., 1970, 537. Dosage levels of between about 0.001 and about 100 mg/kg body weight per day, preferably between about 0.1 and about 10 mg/kg body weight per day of the active ingredient compound are useful.

The following examples are for the purpose of illustration only and are not intended to be limiting.

EXAMPLES

Example 1

S-7-(5-methylfuran-2-yl)-3-(6-[tetrahydrofuran-3-yl]
oxymethylpyrid-2-ylmethyl)-3H-[1,2,3]triazolo[4,5-d]pyrimidin-5-amine 2-Amino-6-chloro-5-nitro-4-pyrimidinol 250 mL (5 volumes) of concentrated sulfuric acid was stirred in a 1000 mL round bottom flask (22° C.). To this, 2-amino-6-chloro-4-pyrimidinol (50 g) was added in portions. The temperature increased rapidly with early additions, stabilizing at a temperature of 40° C. Later additions had less effect on the temperature, a maximum of approx. 45° C. being recorded. Prior to addition of fuming nitric acid (45 mL, 0.9 volumes), the mixture was cooled (using an ice bath) to 20° C. In portions of roughly 1.5 mL (reflecting pipette volume), nitric acid was added dropwise at a steady rate (ca. 1 min between each portion). Early portions had the greatest effect on the temperature, the controlled exotherms reaching a temperature of approx. 26° C. before returning to 20° C. under the influence of the ice bath. Later portions had little effect, and the temperature was maintained at approx. 21° C. After 45 mL of fuming nitric acid had been added in this way, the mixture was allowed to stir for 2 hr (during this period the ice bath was removed and the temperature stabilised at room temperature ca. 22° C.). The entire mixture was poured onto stirred ice/water (1200 mL) and the resulting yellow solid filtered under vacuum. The product was washed in succession with water (600 mL), ethanol (600 mL) and diethylether (600 mL). This method gave 63.5 g (98% yield) of the required nitro-pyrimidinol.

2-Amino-6-(5-methyl-2-furyl)-5-nitro-4-pyrimidinol
(12)

A biphasic solvent mixture of 1100 mL (22 volumes) tetrahydrofuran and 550 mL (11 volumes) of aqueous sodium carbonate solution was stirred at 22° C. in a 3000 mL three-necked round-bottomed flask. To this, 2-amino-6-chloro-5-nitro-4-pyrimidinol (11) was added portionwise. The resulting yellow solution was treated with a solution of 5-methylfuran-2-boronic acid in ca. 30 mL THF (0.43 mol, 2 eq 2-methylfuran initially). Tetrakis(triphenylphosphine) palladium (0) (5%, 0.0072 moles, 8.32 g) was added and the reaction mixture heated to a temperature of 70° C. for 3 hr. The reaction mixture was cooled to 22° C. A small amount of turbidity was apparent at this point. The entire mixture was filtered and the filtrate reduced in vacuo to remove the tetrahydrofuran phase, leaving behind the alkaline aqueous phase. 1000 mL (20 volumes) ethyl acetate was added and the mixture stirred vigorously for 15 min (this step serves to wash out neutral contaminants, particularly triphenylphosphine oxide). The aqueous and organic phases were separated and the organic phase back-extracted with aqueous sodium carbonate (800 mL). The combined aqueous phase was cooled using an ice-bath and acidified (through dropwise addition of HCl) to pH 7. The resulting bright yellow precipitate was filtered under vacuum, washed with water and dried at 40° C. This method gave 37.8 g (67%) of the required product.

5-Methylfuran-2-boronic acid 1000 mL (25 volumes) of anhydrous tetrahydrofuran was stirred at 22° C. under a nitrogen atmosphere in a 2000 mL three-necked flask. 41.16 mL (0.43 mol) 2-methylfuran was added followed by 65 mL (0.43 mol, 1 eq) N,N,N',N'-tetramethylethylenediamine. The solution was cooled to −78° C. and treated dropwise with n-butyllithium (1 eq, 172 mL, 2.5 M solution in hexanes). The solution was stirred at 78° C. for a further 15 min before being slowly warmed to 22° C. Before dropwise addition of trimethylborate (2 eq, 0.86 mol, 96.4 mL), the solution was re-cooled to −78° C. Again, the solution was allowed to slowly warm to 22° C. Hydrolysis of the newly formed boronic ester was achieved through the addition of methanol:water (9:1, 280 mL). After 15 min the entire solution was reduced in vacuo to leave a yellow/white solid. To ensure complete hydrolysis, the solid was taken up in further methanol (100 mL) and reduced in vacuo four times, eventually leaving a dark orange crude residue. This residue was taken up in ca. 30 mL THF and used directly in the Suzuki coupling detailed above—the initial amount of 2-methylfuran used corresponds to 2 eq of the pyrimidinol starting material.

4-(5-Methyl-2-furyl)-5-nitro-6-(p-toluenesulphonyloxy)pyrimidine-2-amine (13)

A stirred suspension of 2-amino-6-(5-methyl-2-furyl)-5-nitro-4-pyrimidinol (12) (20.96 g, 0.089 mol) in dry acetonitrile (800 mL, 40 volumes) in a flame-dried three-necked flask at 22° C. was treated with triethylamine (27.24 mL, 0.196 mol, 2.2 eq). The resulting triethylamine salt was clearly insoluble in the reaction solvent, a thick yellow precipitate becoming apparent. The mixture was heated to a temperature of 50° C. and treated portionwise with para-toluenesulfonyl chloride (18.57 g, 0.097 mol, 1.1 eq). The yellow precipitate was rapidly replaced by a dark orange/brown solution. Stirring at 50° C. was continued for a further 3.5 hr, after which time LC-MS and TLC (1:1 EtOAc:isohexane) analysis indicated a complete reaction. The reaction mixture was cooled to 22° C. and reduced in vacuo to yield a light brown solid. This was dissolved in dichloromethane (800 mL, 40 volumes) and washed twice with 1.2-M aqueous hydrochloric acid. The organic fraction was dried over magnesium sulfate and reduced in vacuo to yield a cream coloured solid. Trituration with toluene was effective in removing excess tosyl chloride to give the required tosylate product (compound 13) as an off-white solid. Drying at 40° C. left 22.33 g (65% yield).

(S)-{6-(Tetrahydrofuran-3-yl)oxymethyl]pyridin-2-ylmethylamino}-4-(5-methyl-2-furyl)-5-nitropyrimidine-2-amine A stirred solution of 4-(5-methyl-2-furyl)-5-nitro-6-(p-toluenesulphonyloxy)pyrimidine-2-amine (13) (26.3 g, 0.067 mol) in dry dimethoxyethane (1100 mL, 40 volumes) in a sealed, flame-dried, three-necked flask was treated with a solution of the (S)-6-(tetrahydrofuran-3-yloxymethyl)-2-pyridinemethanamine in dry DME (16.72 g, 0.080 mol, 1.2 eq). This solution was subsequently treated with triethylamine (27.96 mL, 0.201 mol, 3 eq) and warmed to a temperature of 50° C. After 18 hr, LC-MS analysis indicated the reaction to be ca. 90% complete (TLC (1:1 EtOAc isohexane) indicated residual starting material further triethylamine addition and longer reaction time did not drive the reaction any further). The reaction mixture was cooled to 22° C. and poured onto 1.25 M HCl(aq) (1200 mL). To this, ethyl acetate (1000 mL) was added and the mixture stirred vigorously for 15 min. The aqueous phase was separated and neutralised using 2M aqueous sodium carbonate solution. The resulting bright yellow precipitate was filtered, washed with water and dried at 40° C. This method gave 24.61 g (86% yield) of the required product.

(S)-3-{6-(Tetrahydrofuran-3-yl)oxymethyl]pyridin-2-ylmethyl}-7-(5-methyl-2-furyl)-3H-[1,2,3]triazolo[4,5-d]pyrimidin-5-ylamine To a stirred suspension of (S)-{6-(tetrahydrofuran-3-yl)oxymethyl]pyridin-2-ylmethylamino}-4-(5-methyl-2-furyl)-5-nitropyrimidine-2-amine (4) (24 g, 0.056 mol.) in ethanol (900 mL, 37 volumes), platinum (IV) oxide (crystal, 1.27 g, 0.0056 mol., 10% eq) was added. The flask was thoroughly evacuated and placed under an atmosphere of hydrogen. After 18 hr at 22° C. the former suspension of the starting material was now a dark solution of the triamine (confirmed by TLC and a crude $^1$H NMR). The solution was filtered through a pad of Celite and the filtrate acidified with c. HCl (30 mL). The acidic solution was cooled to 0° C. and treated dropwise with an aqueous solution of sodium nitrite (15.46 g, 0.224 mol, 4 eq, 60 mL H$_2$O). The solution was stirred at 0° C. for 2 hr. The reaction mixture was basified using saturated aqueous sodium bicarbonate (pH ca. 8). The ethanol solvent was removed in vacuo causing the precipitation of the product from the remaining aqueous fraction. The light brown solid was filtered and dried at 40° C. This method gave 20.62 g (90% yield) of the title compound in ca. 95% purity.

Example 1A

S-7-(5-methylfuran-2-yl)-3-(6-[tetrahydrofuran-3-yl]oxymethylpyrid-2-ylmethyl)-3H-[1,2,3]triazolo[4,5-d]pyrimidin-5-amine, alternate synthesis (S)-2-Bromomethyl-6-(tetrahydrofuran-3-yloxymethyl)pyridine Prepared from 2,6-bis(bromomethyl)pyridine and (S)-tetrahydrofuran-3-ol by the alkylation method described for the final step of Example 32 to give the title compound (24%); NMR $\delta_H$ (400 MHz, CDCl$_3$) 7.70 (1H, t, J 7.5 Hz), 7.39 (1H, d, J 7.5 Hz), 7.34 (1H, d, J 7.5 Hz), 4.67-4.59 (2H, m), 4.52 (2H, s), 4.31-4.26 (1H, m) 3.98-3.81 (4H, m), 2.11-1.99 (2H, m); (M+H)$^+$ 272, 274.

(S)-3-{6-(Tetrahydrofuran-3-yl)oxymethyl]pyridin-2-ylmethyl}-7-(5-methyl-2-furyl)-3H-[1,2,3]triazolo[4,5-d]pyrimidin-5-ylamine Prepared from 7-(5-methyl-2-furyl)-1H-[1,2,3]triazolo[4,5-d]-ylamine and (S)-2-bromomethyl-6-(tetrahydrofuran-3-yloxymethyl)pyridine by the alkylation method described in Example 36.

Mp: 207.4-207.8° C.; IR $v_{max}$ (DR)/cm$^{-1}$ 3514, 3294, 3170, 2938, 2868, 1631, 1609, 1576, 1540, 1498, 1459 and 1431; NMR $\delta_H$ (400 MHz, DMSO) 7.88 (1H, d, J 3.5 Hz), 7.78 (1H, t, J 8.0 Hz), 7.35 (1H, d, J 8.0 Hz), 7.27 (2H, br s), 7.05 (1H, d, J 8.0 Hz), 6.52-6.50 (1H, m), 5.74 (2H, s), 4.51-4.44 (2H, m), 4.23-4.20 (1H, m), 3.76-3.61 (4H, m), 2.46 (3H, s), 1.94-1.89 (2H, m); (M+H)$^+$ 408; Anal. Calcd for $C_{16}H_{15}N_7O+2$ HCl+1.5H$_2$O: C, 45.62; H, 4.79; N, 23.27. Found: C, 45.63; H, 4.71; N, 23.14.

(R)-3-{6-(Tetrahydrofuran-3-yl)oxymethyl]pyridin-2-ylmethyl}-7-(5-methyl-2-furyl)-3H-[1,2,3]triazolo[4,5-d]pyrimidin-5-ylamine Prepared from 7-(5-methyl-2-furyl)-1H-[1,2,3]triazolo[4,5-d]pyrimidin-5-ylamine and (R)-2-bromomethyl-6-(tetrahydrofuran-3-yloxymethyl)pyridine by the alkylation method described for in Example 36.

mp: 169.7-170.6° C.; IR $v_{max}$ (DR)/cm$^{-1}$ 3514, 3294, 3171, 2940, 2867, 1632, 1574, 1540, 1496, 1457 and 1431; NMR $\delta_H$ (400 MHz, DMSO) 7.88 (1H, d, J 3.5 Hz), 7.78 (1H, t, J 8.0 Hz), 7.35 (1H, d, J 8.0 Hz), 7.27 (2H, br s), 7.05 (1H, d, J 8.0 Hz), 6.52-6.50 (1H, m), 5.74 (2H, s), 4.51-4.44 (2H, m), 4.23-4.20 (1H, m), 3.76-3.61 (4H, m), 2.46 (3H, s), 1.94-1.89 (2H, m); (M+H)$^+$ 408.

Example 1B

S-7-(5-methylfuran-2-yl)-3-(6-[tetrahydrofuran-3-yl]oxymethylpyrid-2-ylmethyl)-3H-[1,2,3]triazolo[4,5-d]pyrimidin-5-amine, alternate synthesis

2-Chloromethylpyridine

2-Chloromethylpyridine HCl (120 g, 0.732 mol, 1 eq) was dissolved in 500 mL demineralised water. Solid NaHCO$_3$ (67.60 g, 0.805 mol, 1.1 eq) was added in small portions and the mixture was stirred until gas evolution stopped. The free base was extracted into 2×800 mL ethyl acetate; the combined extracts were washed with 300 mL saturated brine and evaporated to give the title compound (90.43 g, 97%) as a red oil.

(S)-2-(Tetrahydrofuran-3-yloxymethyl)pyridine

A 3-neck flask under a nitrogen-line was charged with anhydrous THF (600 mL) through a canule. NaH (60% dispersion in mineral oil, 21.16 g, 0.529 mol, 1.5 eq) was suspended in the solvent under vigorous stirring. (S)-(+)-3-hydroxytetrahydrofuran (34.14 g, 0.388 moL, 1.1 eq) was added and stirred at room temperature for 30 minutes. 2-Chloromethylpyridine (1a; 45.00 g, 0.353 mol, 1 eq) was added neat and the mixture was stirred at reflux for 16 hours. The reaction mixture was cooled to room temperature and quenched with 520 mL saturated aqueous ammonium chloride solution. THF was removed under reduced pressure and the aqueous residue was extracted with 2×800 mL ethyl acetate. The combined organic extracts were washed with 250 mL saturated brine, dried over Na$_2$SO$_4$ and evaporated to dryness. The brown oily residue was taken up in 520 mL acetonitrile and remaining mineral oil was extracted with 330 mL hexane. Acetonitrile was evaporated in vacuo to leave a brown residue, yield 87%; LC-MS Retention time 1.22 min; (M+H)$^+$ 180.

(S)-2-(Tetrahydrofuran-3-yloxymethyl)pyridine-1-oxide (S)-2-(Tetrahydrofuran-3-yloxymethyl)pyridine (110.33 g, 0.616 mol, 1 eq) was dissolved in 900 mL DCM and cooled in an ice bath. 3-Chloroperoxybenzoic acid (151.77 g, 0.677 mol, 1.1 eq) was added and the solution was warmed to room temperature and stirred overnight. K$_2$CO$_3$ (85.09 g, 0.616 mol, 1 eq) was added as a solid and stirred for 2 hours. The white precipitate was filtered off and the filter cake washed with dichloromethane. Another portion of K$_2$CO$_3$ (85.09 g, 0.616 mol, 1 eq) was added to the filtrate and stirred for 3 days. The white solid was filtered off and the filtrate evaporated to give the title compound (119.62 g, 99%) as a yellow oil; LC-MS Retention time 1.27 min; (M+H)$^+$ 196.

(S)-6-(Tetrahydrofuran-3-yloxymethyl)pyridine-2-carbonitrile (S)-2-(Tetrahydrofuran-3-yloxymethyl)pyridine-1-oxide (24.08 g, 0.123 mol, 1 eq) was dissolved in anhydrous DCM (400 mL). N,N-Dimethylcarbamyl chloride (19.89 g, 0.185 mol, 1.5 eq) was added followed by trimethylsilyl cyanide (18.35 g, 0.185 mol, 1.5 eq). The solution was stirred at 40° C. for 24 hours (solution had turned red). The reaction was cooled to room temperature, then 2 M aqueous Na$_2$CO$_3$ solution was added (80 mL) and stirred overnight. The emulsion was filtered off, leaving the white precipitate behind. The layers were separated and the organic layer was evaporated to leave a brown oil. This was dissolved in ethyl acetate (160 mL), 2-M aqueous Na$_2$CO$_3$ solution (160 mL) was added and stirred for 2 hours. The layers were separated and the organic layer was washed with saturated brine (30 mL), dried over Na$_2$SO$_4$ and evaporated to a brown oil; LC-MS Retention time 1.82 min; (M+H)$^+$ 205.

(S)-6-(Tetrahydrofuran-3-yloxymethyl)-2-pyridinemethanamine (S)-6-(Tetrahydrofuran-3-yloxymethyl)pyridine-2-carbonitrile (0.206 mol, 1 eq) was added to borane (1-M in THF, 290 mL, 0.290 mol, 3 eq) at 0° C. under nitrogen. The reaction was then heated to reflux for 5 hours, cooled to room temperature and quenched with 100 mL methanol (exothermic) and evaporated. 2 M aqueous HCl (310 mL) was added (pH 1) to the combined residues. After the quench, the mixture was brought to pH 7 with 5 M NaOH (35 mL). The aqueous mixture was extracted with 2×500 mL dichloromethane. These organic extracts were discarded. The aqueous phase was brought to pH 14 with 5-N NaOH (100 mL) and extracted with 2×1000 mL DCM. The combined organic extracts (from alkaline solution) were washed with 100 mL saturated brine, dried over Na$_2$SO$_4$ and evaporated to give the title compound (50.70 g, 39% over 2 steps) as an amber oil; LC-MS Retention time 0.62 min; (M+H)$^+$ 205.

Example 2

7-(5-methylfuran-2-yl)-3-(6-[1-hydroxy-1-methylethyl]pyrid-2-ylmethyl)-3H-[1,2,3]triazolo[4,5-d]pyrimidin-5-amine Prepared from 7-(5-methyl-2-furyl)-1H-[1,2,3]triazolo[4,5-d]pyrimidine-5-amine and 2-(6-bromomethylpyridine-2-yl)propan-2-ol by the alkylation method described in Example 36.

IR $\nu_{max}$ (DR)/cm$^{-1}$ 3487, 3335, 3120, 2974, 2926, 1517, 1540, 1491 and 1418; NMR $\delta_H$ (400 MHz, DMSO) 7.88 (1H, d, J 3.5 Hz), 7.74 (1H, t, J 8.0 Hz), 7.54 (1H, d, J 8.0 Hz), 7.30 (2H, br s), 6.95 (1H, d, J 8.0 Hz), 6.52-6.51 (1H, m), 5.76 (2H, s), 5.15 (1H, s), 2.46 (3H, s), 1.27 (6H, s); (M+H)$^+$ 366.

Example 3

7-(5-methylfuran-2-yl)-3-(6-[1-hydroxy-1-cyclopentyl]pyrid-2-ylmethyl)-3H-[1,2,3]triazolo[4,5-d]pyrimidin-5-amine 2-(1-Hydroxy-1-cyclopentyl)pyridine Prepared from 2-bromopyridine and cyclopentanone by the method described in Example 10.

2-(1-Hydroxy-1-cyclopentyl)pyridine-N-oxide

Prepared from 2-(1-hydroxy-1-cyclopentyl)pyridine by the method described above for Example 10; NMR $\delta_H$ (400 MHz, CDCl$_3$) 1.68-1.78 (2H, m), 1.96-2.06 (4H, m), 2.26-2.35 (2H, m), 7.14 (1H, s), 7.24 (1H, dd, J 6.5 Hz, 2.0 Hz), 7.32-7.41 (2H, m), 8.26 (1H, dd, J 6.0 Hz, 1.0 Hz); (M+H)$^+$ 180.

6-(1-Hydroxy-1-cyclopentyl)pyridine-2-carbonitrile

Prepared from 2-(1-hydroxy-1-cyclopentyl)pyridine-N-oxide by the method described above for Example 10; NMR $\delta_H$ (400 MHz, CDCl$_3$) 1.74-1.94 (6H, m), 2.15-2.22 (2H, m), 7.49 (1H, dd, J 7.5 Hz, 1.5 Hz), 7.72-7.80 (2H, m)

6-(1-Hydroxy-1-cyclopentyl)pyridine-2-methanamine

Prepared from 6-(1-hydroxy-1-cyclopentyl)pyridine-2-carbonitrile by the method described in Example 10; NMR $\delta_H$ (400 MHz, CDCl$_3$) 1.48 (2H, s), 1.66-1.75 (2H, m), 1.78-1.92 (6H, m), 3.83 (2H, s), 5.12 (1H, s), 7.01 (1H, d, J 7.5 Hz), 7.08 (1H, d, J 8.0 Hz), 7.51 (1H, t, J 8.0 Hz); (M+H)$^+$ 194.

N-(2-amino-6-chloro-4-[6-(1-hydroxy-1-cyclopentyl)pyridine-2-methylamino]pyrimidin-5-yl)formamide Prepared from N-(2-amino-4,6-dichloropyrimidin-5-yl)formamide and 6-(1-hydroxy-1-cyclopentyl)pyridine-2-methanamine by the method described in Example 10 to give the title compound (0.256 g, 47%) as a cream powder; NMR $\delta_H$ (400 MHz, DMSO) 1.68-1.80 (4H, m), 1.81-1.92 (2H, m), 2.04-2.12 (2H, m), 4.56 (2H, d, J 5.5 Hz), 5.01 (1H, s), 6.45 (2H, s), 7.11 (1H, d, J 8.0 Hz), 7.34 (1H, t, J 6.0 Hz), 7.52 (1H, d, J 7.5 Hz), 7.69 (1H, t, J 7.5 Hz), 8.19 (1H, s), 9.21 (1H, s); (M+H)$^+$ 363.

7-Chloro-3-(6-[1-hydroxy-1-cyclopentyl]pyridine-2-ylmethyl)-3H-[1,2,3]triazolo[4,5-d]pyrimidin-2-amine Prepared from N-(2-amino-6-chloro-4-[6-(1-hydroxy-1-cyclopentyl)pyridine-2-methylamino]pyrimidin-5-yl)formamide by the method described in Example 10; NMR $\delta_H$ (400 MHz, DMSO) 1.44-1.51 (2H, m), 1.55-1.62 (2H, m), 1.67-1.76 (4H, m), 4.96 (1H, s), 5.78 (2H, s), 7.07 (1H, d, J 7.0 Hz), 7.54 (1H, d, J 8.5 Hz), 7.61 (2H, s), 7.73 (1H, t, J 7.5 Hz); (M+H)$^+$ 335.

3-(6-[1-hydroxy-1-cyclopentyl]pyridine-2-ylmethyl)-7-(5-methyl-2-furyl)-3H-[1,2,3]triazolo[4,5-d]pyrimidin-2-amine Prepared from 7-chloro-3-(6-[1-hydroxy-1-cyclopentyl]pyridine-2-ylmethyl)-3H-[1,2,3]triazolo[4,5-d]pyrimidin-2-amine by the method described in Example 10.

IR $\nu_{max}$ (DR)/cm$^{-1}$ 3325, 3203, 2959, 2871, 1537, 1504, 1433, 1325, 1206, 1107, 1026 and 794; NMR $\delta_H$ (400 MHz, DMSO) 1.47-1.55 (2H, m), 1.57-1.63 (2H, m), 1.67-1.76 (2H, m), 1.80-1.87 (2H, m), 2.46 (3H, s), 4.97 (1H, s), 5.76 (2H, s), 6.50 (1H, dd, J 3.5 Hz, 1.0 Hz), 6.98 (1H, d, J 7.5 Hz), 7.23 (2H, s), 7.55 (1H, d, J 7.5 Hz), 7.72 (1H, t, J 7.5 Hz), 7.87 (1H, d, J 3.0 Hz); (M+H)$^+$ 392.

Example 4

7-(5-methylfuran-2-yl)-3-(6-[1-hydroxy-1-cyclohexyl]pyrid-2-ylmethyl)-3H-[1,2,3]triazolo[4,5-d]pyrimidin-5-amine 1-(6-[tert-Butyldimethylsilyloxymethyl]pyridine-2-yl)-1-cyclohexanol Prepared from 6-bromo-O-(tert-butyldimethylsilyl)-2-pyridinemethanol and cyclohexanone by the method described in Example 10 to give the title compound (0.49 g, 15%) as a yellow oil; NMR $\delta_H$ (400 MHz, CDCl$_3$) 0.13 (6H, s), 0.96 (9H, s), 1.61-1.91 (10H, m), 4.82 (2H, s), 5.17 (1H, s), 7.21 (1H, dd, J 8.0 Hz, 1.0 Hz), 7.38 (1H, dd, J 7.5 Hz), 1.0 Hz), 7.71 (1H, t, J 7.5 Hz). TLC (Hex:EtOAc (9:1)) Rf=0.30**

6-(1-Hydroxy-1-cyclohexyl)-2-pyridinemethanol

Prepared from 1-(6-[tert-butyldimethylsilyloxymethyl]pyridine-2-yl)-1-cyclohexanol by the method described for the final step in Example 27 to give the title compound (0.35 g, quantitative) as a yellow oil; NMR $\delta_H$ (400 MHz, CDCl$_3$) 1.67-1.89 (10H, m), 3.73-3.77 (1H, m), 4.78 (2H, s), 7.17 (1H, d, J 7.5 Hz), 7.34 (1H, d, J 8.0 Hz), 7.71 (1H, t, J 7.5 Hz); (M+H)$^+$ 208.

1-(6-Bromomethylpyridine-2-yl)-1-cyclohexanol

Prepared from 6-(1-hydroxy-1-cyclohexyl)-2-pyridinemethanol by the bromination method described in Example 31 to give the title compound (0.30 g, 44%) as a yellow oil; NMR $\delta_H$ (400 MHz, CDCl$_3$) 1.62-1.89 (10H, m), 4.55 (2H, s), 4.89 (1H, s), 7.30 (1H, dd, J 8.0 Hz, 1.0 Hz), 7.34 (1H, dd, J 7.5 Hz, 1.0 Hz), 7.71 (1H, t, J 7.5 Hz); (M+H)$^+$ 270.

3-(6-[1-hydroxy-1-cyclohexyl]pyridine-2-ylmethyl)-7-(5-methyl-2-furyl)-3H-[1,2,3]triazolo[4,5-d]pyrimidin-2-amine Prepared from 7-(5-methyl-2-furyl)-1H-[1,2,3]triazolo[4,5-d]pyrimidin-5-ylamine and 1-(6-bromomethylpyridine-2-yl)-1-cyclohexanol by the alkylation method described in Example 36.

IR $\nu_{max}$ (DR)/cm$^{-1}$ 3321, 3205, 2931, 2857, 1604, 1573, 1537, 1503, 1433, 1326, 1206 and 794; NMR $\delta_H$ (400 MHz, DMSO) 0.81-0.87 (1H, m), 1.02-1.15 (1H, m), 1.33-1.43 (4H, m), 1.50-1.73 (4H, m), 2.46 (3H, s), 4.87 (1H, s), 5.76 (2H, s), 6.51 (1H, dd, J 3.5 Hz, 1.0 Hz), 6.95 (1H, d, J 7.5 Hz), 7.29 (2H, s), 7.53 (1H, d, J 8.0 Hz), 7.73 (1H, t, J 7.5 Hz), 7.88 (1H, d, J 3.5 Hz).

Example 5

7-(5-methylfuran-2-yl)-3-(6-[4-hydroxytetrahydropyran-4-yl]pyrid-2-ylmethyl)-3H-[1,2,3]triazolo[4,5-d]pyrimidin-5-amine Prepared as in Example 10 from 7-chloro-3-(6-[4-hydroxytetrahydropyran-4-yl]pyridine-2-ylmethyl)-3H-[1,2,3]triazolo[4,5-d]pyrimidin-2-amine and 5-methyl-2-furanboronic acid as described above to give the title compound.
IR $v_{max}$ (DR)/cm$^{-1}$ 3305, 3206, 2956, 1731, 1680, 1622, 1494, 1372, 1226, 1142, 1029 and 792; NMR $\delta_H$ (400 MHz, DMSO) 1.39 (2H, d, J 12.5 Hz), 2.09 (2H, dt, J 12.5 Hz), 2.45 (3H, s), 3.63-3.73 (4H, m), 5.28 (1H, s), 5.97 (2H, s), 6.49 (1H, d, J 3.5 Hz), 7.03 (2H, s), 7.11 (1H, d, J 7.5 Hz), 7.63 (1H, d, J 7.5 Hz), 7.70 (1H, d, J 3.5 Hz), 7.82 (1H, t, J 7.5 Hz); (M+H)$^+$ 408.

Example 6

7-(5-methylfuran-2-yl)-3-(6-[1-hydroxycyclobutyl]pyrid-2-ylmethyl)-3H-[1,2,3]triazolo[4,5-d]pyrimidin-5-amine 4-(6-[1-hydroxy-1-cyclobutyl]pyridine-2-methylamino)-6-(5-methyl-2-furyl)-5-nitropyrimidine-2-amine Prepared from 6-(5-methyl-2-furyl)-5-nitro-4-(p-toluenesulphonyloxy)pyrimidine-2-amine and 6-(1-hydroxy-1-cyclobutyl)pyridine-2-methanamine by the method described for Example 1 to give the title compound (0.14 g, 38%) as a yellow solid; NMR $\delta_H$ (400 MHz, DMSO) 8.90 (1H, br t), 7.75 (1H, t, J 7.7 Hz), 7.47 (1H, d, J 7.7 Hz), 7.34 (2H, br s), 7.21 (1H, d, J 7.7 Hz), 6.90 (1H, d, J 2.9 Hz), 6.27 (1H, d, J 2.9 Hz), 5.71 (1H, br s), 4.78 (2H, d, J 3.9 Hz), 2.59 (2H, m), 2.30 (3H, s), 2.20 (2H, m), 1.89 (2H, m); (M+H)$^+$ 397.

3-{6-[1-Hydroxy-1-cyclobutyl]pyridin-2-ylmethyl}-7-(5-methyl-2-furyl)-3H-[1,2,3]triazolo[4,5-d]pyrimidin-5-ylamine Prepared from 4-(6-[1-hydroxy-1-cyclobutyl]pyridine-2-methylamino)-6-(5-methyl-2-furyl)-5-nitropyrimidine-2-amine by the method described in Example 1 to give the title compound (0.05 g, 38%) as a beige solid.
NMR $\delta_H$ (400 MHz, DMSO) 1.36-1.44 (1H, m), 1.61-1.69 (1H, m), 2.03-2.10 (2H, m), 2.19-2.25 (2H, m), 2.46 (3H, s), 5.62 (1H, s), 5.81 (2H, s), 6.51 (1H, d, J 2.5 Hz), 7.08 (1H, d, J 7.5 Hz), 7.22 (2H, b), 7.44 (1H, d, J 8.0 Hz), 7.73 (1H, t, J 8.0 Hz), 7.87 (1H, d, J 3.5 Hz); (M+H)$^+$ 378.

Example 7

S-7-phenyl-3-(6-[tetrahydrofuran-3-yl]oxymethylpyrid-2-ylmethyl)-3H-[1,2,3]triazolo[4,5-d]pyrimidin-5-amine N-[2-Amino-4-chloro-6-({6-[(S)-(tetrahydro-furan-3-yl)oxymethyl]pyridin-2-ylmethyl}amino)pyrimidin-5-yl]formamide A mixture of N-(2-amino-4,6-dichloropyrimidin-5-yl)formamide (17.24 g, 82.46 mmol), 6-[(S)-(tetrahydrofuran-3-yl)oxymethyl]pyridin-2-ylmethylamine (18.89 g, 90.70 mmol) and triethylamine (12.64 mL, 90.70 mmol) in propan-2-ol (165 mL) was heated at reflux for 2 h, cooled and the resulting precipitate was filtered, washed with cold propan-2-ol and dried to give the title compound (22.66 g, 73%) as a pink solid; LC-MS retention time 1.46 min, (M+H)$^+$ 379.

6-chloro-N$^4$-{6-[(S)-(tetrahydrofuran-3-yl)oxymethyl]pyridin-2-ylmethyl}pyrimidine-2,4,5-triamine A mixture of N-[2-amino-4-chloro-6-({6-[(S)-(tetrahydrofuran-3-yl)oxymethyl]pyridin-2-ylmethyl}-amino)pyrimidin-5-yl]formamide (10.00 g, 26.40 mmol) and hydrochloric acid (6 M, 22 mL) in EtOH (100 mL) was heated at reflux for 15 h, cooled, basified with aqueous sodium hydroxide (5-M, 50 mL) and concentrated in vacuo to remove the EtOH. The resulting mixture was extracted with dichloromethane (×2) and the combined organic extracts were washed with saturated brine, dried (Na$_2$SO$_4$) and concentrated in vacuo to give the title compound (8.09 g, 87%) as a pink solid; LC-MS retention time 1.52 min; (M+H)$^+$ 351.

7-Chloro-3-{6-[(S)-(tetrahydrofuran-3-yl)oxymethyl]pyridin-2-ylmethyl}-3H-[1,2,3]triazolo[4,5-d]pyrimidin-5-ylamine A solution of 6-chloro-N$^4$-{6[(S)-(tetrahydrofuran-3-yl)oxymethyl]pyridin-2-ylmethyl}pyrimidine-2,4,5-triamine (8.09 g, 23.06 mmol) in EtOH (85 mL) and glacial acetic acid (21 mL) at 0° C., was treated with a solution of sodium nitrite (2.07 g, 29.979 mmol) in water (5.3 mL), stirred at 0° C. for 1 h and the resulting precipitate was filtered, washed with EtOH (85 mL) and dried to give the title compound (5.82 g, 70%) as an off-white solid; LC-MS retention time 1.94 min, (M+H)$^+$ 362.

7-Phenyl-3-[6-(tetrahydro-furan-3-yloxymethyl)pyridin-2-ylmethyl]-3H-[1,2,3]triazolo[4,5-d]pyrimidin-5-ylamine This was prepared from 7-chloro-3-{6-[(S)-(tetrahydrofuran-3-yl)oxymethyl]pyridin-2-ylmethyl}-3H-[1,2,3]triazolo[4,5-d]pyrimidin-5-ylamine and phenylboronic acid by the method of Example 13 to give 0.060 g (68%).
NMR $\delta_H$ (400 MHz, d$_6$-DMSO) 8.77-8.74 (2H, m), 7.79 (1H, t, J 8 Hz), 7.67-7.63 (3H, m), 7.35 (1H, d, J 8 Hz), 7.33 (2H, br s), 7.08 (1H, d, J 8 Hz), 5.79 (2H, s), 4.49-4.47 (2H, m), 4.23-4.20 (1H, m), 3.75-3.61 (4H, m) and 1.93-1.89 (2H, m); LC-MS Retention time 2.28 min; (M+H)$^+$ 404.

Example 8

7-phenyl-3-(6-[1-hydroxy-1-methylethyl]pyrid-2-ylmethyl)-3H-[1,2,3]triazolo[4,5-d]pyrimidin-5-amine Prepared as described in Example 20 from 7-chloro-3-(6-[1-hydroxy-1-methylethyl]pyridine-2-ylmethyl)-3H-[1,2,3]triazolo[4,5-d]pyrimidin-2-amine (0.25 g, 0.78 mml) and 3-phenylboronic acid (0.11 g, 0.93 mmol) to give the title compound (48 mg, 17%) as a white powder.
NMR $\delta_H$ (400 MHz, CDCl$_3$) 8.76 (2H, m), 7.73 (1H, t, J 7.7 Hz), 7.62 (3H, m), 7.55 (1H, d, J 4.3 Hz), 7.30 (2H, br s), 6.98 (1H, d, J 7.7 Hz), 5.80 (2H, s), 5.12 (1H, s), 1.26 (6H, s); LC-MS Retention time 2.26 min; (M+H)$^+$ 362.

Example 9

7-phenyl-3-(6-[1-hydroxy-1-cyclopentyl]pyrid-2-ylmethyl)-3H-[1,2,3]triazolo[4,5-d]pyrimidin-5-amine Prepared from 7-chloro-3-(6-[1-hydroxy-1-cyclopentyl]pyridine-2-ylmethyl)-3H-[1,2,3]triazolo[4,5-d]pyrimidin-2-amine by the method described in Example 10.

IR ν$_{max}$ (DR)/cm$^{-1}$ 3316, 3200, 2963, 1740, 1602, 1505, 1429, 1236, 1010 and 772. NMR δ$_H$ (400 MHz, DMSO) 1.41-1.51 (2H, m), 1.55-1.62 (2H, m), 1.64-1.73 (2H, m), 1.76-1.83 (2H, m), 4.96 (1H, s), 5.81 (2H, s), 7.02 (1H, d, J 7.5 Hz), 7.26 (2H, s), 7.55 (1H, d, J 8.0 Hz), 7.62-7.67 (3H, m), 7.73 (1H, t, J 7.5 Hz).

Example 10

7-phenyl-3-(6-[4-hydroxytetrahydropyran-4-yl]pyrid-2-ylmethyl)-3H-[1,2,3]triazolo[4,5-d]pyrimidin-5-amine 2-(4-Hydroxytetrahydropyran-4-yl)pyridine To a stirred, cooled solution of 2-bromopyridine (5 g, 31.65 mmol) in THF (75 mL) at −78° C. was added n-butyl lithium (2.5 M in hexanes, 12.66 mL, 31.65 mmol) dropwise and the solution stirred at −78° C. for 10 minutes. After this time, tetrahydro-4H-pyran-4-one (3.49 g, 34.81 mmol) was added, the reaction warmed to ambient temperature and stirred overnight. The reaction was then quenched with saturated aqueous ammonium chloride solution and the THF removed in vacuo. The resultant aqueous phase was twice extracted with ethyl acetate and the combined organic phases dried (magnesium sulfate) and filtered. After concentration in vacuo, purification by column chromatography (SiO$_2$, eluting with 2:1 hexanes:ethyl acetate) gave a residue which was triturated from hexane to yield the title compound (3.47 g, 61%) as a white solid; NMR δ$_H$ (400 MHz, CDCl$_3$) 8.49 (1H, m), 7.81 (1H, td, J 7.8 Hz, 1.8 Hz), 7.68 (1H, m), 7.25 (1H, ddd, J 7.5 Hz, 4.9 Hz, 1.1 Hz), 3.85 (4H, m), 3.30 (1H, m), 2.30 (2H, td, J 13.3 Hz, 5.3 Hz), 1.54 (1H, dd, J 13.8 Hz, 1.9 Hz); LC-MS Retention time 0.51 min, (M+H)$^+$ 180.

2-(4-Hydroxytetrahydropyran-4-yl)pyridine-N-oxide

To a stirred solution of 2-(4-hydroxytetrahydropyran-4-yl)pyridine (2.08 g, 11.6 mmol) in dichloromethane (100 mL) was added, with stirring, m-CPBA (77%, 2.86 g, 12.76 mmol) and the mixture stirred at ambient temperature overnight. After this time, potassium carbonate (1.62 g, 11.60 mmol) was added, the reaction stirred for two hours and the mixture filtered. A further aliquot of potassium carbonate (1.62 g, 11.60 mmol) was added to the filtrate and the mixture again stirred for two hours. After filtration and concentration in vacuo, the N-oxide was obtained as a pale brown solid (2.28 g, quant.) and used without further purification; NMR δ$_H$ (400 MHz, DMSO) 8.33 (1H, dd, J 6.3 Hz, 1.1 Hz), 7.65 (1H, dd, J 8.0 Hz, 2.0 Hz), 7.52 (1H, td, J 7.9 Hz, 1.3 Hz), 7.44 (1H, td, J 7.6 Hz, 2.0 Hz), 7.32 (1H, br s), 3.78 (4H, m), 2.23 (2H, td, J 12.5 Hz, 5.1 Hz), 1.80 (1H, d, J 11.4 Hz); LC-MS Retention time 0.99 min, (M+H)$^+$ 196.

6-(4-Hydroxytetrahydropyran-4-yl)pyridine-2-carbonitrile

To a stirred solution of 2-(4-hydroxytetrahydropyran-4-yl)pyridine-N-oxide (3.69 g, 18.91 mmol) in anhydrous dichloromethane was added dimethylcarbamoyl chloride (3.05 g, 28.4 mmol) and trimethylsilylcyanide (2.82 g, 28.4 mmol). The mixture was stirred for sixty hours at 40° C., after which time further aliquots of dimethyl carbamoyl chloride (3.05 g, 28.4 mmol) and trimethylsilylcyanide (2.82 g, 28.4 mmol) were added. After stirring at 40° C. for a further 24 hours, sodium carbonate solution (50 mL, 2 M aqueous solution) was added and the mixture stirred overnight. The resultant mixture was filtered and the layers partitioned. Sodium carbonate solution (50 mL, 2 M aqueous solution) was again added to the organic phase and stirred overnight. After separation of the phases, the organic layer was blown down at ambient temperature to give the title compound as a brown oil which was used in the next step without further purification; LC-MS Retention time 1.62 min, (M+H)$^+$ 205.

6-(4-Hydroxytetrahydropyran-4-yl)pyridine-2-methanamine 6-(4-Hydroxytetrahydropyran-4-yl)pyridine-2-carbonitrile (ca. 18.9 mmol) was dissolved in anhydrous THF (80 mL) and a 1 M solution of BH$_3$ in THF (95 mL, 95 mmol) added. The solution was stirred at ambient temperature for 2.5 hours, then quenched with methanol. The solution was adjusted to pH 1 by addition of 2 N hydrochloric acid solution and then neutralised to pH 5 with a 5 N solution of sodium hydroxide. Extraction with dichloromethane was followed by addition of further 2 N sodium hydroxide to the aqueous phase until the pH reached 14. This phase was twice extracted with dichloromethane and these combined extracts were evaporated to give a yellow gum. The aqueous extracts were acidified with 2 N hydrochloric acid and concentrated to dryness to yield a white residue. Three triturations of this residue with methanol and concentration of the methanolic liquors yielded a second crop of yellow gum. Drying in vacuo gave the title compound (2.51 g, 64%) as a foamy yellow solid; NMR δ$_H$ (400 MHz, DMSO) 8.53 (1H, br s), 7.85 (1H, t, J 7.8 Hz), 7.62 (1H, d, J 7.8 Hz), 7.34 (1H, d, J 7.5 Hz), 5.75 (1H, s), 3.72 (4H, m), 3.16 (2H, s), 2.29 (2H, m), 1.42 (1H, d, J 12.3 Hz); LC-MS Retention time 0.43 min, (M+H)$^+$ 209.

7-Chloro-3-(6-[4-hydroxytetrahydropyran-4-yl]pyridine-2-ylmethyl)-3H-[1,2,3]triazolo[4,5-d]pyrimidin-2-amine Prepared from 2-amino-4,6-dichloro-5-formylaminopyrimidine (1.77 g, 8.55 mmol) and 6-(4-hydroxytetrahydropyran-4-yl)pyridine-2-methanamine (1.96 g, 9.71 mmol) by the method described in reference example 1 to give the title compound (0.42 g, 14%) as a brown powder; NMR δ$_H$ (400 MHz, DMSO) 7.77 (1H, t, J 7.7 Hz), 7.65 (2H, br s), 7.56 (1H, d, J 7.5 Hz), 7.07 (1H, d, J 7.7 Hz), 5.77 (2H, s), 5.19 (1H, s), 3.63 (4H, m), 1.90 (2H, m), 1.31 (2H, d, J 11.9 Hz); LC-MS Retention time 1.83 min, (M+H)$^+$ 362.

3-(6-[4-Hydroxytetrahydropyran-4-yl]pyridine-2-ylmethyl)-7-phenyl-3H-[1,2,3]triazolo[4,5-d]pyrimidin-2-amine A solution of the 7-chloro-3-(6-[4-hydroxytetrahydropyran-4-yl]pyridine-2-ylmethyl)-3H-[1,2,3]triazolo[4,5-d]pyrimidin-2-amine (0.10 g, 0.27 mmol) and phenylboronic acid (0.05 g, 0.41 mmol) and potassium phosphate (0.12 g, 0.55 mmol) in 1,4-dioxane (5 mL) was degassed by sparging with nitrogen. Tetrakis triphenylphosphine palladium (16 mg) was then added, the solution degassed again and the resultant mixture heated at 100° C. for seven hours. The mixture was then concentrated onto Isolute-HM in vacuo, purified by column chromatography (silica, eluting with 3:1 ethyl acetate:hexane and neat ethyl acetate) and triturated with diethyl ether to give the title compound (41 mg, 37%) as a pale beige solid.

NMR $\delta_H$ (400 MHz, DMSO) 8.76 (2H, m), 7.77 (1H, t, J 7.8 Hz), 7.64 (3H, m), 7.57 (1H, d, J 7.5 Hz), 7.31 (2H, br s), 7.02 (1H, d, J 7.5 Hz), 5.81 (2H, s), 5.20 (1H, s), 3.60 (4H, m), 1.97 (2H, m), 1.33 (2H, d, J 12.0 Hz); LC-MS Retention time 2.17 min; (M+H)$^+$ 404.

Example 11

7-phenyl-3-(6-[1-hydroxycyclobutyl]pyrid-2-ylmethyl)-3H-[1,2,3]triazolo[4,5-d]pyrimidin-5-amine 2-(1-Hydroxy-1-cyclobutyl)pyridine Prepared from 2-bromopyridine and cyclobutanone by the method described in Example 10 to give the title compound (7.62 g, quantitative) as an orange oil; NMR $\delta_H$ (400 MHz, DMSO) 8.54 (1H, m), 7.75 (1H, td, J 7.6, 1.7 Hz), 7.59 (1H, m), 7.22 (1H, m), 5.70 (1H, s), 2.58 (2H, m), 2.23 (2H, m), 1.91 (2H, m); (M+H)$^+$ 151.

2-(1-Hydroxy-1-cyclobutyl)pyridine-N-oxide

Prepared from 2-(1-hydroxy-1-cyclobutyl)pyridine by the method described in Example 10 to give the title compound as a yellow oil; NMR $\delta_H$ (400 MHz, DMSO) 8.36 (1H, dd, J 6.3, 1.1 Hz), 8.31 (1H, s), 7.67 (1H, dd, J 8.1, 2.1 Hz), 7.50 (1H, td, J 8.7, 1.1 Hz), 7.44 (1H, m), 6.84 (1H, s), 2.51 (2H, m), 2.27 (2H, m), 1.94 (2H, m); (M+H)$^+$ 167.

6-(1-Hydroxy-1-cyclobutyl)pyridine-2-carbonitrile

Prepared from 2-(1-hydroxy-1-cyclobutyl)pyridine-N-oxide by the method described in Example 10 to give the title compound (1.66 g, 21%); NMR $\delta_H$ (400 MHz, DMSO) 8.02 (1H, app t, J 8.0 Hz), 7.89 (1H, d, J 2.7 Hz), 7.87 (1H, dd, J 3.0, 0.9 Hz), 5.96 (1H, s), 2.54 (2H, m), 2.25 (2H, m), 1.94 (1H, m), 1.79 (1H, m); (M+H)$^+$ 177.

6-(1-Hydroxy-1-cyclobutyl)pyridine-2-methanamine

Prepared from 6-(1-hydroxy-1-cyclobutyl)pyridine-2-carbonitrile by the method described in Example 10 to give the title compound (0.87 g, 53%) as a yellow oil; NMR $\delta_H$ (400 MHz, DMSO) 7.68 (1H, t, J 7.8 Hz), 7.40 (1H, d, J 7.6 Hz), 7.25 (1H, d, J 7.6 Hz), 5.73 (1H, s), 3.82 (2H, s), 2.55 (2H, m), 2.22 (2H, m), 1.83 (2H, m); (M+H)$^+$ 181.

N-(2-amino-6-chloro-4-[6-(1-hydroxy-1-cyclobutyl)pyridine-2-methylamino]pyrimidin-5-yl)formamide Prepared from N-(2-amino-4,6-dichloropyrimidin-5-yl)formamide and 6-(1-hydroxy-1-cyclobutyl)pyridine-2-methanamine by the method described in Example 7 to give the title compound (0.92 g, 85%) as an orange solid; NMR $\delta_H$ (400 MHz, DMSO) 9.77 (1H, s), 9.22 (1H, s), 7.70 (1H, t, J 7.7 Hz), 7.65 (2H, br s), 7.57 (1H, d, J 9.7 Hz), 7.37 (1H, t, J 5.7 Hz), 7.14 (1H, d, J 7.7 Hz), 5.66 (1H, s), 5.40 (2H, d, J 5.7 Hz), 2.52 (2H, m), 2.19 (2H, m), 1.90 (1H, m), 1.81 (1H, m); (M+H)$^+$ 350.

7-Chloro-3-{6-[1-hydroxy-1-cyclobutyl]pyridin-2-ylmethyl}-3H-[1,2,3]triazolo[4,5-d]pyrimidin-5-ylamine Prepared from N-(2-amino-6-chloro-4-[6-(1-hydroxy-1-cyclobutyl)pyridine-2-methylamino]pyrimidin-5-yl)formamide by the method described in Example 7 to give the title compound (0.12 g, 66%) as an orange solid; NMR $\delta_H$ (400 MHz, DMSO) 7.74 (1H, t, J 7.8 Hz), 7.60 (2H, br s), 7.43 (1H, d, J 7.8 Hz), 7.15 (1H, d, J 7.6 Hz), 5.83 (2H, s), 5.62 (1H, s), 2.12 (2H, m), 2.04 (2H, m), 1.64 (1H, m), 1.29 (1H, m); (M+H)$^+$ 332.

3-{6-[1-Hydroxy-1-cyclobutyl]pyridin-2-ylmethyl}-7-phenyl-3H-[1,2,3]triazolo[4,5-d]pyrimidin-5-ylamine Prepared from 7-chloro-3-{6-[1-hydroxy-1-cyclobutyl]pyridin-2-ylmethyl}-3H-[1,2,3]triazolo[4,5-d]pyrimidin-5-ylamine and phenylboronic acid by the method described in Example 7 to give the title compound (0.03 g).

NMR $\delta_H$ (400 MHz, DMSO) 1.32-1.39 (1H, m), 1.59-1.66 (1H, m), 2.01-2.09 (2H, m), 2.18-2.24 (2H, m), 5.62 (1H, s), 5.87 (2H, s), 7.10 (1H, d, J 8.0 Hz), 7.25 (2H, b), 7.43 (1H, d, J 8.0 Hz), 7.62-7.66 (3H, m), 7.74 (1H, t, J 7.5 Hz), 8.74-8.77 (2H, m); (M+H)$^+$ 374.

Example 12

7-phenyl-3-(6-[methoxymethyl]pyrid-2-ylmethyl)-3H-[1,2,3]triazolo[4,5-d]pyrimidin-5-amine The title compound was prepared from 7-chloro-3-(6-methoxymethylpyridin-2-ylmethyl)-3H-[1,2,3]triazolo[4,5-d]pyrimidin-5-amine and the appropriate arylboronic acid by the method described in reference example 1.

NMR $\delta_H$ (400 MHz, DMSO) 8.75 (2H, m), 8.35 (2H, br s), 7.78 (1H, t, J 6.9 Hz), 7.64 (2H, m), 7.34 (2H, br s), 7.04 (1H, d, J 7.6 Hz), 5.78 (2H, s), 4.43 (2H, s), 3.37 (3H, s); LC-MS Retention time 2.25 min; (M+H)$^+$ 348.

Example 13

S-7-(3-methoxyphenyl)-3-(6-[tetrahydrofuran-3-yl]oxymethylpyrid-2-ylmethyl)-3H-[1,2,3]triazolo[4,5-d]pyrimidin-5-amine A solution of 7-chloro-3-{6-[(S)-(tetrahydrofuran-3-yl)oxymethyl]pyridin-2-ylmethyl}-3H-[1,2,3]triazolo[4,5-d]pyrimidin-5-ylamine (0.100 g, 0.276 mmol) and 3-methoxyphenylboronic acid (0.084 g, 0.55 mmol) in 1,4-dioxane (4 mL) and saturated brine (1 mL) was degassed with nitrogen, treated with tetrakis(triphenylphosphine)palladium(0) (0.016 g, 0.014 mmol), heated at 90° C. for 6.5 h then partitioned between water and EtOAc. The organic phase was separated and the aqueous phase was re-extracted with EtOAc, the combined organic extract was dried (Na$_2$SO$_4$), concentrated in vacuo and the resulting brown solid (0.150 g) purified by semi-preparative LC-MS to give the title compound (0.052 g, 43%) as an off-white solid.

NMR $\delta_H$ (400 MHz, d$_6$-DMSO) 8.39 (1H, dt, J 7.5, 1 Hz), 8.30 (1H, dd, J 2.5, 0.5 Hz), 7.79 (1H, t, J 7.5 Hz), 7.65-7.53 (3H, m), 7.37 (2H, br s), 7.24 (1H, ddd, J 8.5, 2.5, 1 Hz), 7.09 (1H, d, J 7.5 Hz), 5.78 (2H, S), 4.47 (2H, s), 4.23-4.19 (1H, m), 3.88 (3H, s), 3.76-3.60 (4H, m) and 1.93-1.88 (2H, m); LC-MS Retention time 2.32 (M+H)$^+$ 434.

Example 14

7-(3-methoxyphenyl)-3-(6-[1-hydroxy-1-methylethyl]pyrid-2-ylmethyl)-3H-[1,2,3]triazolo[4,5-d]pyrimidin-5-amine 2-Bromomethyl-6-(1-hydroxy-1-methylethyl)pyridine To a solution of 2-hydroxymethyl-6-(1-hydroxy-1-methylethyl)pyridine (5.1 g, 30.5 mmol) in dicholoromethane (300 mL) was added carbon tetrabromide (8.81 g, 33.6 mmol) and triphenylphosphine (11.14 g, 33.6 mmol). The reaction was stirred at ambient temperature overnight then poured into a saturated solution of sodium bicarbonate. The organic layer was separated, concentrated to dryness and purified by column chromatography, eluting with a gradient of hexane to 3:1 hexane:ethyl acetate. The title compound (5.21 g, 74%) was obtained as a colourless oil; LC-MS Retention time 2.08 min, (M+H)$^+$ 230, 232

2-Azidomethyl-6-(1-hydroxy-1-methylethyl)pyridine

2-Bromomethyl-6-(1-hydroxy-1-methylethyl)pyridine (7.61.g, 33 mmol) was dissolved in dimethylformamide (100 mL) and sodium azide (2.6 g, 39.7 mmol) added. After stirring the resultant mixture overnight at ambient temperature, the reaction was poured into dicholoromethane and washed well with water. The organic layer was dried (magnesium sulphate), filtered and concentrated to dryness. The resulting yellow oil (5.88 g, 93%) was used without further purification; NMR $\delta_H$ (400 MHz, CDCl$_3$) 7.70 (1H, t, J 7.8 Hz), 7.30 (1H, d, J 8.0 Hz), 7.19 (1H, d, J 7.8 Hz), 4.82 (1H, br s), 4.42 (2H, s), 1.51 (6H, s); LC-MS Retention time 2.06 min, (M+H)$^+$ 193.

6-(1-Hydroxy-1-methylethyl)pyridine-2-methanamine

2-Azidomethyl-6-(1-hydroxy-1-methylethyl)pyridine (5.88 g, 30.6 mmol) was dissolved in methanol (100 mL) and palladium (5% w/w on carbon) added. The suspension was gently agitated under a hydrogen atmosphere overnight, filtered though celite and concentrated to dryness to give 4.61 g (90%) of the amine as a colorless oil; NMR $\delta_H$ (400 MHz, CDCl$_3$) 7.63 (1H, t, J 7.8 Hz), 7.19 (1H, d, J 7.8 Hz), 7.12 (1H, d, J 7.6 Hz), 3.93 (2H, s), 1.49 (6H, s); LC-MS Retention time 0.42 min, (M+H)$^+$ 167.

7-Chloro-3-(6-[1-hydroxy-1-methylethyl]pyridine-2-ylmethyl)-3H-[1,2,3]triazolo[4,5-d]pyrimidin-2-amine A solution of the 6-(1-hydroxy-1-methylethyl)pyridine-2-methanamine (2.5 g, 15.0 mmol), 2-amino-4,6-dichloro-5-formylaminopyrimidine (3.12 g, 15.0 mmol) and trietheylamine (4.2 mL, 30 mmol) in isopropyl alcohol (35 mL) was heated at 90° C. for four hours, then cooled to 0° C. and poured into iced water. This mixture was filtered and the liquors concentrated to dryness. The resultant solids were re-dissolved in ethanol (35 mL) and concentrated hydrochloric acid (12 M, 2.5 mL, 30 mmol) added. This mixture was then heated at 90° C. for two hours before again cooling to 0° C. A solution of sodium nitrite (1.24 g, 18 mmol) in water (2.5 mL) was added dropwise and the mixture stirred at 0° C. for 30 minutes. After pouring into iced, saturated sodium bicarbonate solution and removal of the residual ethanol in vacuo followed by filtration and drying in vacuo, the title compound (2.25 g, 47%) was obtained as a red/brown powder; NMR $\delta_H$ (400 MHz, CDCl$_3$) 7.66 (1H, t, J 7.7 Hz), 7.28 (1H, d, J 7.8 Hz), 7.02 (1H, d, J 7.7 Hz), 5.77 (2H, d), 5.45 (2H, br s), 1.47 (6H, s); LC-MS Retention time 1.89 min, (M+H)$^+$ 320.

3-(6-[1-Hydroxy-1-methylethyl]pyridin-2-ylmethyl)-7-(3-methoxyphenyl)-3H-[1,2,3]triazolo[4,5-d]pyrimidin-2-amine Prepared as described in Example 20 from 7-chloro-3-(6-[1-hydroxy-1-methylethyl]pyridine-2-ylmethyl)-3H-[1,2,3]triazolo[4,5-d]pyrimidin-2-amine and 3-methoxyphenylboronic acid (0.08 g, 0.56 mmol) to give the title compound (68 mg, 37%) as a yellow solid.
NMR $\delta_H$ (400 MHz, CDCl$_3$) 8.49 (1H, d, J 7.7 Hz), 8.38 (1H, br s), 7.64 (1H, t, 8.0 Hz), 7.47 (1H, t, J 8.0 Hz), 7.27 (1H, d, J 7.9 Hz), 7.13 (1H, dd, J 7.9 Hz, 3.4 Hz), 6.99 (1H, d, J 7.7 Hz) 5.84 (2H, s), 5.45 (2H, br s), 3.93 (2H, s), 1.49 (6H, s); LC-MS Retention time 2.27 min; (M+H)$^+$ 392.

Example 15

7-(3-methoxyphenyl)-3-(6-[1-hydroxy-1-cyclopentyl]pyrid-2-ylmethyl)-3H-[1,2,3]triazolo[4,5-d]pyrimidin-5-amine Prepared from 7-chloro-3-(6-[1-hydroxy-1-cyclopentyl]pyridine-2-ylmethyl)-3H-[1,2,3]triazolo[4,5-c]pyrimidin-2-amine by the method described above in Example 10.
IR $v_{max}$ (DR)/cm$^{-1}$ 3375, 3187, 2954, 1602, 1522, 1219, 1017 and 793; NMR $\delta_H$ (400 MHz, DMSO) 1.42-1.52 (2H, m), 1.57-1.84 (6H, m), 3.88 (3H, s), 4.96 (1H, s), 5.81 (2H, s), 7.02 (1H, d, J 7.5 Hz), 7.22-7.28 (3H, m), 7.54-7.58 (2H, m), 7.73 (1H, t, J 8.0 Hz), 8.29-8.30 (1H, m), 8.38 (1H, dt, J 8.0, 1.5 Hz); (M+H)$^+$ 418.

Example 16

7-(3-methoxyphenyl)-3-(6-[4-hydroxytetrahydropyran-4-yl]pyrid-2-ylmethyl)-3H-[1,2,3]triazolo[4,5-d]pyrimidin-5-amine Prepared from 7-chloro-3-(6-[4-hydroxytetrahydropyran-4-yl]pyridine-2-ylmethyl)-3H-[1,2,3]triazolo[4,5-d]pyrimidin-2-amine and 3-methoxyphenylboronic acid (0.08 g, 0.55 mmol) as described in Example 10 to give the title compound (45 mg, 38%) as a solid.
NMR $\delta_H$ (400 MHz, DMSO) 8.40 (1H, dt, J 7.9, 1.1 Hz), 8.30 (1H, m), 7.77 (1H, t, J 7.8 Hz), 7.56 (2H, t, J 8.1 Hz), 7.31 (2H, br s), 7.24 (1H, m), 7.02 (1H, d, J 7.2 Hz), 5.81 (2H, s), 5.43 (1H, s), 3.69 (3H, s), 3.58 (4H, m), 3.41 (2H, m), 1.33 (2H, d, J 12.2 Hz); LC-MS Retention time 2.18 min; (M+H)$^+$ 434.

Example 17

7-(3-methoxyphenyl)-3-(6-[1-hydroxycyclobutyl]pyrid-2-ylmethyl)-3H-[1,2,3]triazolo[4,5-d]pyrimidin-5-amine Prepared from 7-chloro-3-{6-[1-hydroxy-1-cyclobutyl]pyridin-2-ylmethyl}-3H-[1,2,3]triazolo[4,5-d]pyrimidin-5- ylamine and 3-methoxyphenylboronic acid by the method described in Example 7 to give the title compound (0.04 g, 16%).

NMR $\delta_H$ (400 MHz, DMSO) 1.32-1.38 (1H, m), 1.57-1.66 (1H, m), 2.01-2.09 (2H, m), 2.17-2.24 (2H, m), 3.88 (3H, s), 5.63 (1H, s), 5.86 (2H, s), 7.10 (1H, d, J 7.5 Hz), 7.22-7.30 (3H, m), 7.43 (1H, d, J 7.5 Hz), 7.56 (1H, t, J 8.0 Hz), 7.74 (1H, t, J 7.5 Hz), 8.30 (1H, s), 8.40 (1H, d, J 7.5 Hz); (M+H)+ 404.

Example 18

7-(3-methoxyphenyl)-3-(6-[methoxymethyl]pyrid-2-ylmethyl)-3H-[1,2,3]triazolo[4,5-d]pyrimidin-5-amine The title compound was prepared from 7-chloro-3-(6-methoxymethylpyridin-2-ylmethyl)-3H-[1,2,3]triazolo[4,5-d]pyrimidin-5-amine and the appropriate arylboronic acid by the method described in reference example 1.

Example 19

S-7-(3-cyanophenyl)-3-(6-[tetrahydrofuran-3-yl]oxymethylpyrid-2-ylmethyl)-3H-[1,2,3]triazolo[4,5-d]pyrimidin-5-amine This was prepared from 7-chloro-3-{6-[(S)-(tetrahydrofuran-3-yl)oxymethyl]pyridin-2-ylmethyl}-3H-[1,2,3]triazolo[4,5-d]pyrimidin-5-ylamine and 3-cyanophenylboronic acid by the method of Example 13 to give 0.039 g (33%).

NMR $\delta_H$ (400 MHz, d$_6$-DMSO) 9.04 (1H, s), 8.14 (1H, d, J 8.0 Hz), 7.89 (1H, t, J 8.0 Hz), 7.80 (1H, t, 7.5 Hz), 7.50 (2H, br s), 7.36 (1H, d, J 7.5 Hz), 7.09 (1H, d, J 7.5 Hz), 5.81 (2H, s), 4.47 (2H, s), 4.25-4.18 (1H, m), 3.75-3.60 (4H, m) and 1.93-1.90 (2H, m); LC-MS Retention time 2.29 min; (M+H)+ 429.

Example 20

7-(3-cyanophenyl)-3-(6-[1-hydroxy-1-methylethyl]pyrid-2-ylmethyl)-3H-[1,2,3]triazolo[4,5-d]pyrimidin-5-amine A solution of the 7-chloro-3-(6-[1-hydroxy-1-methylethyl]pyridine-2-ylmethyl)-3H-[1,2,3]triazolo[4,5-d]pyrimidin-2-amine (0.15 g, 0.47 mmol) and 3-cyanophenylboronic acid (0.08 g, 0.56 mmol) in THF (5 mL) and saturated sodium bicarbonate solution (0.8 mL) was degassed under three alternating cycles of vacuum and nitrogen. Tetrakis triphenylphosphine palladium (50 mg) was then added, the solution degassed again and the resultant mixture heated at 70° C. overnight. The mixture was cooled to ambient temperature and loaded directly onto a pre-packed 20 g silica column. This was eluted using a gradient of dichloromethane to dichloromethane:methanol 95:5 to give a yellow waxy oil which was further purified by preparative HPLC to give the title compound (15 mg, 8%) as a yellow powder.

NMR $\delta_H$ (400 MHz, CDCl$_3$) 9.17 (1H, dt, J 8.1, 1.4 Hz), 9.11 (1H, br s), 7.83 (1H, dt, J 7.8, 1.3 Hz), 7.66 (2H, m), 7.28 (1H, d, J 7.8 Hz), 7.04 (1H, d, J 7.8 Hz), 5.86 (2H, s), 5.40 (2H, br s), 1.48 (6H, s); LC-MS Retention time 2.25 min; (M+H)+ 387.

Example 21

7-(3-cyanophenyl)-3-(6-[1-hydroxy-1-cyclopentyl]pyrid-2-ylmethyl)-3H-[1,2,3]triazolo[4,5-d]pyrimidin-5-amine Prepared from 7-chloro-3-(6-[1-hydroxy-1-cyclopentyl]pyridine-2-ylmethyl)-3H-[1,2,3]triazolo[4,5-d]pyrimidin-2-amine by the method described in Example 10.

IR $\nu_{max}$ (DR)/cm$^{-1}$ 3323, 2967, 2232, 1732, 1595, 1507, 1436, 1234, 1012 and 794; NMR $\delta_H$ (400 MHz, DMSO) 1.40-1.48 (2H, m), 1.55-1.81 (6H, m), 4.96 (1H, s), 5.83 (2H, s), 7.04 (1H, d, J 7.5 Hz), 7.40 (2H, s), 7.55 (1H, d, J 7.0 Hz), 7.73 (1H, t, J 7.5 Hz), 7.90 (1H, t, J 8.0 Hz), 8.14 (1H, dt, J 8.0, 1.5 Hz), 9.02-9.07 (2H, m); (M+H)+ 413.

Example 22

7-(3-cyanophenyl)-3-(6-[4-hydroxytetrahydropyran-4-yl]pyrid-2-ylmethyl)-3H-[1,2,3]triazolo[4,5-d]pyrimidin-5-amine Prepared as described in Example 10 from 7-chloro-3-(6-[4-hydroxytetrahydropyran-4-yl]pyridine-2-ylmethyl)-3H-[1,2,3]triazolo[4,5-d]pyrimidin-2-amine and 3-cyanophenylboronic acid (0.09 g, 0.66 mmol) to give the title compound (28 mg, 20%) as a yellow solid.

NMR $\delta_H$ (400 MHz, CDCl$_3$) 9.06 (2H, m), 8.13 (1H, dt, J 7.8, 1.3 Hz), 7.89 (1H, t, J 7.9 Hz), 7.78 (1H, t, J 7.8 Hz), 7.57 (1H, d, J 7.8 Hz), 7.45 (2H br s), 7.05 (1H, d, J 7.6 Hz), 5.83 (2H, s), 5.20 (1H, s), 3.63 (4H, m), 1.95 (2H, td, J 11.4, 4.5 Hz), 1.33 (1H, d, J 12.4 Hz); LC-MS Retention time 2.16 min; (M+H)+ 429.

Example 23

7-(3-cyanophenyl)-3-(6-[1-hydroxycyclobutyl]pyrid-2-ylmethyl)-3H-[1,2,3]triazolo[4,5-d]pyrimidin-5-amine Prepared from 7-chloro-3-{6-[1-hydroxy-1-cyclobutyl]pyridin-2-ylmethyl}-3H-[1,2,3]triazolo[4,5-d]pyrimidin-5-ylamine and 3-cyanophenylboronic acid by the method described for Example 7 to give the title compound (0.06 g) as a white powder.

NMR $\delta_H$ (400 MHz, DMSO) 1.31-1.39 (1H, m), 1.60-1.66 (1H, m), 2.04-2.08 (2H, m), 2.17-2.26 (2H, m), 5.62 (1H, s), 5.89 (2H, s), 7.15 (1H, d, J 7.5 Hz), 7.40-7.51 (3H, m), 7.75 (1H, t, J 8.0 Hz), 7.90 (1H, t, J 7.5 Hz), 8.15 (1H, d, J 7.5 Hz), 9.04-9.12 (2H, m); (M+H)+ 399.

Example 24

7-(3-cyanophenyl)-3-(6-[methoxymethyl]pyrid-2-ylmethyl)-3H-[1,2,3]triazolo[4,5-d]pyrimidin-5-amine The title compound was prepared from 7-chloro-3-(6-methoxymethylpyridin-2-ylmethyl)-3H-[1,2,3]triazolo[4,5-d]pyrimidin-5-amine and the appropriate arylboronic acid by the method described in reference example 1.

Example 25

S-7-(4-methylthiazol-2-yl)-3-(6-[tetrahydrofuran-3-yl]oxymethylpyrid-2-ylmethyl)-3H-[1,2,3]triazolo[4,5-d]pyrimidin-5-amine This was prepared from 7-chloro-3-{6-[(S)-(tetrahydrofuran-3-yl)oxymethyl]pyridin-2-ylmethyl}-3H-[1,2,3]triazolo[4,5-d]pyrimidin-5-ylamine and 4-methylthiazole by the method of Example 38.

Example 26

7-(4-methylthiazol-2-yl)-3-(6-[1-hydroxy-1-methylethyl]pyrid-2-ylmethyl)-3H-[1,2,3]triazolo[4,5-d]pyrimidin-5-amine This is prepared from 7-chloro-3-(6-[1-hydroxy-1-methylethyl]pyrid-2-ylmethyl)-3H-[1,2,3]triazolo[4,5-d]pyrimidin-5-amine and 4-methylthiazole by the method of Example 38.

Example 27

7-(4-methylthiazol-2-yl)-3-(6-[1-hydroxy-1-cyclopentyl]pyrid-2-ylmethyl)-3H-[1,2,3]triazolo[4,5-d]pyrimidin-5-amine 7-Chloro-3-{6-[1-trimethylsilyloxy-1-cyclopentyl]pyridin-2-ylmethyl}-3H-[1,2,3]triazolo[4,5-d]pyrimidin-2-ylamine A solution of 7-chloro-3-{6-[1-hydroxy-1-cyclopentyl]pyridin-2-ylmethyl}-3H-[1,2,3]triazolo[4,5-d]pyrimidin-5-ylamine (0.5 g, 1.5 mmol) in dry THF (15 mL) at room temperature was treated with trimethylsilyl chloride (0.38 mL, 3.0 mmol) then triethylamine (0.42 mL, 3.0 mmol); stirred at 35° C. overnight, treated with additional quantities of trimethylsilyl chloride (0.19 mL, 1.5 mmol) then triethylamine (0.21 mL, 1.5 mmol) and stirred at 35° C. for 24 h. The mixture was poured into water (60 mL), extracted with EtOAc (×2), concentrated in vacuo and purified by chromatography (SiO$_2$:isohexane-EtOAc (3:1)) to give the title compound (0.55 g, 88%); NMR $\delta_H$ (400 MHz, DMSO) 7.78 (1H, t, J 7.8 Hz), 7.59 (2H, br s), 7.43 (1H, d, J 7.8 Hz), 7.19 (1H, d, J 7.8 Hz), 5.79 (2H, s), 1.68 (7H, m), 1.40 (2H, m), −0.11 (9H, s); (M+H)$^+$ 418.

7-(4-Methylthiazol-2-yl)-3-{6-[1-trimethylsilyloxy-1-cyclopentyl]pyridin-2-ylmethyl}-3H-[1,2,3]triazolo[4,5-d]pyrimidin-5-ylamine Prepared from 7-chloro-3-{6-[1-trimethylsilyloxy-1-cyclopentyl]pyridin-2-ylmethyl}-3H-[1,2,3]triazolo[4,5-d]pyrimidin-5-ylamine and 4-methylthiazole by the method described for Example 30 to give the title compound (0.105 g, 20%); NMR $\delta_H$(400 MHz, DMSO) 7.77 (1H, t, J 7.9 Hz), 7.72 (1H, s), 7.44 (1H, d, J 7.9 Hz), 7.35 (2H, br s), 7.14 (1H, d, J 7.4 Hz), 5.82 (2H, s), 2.56 (3H, s), 1.84 (2H, m), 1.73 (2H, m), 1.64 (2H, m), 1.40 (3H, m), −0.10 (9H, s); (M+H)$^+$ 481.

7-(4-Methylthiazol-2-yl)-3-{6-[1-hydroxy-1-cyclopentyl]pyridin-2-ylmethyl}-3H-[1,2,3]triazolo[4,5-d]pyrimidin-5-ylamine A solution of 7-(4-methylthiazol-2-yl)-3-{6-[1-trimethylsilyloxy-1-cyclopentyl]pyridin-2-ylmethyl}-3H-[1,2,3]triazolo[4,5-d]pyrimidin-5-ylamine (0.105 g, 0.22 mmol) in THF (6 mL) was treated with tetrabutylammonium fluoride (1.0 M in THF, 0.33 mL, 0.33 mmol), refluxed for 90 min, cooled, concentrated in vacuo and partitioned between water and EtOAc. The aqueous phase was extracted with EtOAc and the combined organic phase dried (MgSO$_4$), concentrated in vacuo, triturated with EtOAc and the resulting solid filtered to give the title compound (0.021 g, 24%) as a pale yellow solid.

NMR $\delta_H$ (400 MHz, DMSO) 1.43-1.51 (2H, m), 1.58-1.62 (2H, m), 1.67-1.73 (2H, m), 1.77-1.83 (2H, m), 2.57 (3H, s), 4.97 (1H, s), 5.82 (2H, s), 7.02 (1H, d, J 7.5 Hz), 7.38 (2H, b), 7.55 (1H, d, J 8.0 Hz), 7.72-7.75 (2H, m); (M+H)$^+$ 409.

Example 28

7-(4-methylthiazol-2-yl)-3-(6-[4-hydroxytetrahydropyran-4-yl]pyrid-2-ylmethyl)-3H-[1,2,3]triazolo[4,5-d]pyrimidin-5-amine This is prepared from 7-chloro-3-(6-[4-hydroxytetrahydropyran-4-yl]pyrid-2-ylmethyl)-3H-[1,2,3]triazolo[4,5-d]pyrimidin-5-amine and 4-methylthiazole by the method of Example 38.

Example 29

7-(4-methylthiazol-2-yl)-3-(6-[1-hydroxycyclobutyl]pyrid-2-ylmethyl)-3H-[1,2,3]triazolo[4,5-d]pyrimidin-5-amine This is prepared from 7-chloro-3-(6-[1-hydroxycyclobutyl]pyrid-2-ylmethyl)-3H-[1,2,3]triazolo[4,5-d]pyrimidin-5-amine and 4-methylthiazole by the method of Example 38.

Example 30

7-(4-methylthiazol-2-yl)-3-(6-[methoxymethyl]pyrid-2-ylmethyl)-3H-[1,2,3]triazolo[4,5-d]pyrimidin-5-amine N-[2-Amino-4-chloro-6-({6-methoxymethyl]pyridin-2-ylmethyl}amino)pyrimidin-5-yl]formamide Prepared from N-(2-amino-4,6-dichloropyrimidin-5-yl) formamide (commercially available) and 6-methoxymethylpyridin-2-methanamine by the method described reference example 1.

7-Chloro-3-(6-methoxymethylpyridin-2-ylmethyl)-3H-[1,2,3]triazolo[4,5-d]pyrimidin-5-ylamine Prepared from N-[2-amino-4-chloro-6-({6-methoxymethyl]pyridin-2-ylmethyl}amino)pyrimidin-5-yl]formamide by the method described in reference example 1 to give the title compound; LC-MS Retention time 1.91 min, (M+H)+ 306.

3-(6-Methoxymethylpyridin-2-ylmethyl)-7-(4-methylthiazol-2-yl)-3H-[1,2,3]triazolo[4,5-d]pyrimidin-5-ylamine A solution of 4-methylthiazole (0.15 mL, 1.65 mmol) in dry THF (7.5 mL) was cooled to −78° C. under nitrogen, treated with n-BuLi (1.0 mL, 1.65 mmol) and stirred for 30 minutes, then ZnCl (1-M, 1.65 mL, 1.65 mmol) was added, and the reaction mixture was warmed to room temperature. 7-Chloro-3-(6-methoxymethylpyridin-2-ylmethyl)-3H-[1,2,3]triazolo[4,5-d]pyrimidin-5-amine (250 mg, 0.825 mmol) was then added followed by Pd(PPh$_3$)$_4$ (48 mg, 0.04 mmol) and the reaction mixture heated to reflux for 1 h. The reaction mixture was cooled to room temperature, quenched with ammonium chloride and extracted with ethyl acetate. The organic phase was washed with water, dried and concentrated in vacuo. The crude product was purified by chromatography (eluant: EtOAc-heptane 1:1 to 2:1) to give the title compound (38 mg, 13%) as a yellow solid.

IR $\nu_{max}$ (DR)/cm$^{-1}$ 3324, 3302, 2921, 1651, 1596, 1519, 1418, 1366, 1257, 1198 and 1112; NMR $\delta_H$ (400 MHz, DMSO) 7.78 (1H, t, J 7.5 Hz), 7.73 (1H, s), 7.43 (2H, br s), 7.34 (1H, d, J 7.5 Hz), 7.04 (1H, d, J 7.0 Hz), 5.78 (2H, s), 4.42 (2H, s), 3.33 (3H, s) and 2.56 (3H, s); LC Retention time 1.01 min (50:80); (M+H)$^+$ 369.

Example 31

7-(5-methylfuran-2-yl)-3-(6-[difluoromethyloxymethyl]-pyrid-2-ylmethyl)-3H-[1,2,3]triazolo[4,5-d]pyrimidin-5-amine Ethyl 6-difluoromethoxymethylpyridine-2-carboxylate 2,2-Difluoro-2-(fluorosulfonyl)acetic acid (495 mL, 4.79 mmol) was added dropwise to a solution of ethyl 6-hydroxymethylpyridine-2-carboxylate (800 mg, 4.79 mmol) and CuI (91 mg, 0.479 mmol) in MeCN (10 mL) at room temperature at a rate to maintain the internal temperature <30° C. The mixture was stirred for a further 20 min at room temperature, poured onto brine/water and extracted with EtOAc (×3). The combined extracts were dried (MgSO$_4$), filtered, evaporated and purified by column chromatography (4:1 to 2:1, isohexane:EtOAc) to give the title compound (130 mg, 13%) as a colorless oil; NMR $\delta_H$ (400 MHz, CDCl$_3$) 8.01 (1H, d, J 7.5 Hz), 7.89 (1H, t, J 7.5 Hz), 7.66 (1H, d, J 7.5 Hz), 6.41 (1H, t, J 74.0 Hz), 5.14 (2H, s), 4.49 (2H, q, J 7.0 Hz), 1.44 (3H, t, J 7.0H); (M+H)$^+$ 232.

6-Difluoromethoxymethylpyridine-2-methanol

NaBH$_4$ (377 mg, 9.96 mmol) was added to a solution of ethyl 6-difluoromethoxymethylpyridine-2-carboxylate (2.30 g, 9.96 mmol) in EtOH (50 mL) at 0° C., the mixture was warmed to 80° C. and stirred for 5 h. The mixture was cooled to 0° C., quenched with sat. aq. NH$_4$Cl, concentrated in vacuo and partitioned between EtOAc and brine. The organic layer was separated, dried (MgSO$_4$), filtered and evaporated to give the title compound (1.50 g, 80%) as a colorless oil; NMR $\delta_H$ (400 MHz, CDCl$_3$) 7.73 (1H, t, J 8.0 Hz), 7.35 (1H, d, J 8.0 Hz), 7.19 (1H, d, J 8.0 Hz), 6.39 (1H, t, J 74.0 Hz), 5.02 (2H, s), 4.76 (2H, s); (M+H)$^+$ 190.

2-Bromomethyl-6-difluoromethoxymethylpyridine

Prepared from 6-difluoromethoxymethylpyridine-2-methanol by the bromination method described in Example 36 to give the title compound (52%); NMR $\delta_H$ (400 MHz, CDCl$_3$) 7.74 (1H, t, J 8.0 Hz), 7.39 (1H, d, J 8.0 Hz), 7.37 (1H, d, J 8.0 Hz), 6.40 (1H, t, J 74.0 Hz), 5.01 (2H, s), 4.53 (2H, s); (M+H)$^+$ 252, 254

3-(6-Difluoromethoxymethylpyridin-2-ylmethyl)-7-(5-methyl-2-furyl)-3H-[1,2,3]triazolo[4,5-d]pyrimidin-5-ylamine Prepared from 7-(5-methyl-2-furyl)-1H[1,2,3]triazolo[4,5-d]pyrimidin-5-ylamine and 2-bromomethyl-6-difluoromethoxymethylpyridine by the alkylation method described in Example 36.

Mp: 194.8-195.1° C.; IR $\nu_{max}$ (DR)/cm$^{-1}$ 3512, 3295, 3172, 1632, 1574, 1499, 1464, 1436 and 1417; NMR $\delta_H$ (400 MHz, DMSO) 7.88 (1H, d, J 3.5 Hz), 7.84 (1H, t, J 8.0 Hz), 7.40 (1H, d, J 8.0 Hz), 7.31 (2H, br s), 7.10 (1H, d, J 8.0 Hz), 6.81 (1H, t, J 75.8 Hz), 6.52 (1H, m), 5.76 (2, s), 4.92 (2H, s), 2.46 (3H, s); (M+H)$^+$ 388; Anal. Calcd for C$_{17}$H$_{15}$N$_7$O$_2$F$_2$: C, 52.17; H, 3.90; N, 25.30. Found: C, 52.69; H, 3.97; N, 25.19.

Example 32

7-(5-methylfuran-2-yl)-3-(6-[2-ethoxyethoxymethyl]pyrid-2-ylmethyl)-3H-[1,2,3]triazolo[4,5-d]pyrimidin-5-amine 3-(6-Bromomethylpyridin-2-ylmethyl)-7-(5-methyl-2-furyl)-3H-[1,2,3]triazolo[4,5-d]pyrimidin-5-ylamine Prepared from 7-(5-methyl-2-furyl)-1H-[1,2,3]triazolo[4,5-d]pyrimidin-5-ylamine and 2,6-bis(bromomethyl)pyridine by the alkylation method described in Example 36; NMR $\delta_H$ (400 MHz, DMSO) 2.46 (3H, s), 4.64 (2H, s), 5.75 (2H, s), 6.50 (1H, d, J 3.5 Hz), 7.04 (1H, d, J 8.0 Hz), 7.31 (2H, s), 7.49 (1H, d, J 7.5 Hz), 7.80 (1H, t, J 7.5 Hz), 7:88 (1H, d, J 3.5 Hz). TLC (Hexane:EtOAc (1:1)) Rf=0.28**

3-(6-Ethoxyethoxymethylpyridin-2-ylmethyl)-7-(5-methyl-2-furyl)-3H-[1,2,3]triazolo[4,5-d]pyrimidin-5-ylamine A solution of 2-ethoxyethanol (242 µl, 2.5 mmol) in anhydrous THF (15 mL) was cooled to 0° C. and treated with NaH (100 mg, 2.5 mmol). The reaction was stirred at 0° C. for 10 mins, then treated with 3-(6-bromomethylpyridin-2-ylmethyl)-7-(5-methyl-2-furyl)-3H-[1,2,3]triazolo[4,5-d]pyrimidin-5-ylamine (100 mg, 0.25 mmol), stirred at room temperature for 30 mins. The reaction was quenched with aqueous NH$_4$Cl and extracted with EtOAc. The combined organic phases were dried (MgSO$_4$) and concentrated in vacuo. The resulting solid was suspended in MeOH (10 mL) and treated with 4M HCl in dioxane (2 mL), the reaction mixture was then diluted with diethyl ether (40 mL) and the resulting solid isolated by filtration to give the product (34 mg, 31%) as a yellow solid.

IR $\nu_{max}$ (DR)/cm$^{-1}$ 3519, 3296, 3177, 2877, 1625, 1574, 1499, 1433, 1322, 1228, 1112, 1023, 958 and 767; NMR $\delta_H$ (400 MHz, DMSO) 1.09 (3H, t, J 7.0 Hz), 2.46 (3H, s), 3.42 (2H, q, J 7.0 Hz), 3.50 (2H, dd, J 5.5 Hz, 3.0 Hz), 3.58 (2H, dd, J 5.5 Hz, 4.0 Hz), 4.51 (2H, s), 5.73 (2H, s), 6.51 (1H, dd, J 3.5 Hz, 1.0 Hz), 7.03 (1H, d, J 7.5 Hz), 7.29 (2H, s), 7.36 (1H, t, J 7.5 Hz), 7.88 (1H, d, J 3.5 Hz).

Example 33

7-(5-methylfuran-2-yl)-3-(6-[tetrahydrofuran-2-ylmethyl]oxymethylpyrid-2-ylmethyl)-3H-[1,2,3]triazolo[4,5-d]pyrimidin-5-amine 2-Bromomethyl-6-(tetrahydrofuran-2-ylmethoxymethyl)pyridine Prepared from 2,6-bis(bromomethyl)pyridine and (RS)-tetrahydrofuran-2-methanol by the alkylation method described for the final step of Example 32 to give the title compound (19%); NMR $\delta_H$ (400 MHz, CDCl$_3$) 7.70 (1H, t, J 7.5 Hz), 7.42 (1H, d, J 7.5 Hz), 7.33 (1H, d, J 7.5 Hz), 4.73-4.65 (2H, m), 4.52 (2H, s), 4.17-4.10 (1H, m), 3.93-3.87 (1H, m), 3.82-3.77 (1H, m), 3.62-3.55 (2H, m), 2.03-1.85 (3H, m), 1.71-1.62 (1H, m); (M+H)$^+$ 286, 288.

(RS)-3-{6-(Tetrahydrofuran-2-ylmethoxymethyl]pyridin-2-ylmethyl}-7-(5-methyl-2-furyl)-3H-[1,2,3]triazolo[4,5-d]pyrimidin-5-ylamine Prepared from 7-(5-methyl-2-furyl)-1H-[1,2,3]triazolo[4,5-d]pyrimidin-5-ylamine and 2-bromomethyl-6-(tetrahydrofuran-2-ylmethoxymethyl)pyridine by the alkylation method described in Example 36.

Mp: 154.2-154.5° C.; IR $v_{max}$ (DR)/cm$^{-1}$ 3334, 3188, 2871, 1738, 1652, 1600 and 1419; NMR $\delta_H$ (400 MHz, DMSO) 7.88 (1H, d, J 3.5 Hz), 7.78 (1H, t, J 8.0 Hz), 7.36 (1H, d, J 8.0 Hz), 7.29 (2H, br s), 7.04 (1H, d, J 8.0 Hz), 6.53-6.51 (1H, m), 5.73 (2H, s), 4.51 2H, s), 3.98-3.93 (1H, m), 3.74-3.68 (1H, m), 3.64-3.58 (1H, m), 3.45-3.43 (2H, m), 2.46 (3H, s), 1.91-1.71 (3H, m), 1.56-1.48 (1H, m); (M+H)$^+$ 422.

Example 34

7-(5-methylfuran-2-yl)-3-(6-[tetrahydrofuran-3-ylmethyl]oxymethylpyrid-2-ylmethyl)-3H-[1,2,3]triazolo[4,5-d]pyrimidin-5-amine

2-Bromomethyl-6-(tetrahydrofuran-3-ylmethyl)pyridine

Prepared from 2,6-bis(bromomethyl)pyridine and (RS)-tetrahydrofuran-3-methanol by the alkylation method described for the final step of Example 32 to give the title compound (37%); NMR $\delta_H$ (400 MHz, CDCl$_3$) 7.70 (1H, t, J 8.0 Hz), 7.37-7.33 (2H, m), 4.63 (2H, s), 4.53 (2H, s), 3.89-3.82 (2H, m), 3.77-3.72 (1H, m), 3.65-3.61 (1H, m), 3.56-3.46 (1H, m), 2.66-2.56 (1H, m), 2.09-1.99 (1H, m), 1.69-1.60 (1H, m); (M+H)$^+$ 286, 288.

(RS)-3-{6-(Tetrahydrofuran-3-ylmethoxymethyl]pyridin-2-ylmethyl}-7-(5-methyl-2-furyl)-3H-[1,2,3]triazolo[4,5-d]pyrimidin-5-ylamine Prepared from 7-(5-methyl-2-furyl)-1H-[1,2,3]triazolo[4,5-d]pyrimidin-5-ylamine and 2-bromomethyl-6-(tetrahydrofuran-3-ylmethoxymethyl)pyridine by the alkylation method described for Example 36.

Mp: 168.7-168.9° C.; IR $v_{max}$ (DR)/cm$^{-1}$ 3514, 3293, 3171, 2935, 2860, 1610, 1575, 1498 and 1434; NMR $\delta_H$ (400 MHz, DMSO) 7.88 (1H, d, J 3.5 Hz), 7.79 (1H, t, J 7.5 Hz), 7.34 (1H, d, J 7.5 Hz), 7.28 (2H, br s), 7.06 (1H, d, J 7.5 Hz), 6.51 (1H, dd, J 3.5, 1.0 Hz), 5.73 (2H, s), 4.49 (2H, s), 3.71-3.55 (3H, m), 3.44-3.33 (3H, m), 2.51-2.41 (1H, m), 2.46 (3H, s), 1.93-1.84 (1H, m), 1.54-1.45 (1H, m); (M-t-H)$^+$ 422.

Example 35

7-(5-methylfuran-2-yl)-3-(6-[2-isopropyloxyethyoxy]oxymethylpyrid-2-ylmethyl)-3H-[1,2,3]triazolo[4,5-d]pyrimidin-5-amine

2-Bromomethyl-6-(isopropyloxyethoxymethyl)pyridine

Prepared from 2,6-bis(bromomethyl)pyridine and 2-(isopropyloxy)ethanol by the alkylation method described for the final step of Example 32 to give the title compound (28%); NMR $\delta_H$ (400 MHz, CDCl$_3$) 7.69 (1H, t, J 7.5 Hz), 7.43 (1H, d, J 7.5 Hz), 7.33 (1H, d, J 7.5 Hz), 4.69 (2H, s), 4.53 (2H, s), 3.73-3.69 (2H, m), 3.68-3.58 (3H, m), 1.18 (6H, d, J 6.0 Hz); (M+H)$^+$ 288, 290.

3-{6-(Isopropyloxyethoxymethyl]pyridin-2-ylmethyl}-7-(5-methyl-2-furyl)-3H-[1,2,3]triazolo[4,5-d]pyrimidin-5-ylamine Prepared from 7-(5-methyl-2-furyl)-1H-[1,2,3]triazolo[4,5-d]pyrimidin-5-ylamine and 2-bromomethyl-6-(isopropyloxyethoxymethyl)pyridine by the alkylation method described in Example 36.

Mp: 127.4-127.6° C.; IR $v_{max}$ (DR)/cm$^{-1}$ 3484, 3326, 3210, 2968, 2869, 1640, 1569, 1541, 1512, 1438 and 1416; NMR $\delta_H$ (400 MHz, DMSO) 7.88 (1H, d, J 3.5 Hz), 7.78 (1H, t, J 7.5 Hz), 7.37 (1H, d, J 7.5 Hz), 7.28 (2H, br s), 7.03 (1H, d, J 7.5 Hz), 6.51 (1H, dd, J 3.5, 1.0 Hz), 5.73 (2H, s), 4.51 (2H, s), 3.58-3.47 (5H, m), 2.46 (3H, s), 1.06 (6H, d, J 6.0 Hz); (M+H)$^+$ 424.

Example 36

7-(5-methylfuran-2-yl)-3-(6-[1-methoxy-1-methylethyl]oxymethylpyrid-2-ylmethyl)-3H-[1,2,3]triazolo[4,5-d]pyrimidin-5-amine

2-Hydroxymethyl-6-(1-hydroxy-1-methylethyl)pyridine

Methylmagnesium bromide (1.0 M in toluene/THF 3:1, 19.7 mL, 27.6 mmol) was added slowly to a stirred solution of methyl 2-(hydroxymethyl)pyridine-2-carboxylate (1.0 g, 5.52 mmol) in THF (15 mL) at 0° C., the mixture was allowed to warm to room temperature and stirred for 16 h. The reaction mixture was quenched with NH$_4$Cl aq, partitioned between EtOAc and sat aq NH$_4$Cl, the organic portion was separated, dried (MgSO$_4$), filtered and evaporated. This residue was purified by column chromatography (1:1, EtOAc:isohexane) to give the title compound (530 mg, 58%) as a colourless oil; NMR $\delta_H$ (400 MHz, CDCl$_3$) 7.72 (1H, t, J 7.5 Hz), 7.32 (1H, d, J 7.5 Hz), 7.19 (1H, d, J 7.5 Hz), 4.79 (2H, s), 4.42 (1H, br s), 3.18 (1H, br s), 1.57 (6H, s); (M+H)$^+$ 168.

2-tert-Butyldimethylsilyloxymethyl-6-(1-hydroxy-1-methylethyl)pyridine

Imidazole (2.27 g, 33.3 mmol) was added to a stirred solution of 2-hydroxymethyl-6-(1-hydroxy-1-methylethyl)pyridine (5.30 g, 31.7 mmol) and tert-butyldimethylsilylchloride (5.02 g, 33.3 mmol) in DMF (70 mL) and the mixture was stirred for 16 h at room temperature. The mixture was poured onto water, extracted with EtOAc, the organic portion was separated, dried (MgSO$_4$), filtered and evaporated to give the title compound (8.19 g, 92%) as a colourless oil; NMR $\delta_H$ (400 MHz, CDCl$_3$) 7.74-7.70 (1H, m), 7.40-7.38 (1H, m), 7.20-7.18 (1H, m), 5.34 (1H, s), 4.83 (2H, s), 1.52 (6H, s), 0.97 (9H, s), 0.13 (6H, s); (M+H)$^+$ 282.

2-tert-Butyldimethylsilyloxymethyl-6-(1-methoxy-1-methylethyl)pyridine

NaH (285 mg, 7.12 mmol) was added portionwise to a stirred solution of 2-tert-butyldimethylsilyloxymethyl-6-(1-hydroxy-1-methylethyl)pyridine (2.0 g, 7.12 mmol) in DMF (30 mL) at room temperature. After 20 min, methyl iodide (1.33 mL, 21.4 mmol) was added, the mixture was warmed to 50° C. and stirred for 16 h at this temperature. The mixture was poured onto water, extracted with EtOAc (×3), the combined extracts were dried (MgSO$_4$), filtered evaporated and the residue purified by column chromatography (20:1 to 10:1, isohexane:EtOAc) to give the title compound (1.20 g, 57%) as a colorless oil; NMR $\delta_H$ (400 MHz, CDCl$_3$) 7.69-7.65 (1H, m), 7.38-7.34 (2H, m), 4.81 (2H, s), 3.15 (3H, s), 1.53 (6H, s), 0.96 (9H, s), 0.12 (6H, s).

2-Hydroxymethyl-6-(1-methoxy-1-methylethyl)pyridine

A solution of 2-tert-butyldimethylsilyloxymethyl-6-(1-methoxy-1-methylethyl)pyridine (1.20 g, 4.08 mmol) in AcOH (45 mL), THF (15 mL) and H$_2$O (15 mL) was stirred for 48 h at room temperature. The solvent was removed in vacuo, the residue was partitioned between DCM and sat aq NaHCO$_3$, the organic portion was separated, dried (MgSO$_4$), filtered and evaporated to give the title compound (740 mg, 100%) as a colourless oil; NMR $\delta_H$ (400 MHz, CDCl$_3$) 7.70-7.66 (1H, m), 7.48-7.45 (1H, m), 7.07-7.04 (1H, m), 4.74 (2H, d, J 5.0 Hz), 4.14 (1H, t, J 5.0 Hz), 3.18 (3H, s), 1.57 (6H, s).

2-Bromomethyl-6-(1-methoxy-1-methylethyl)pyridine

Carbon tetrabromide (1.59 g, 4.80 mmol) was added portionwise to a stirred solution of 2-hydroxymethyl-6-(1-methoxy-1-methylethyl)pyridine (724 mg, 4.00 mmol) and triphenylphosphine (1.15 g, 4.40 mmol) in DCM (50 mL) at 0° C. The mixture was stirred at 0° C. for 1 h then concentrated in vacuo. The residue was purified by column chromatography (20:1 to 5:1 isohexane:EtOAc) to give the title compound (732 mg, 75%) as a colourless oil; NMR $\delta_H$ (400 MHz, CDCl$_3$) 7.69-7.65 (1H, m), 7.46-7.43 (1H, m), 7.32-7.30 (1H, m), 4.55 (2H, s), 3.17 (3H, s), 1.55 (6H, s).

3-{6-(2-Methoxy-2-propyl)pyridin-2-ylmethyl}-7-(5-methyl-2-furyl)-3H-[1,2,3]triazolo[4,5-d]pyrimidin-5-ylamine NaH (100 mg, 2.50 mmol) was added portionwise to a stirred suspension of triazole (538 mg, 2.50 mmol) in DMF (10 mL) at 0° C. After 15 min 2-bromomethyl-6-(1-methoxy-1-methylethyl)pyridine (732 mg, 3.00 mmol) in DMF (3 mL) was added, the mixture was allowed to warm to room temperature and stirred for 16 h. The solvent was removed in vacuo, the residue was taken up in MeOH and evaporated onto silica prior to purification by column chromatography (1:1 to 2:1 EtOAc:isohexane) to give the title compound (280 mg, 30%) as an off-white solid.

Mp: 178.0-178.5° C.; IR $\nu_{max}$ (DR)/cm$^{-1}$ 3469, 3317, 3175, 2982, 2932, 2825, 1648, 1568, 1512 and 1436; NMR $\delta_H$ (400 MHz, DMSO) 7.88 (1H, d, J 3.0 Hz), 7.76 (1H, t, J 7.5 Hz), 7.41 (1H, d, J 7.5 Hz), 7.24 (2H, br s), 7.02 (1H, d, J 7.5 Hz), 6.52-6.50 (1H, m), 5.77 (2H, s), 3.01 (3H, s), 2.46 (3H, s), 1.28 (6H, s); (M+H)$^+$ 380.

Example 37

7-(5-methylfuran-2-yl)-3-(6-[2,2,2-trifluoroethyl] oxymethylpyrid-2-ylmethyl)-3H-[1,2,3]triazolo[4,5-d]pyrimidin-5-amine Prepared from 3-(6-bromomethylpyridin-2-ylmethyl)-7-(5-methyl-2-furyl)-3H-[1,2,3]triazolo[4,5-d]pyrimidin-5-ylamine and trifluoroethanol by the method described in Example 32.

IR $\nu_{max}$ (DR)/cm$^{-1}$ 3282, 3098, 1954, 1649, 1520, 1463, 1282, 1165, 1029 and 761; NMR $\delta_H$ (400 MHz, DMSO) 2.46 (3H, s), 4.14 (2H, q, J 9.0 Hz), 4.68 (2H, s), 5.76 (4H, s), 6.52 (1H, d, J 3.0 Hz), 7.11 (1H, d, J 7.5 Hz), 7.37 (1H, d, J 7.5 Hz), 7.84 (1H, t, J 7.5 Hz), 7.89 (1H, d, J 3.0 Hz).

Example 38

S-7-(thiazol-2-yl)-3-(6-[tetrahydrofuran-3-yl]oxymethylpyrid-2-ylmethyl)-3H-[1,2,3]triazolo[4,5-d]pyrimidin-5-amine A solution of thiazole (0.070 g, 0.822 mmol) in dry THF (8 mL) at −78° C. was treated with n-butyllithium (2.5 M in hexanes, 0.39 mL, 0.987 mmol), stirred for 20 min, treated with a solution of ZnCl$_2$ (0.5-M in THF, 2.47 mL) then warmed to room temperature and stirred for 1 h. The mixture was treated with 7-chloro-3-{6-[(S)-(tetrahydrofuran-3-yl)oxymethyl]pyridin-2-ylmethyl}-3H-[1,2,3]triazolo[4,5-d]pyrimidin-5-ylamine (0.099 g, 0.274 mmol) and tetrakis (triphenylphosphine)palladium(0) (0.016 g, 0.014 mmol), heated at reflux for 5 h, cooled, concentrated in vacuo, and purified by chromatography (SiO$_2$; EtOAc) to give the title compound (0.024 g, 21%) as a solid.

NMR $\delta_H$ (400 MHz, d$_6$-DMSO) 8.28 (1H, d, J 3.0 Hz), 8.17 (1H, d, J 3.0 Hz), 7.79 (1H, t, J 8.0 Hz), 7.50 (2H, br s), 7.35 (1H, d, J 8.0 Hz), 7.08 (1H, d, J 8.0 Hz), 5.78 (2H, s), 4.47 (2H, s), 4.22-4.19 (1H, m), 3.75-3.60 (4H, m) and 1.99-1.88 (2H, m); LC-MS Retention time 1.89 min; (M+H)$^+$ 411.

The following example does not form a part of the invention:

Reference Example 1

7-phenyl-3-(6-[2-oxopyrrolidin-1-yl]pyrid-2-ylmethyl)-3H-[1,2,3]triazolo[4,5-d]pyrimidin-5-amine 6-Bromopyridine-2-methanol A solution of 6-bromopyridine-2-carbaldehyde (10.00 g, 53.76 mmol) in MeOH (120 mL) was treated with sodium borohydride (2.04 g, 53.76 mmol), stirred for 1 h and partitioned between EtOAc and water. The organic phase was separated and the aqueous re-extracted with ethyl acetate. The combined organic extracts were dried (MgSO$_4$) and concentrated in vacuo to give the title compound (9.76 g, 97%) as a pale-yellow liquid; LC-MS retention time 1.52 min, (M+H)$^+$ 188 and 190.

1-(6-Hydroxymethylpyridin-2-yl)pyrrolidin-2-one

A mixture of (6-bromopyridine-2-methanol (9.76 g, 51.9 mmol), copper(I) iodide (0.99 g, 5.19 mmol) N,N'-dimethylethane-1,2-diamine (1.12 mL, 10.38 mmol), 1,4-dioxane (400 mL) and potassium carbonate (14.35 g, 103.84 mmol) was heated at reflux for 8 h, cooled, concentrated in vacuo and partitioned between EtOAc and water. The organic phase was separated, the aqueous phase re-extracted with EtOAc and the combined organic extracts were dried (MgSO$_4$) and concentrated in vacuo to give the title compound (10.19 g, quantitative) as a pale-yellow solid; NMR $\delta_H$ (400 MHz, CDCl$_3$) 8.32 (1H, d, J 8.5 Hz), 7.69 (1H, dd, J 8.5, 7.5 Hz), 6.96 (1H, dd, J 7.5, 1.5 Hz), 4.71 (2H, d, J 5.0 Hz), 4.17-4.13 (2H, m), 3.50 (1H, t, J 5.0 Hz), 2.70-2.66 (2H, m), 2.19-2.11 (2H, m); (M+H)$^+$ 193; LC-MS Retention time 1.46 min.

1-(6-Bromomethylpyridin-2-yl)pyrrolidin-2-one

A stirred solution of 1-(6-hydroxymethylpyridin-2-yl)pyrrolidin-2-one (10.19 g, 53.01 mmol), in dichloromethane (600 mL), was treated with triphenylphosphine (15.29 g, 58.31 mmol) followed by carbon tetrabromide (15.66 g, 58.31 mmol), stirred for 1 h, concentrated in vacuo and purified by column chromatography ($SiO_2$; EtOAc:hexane (1:1)) to give the title compound (10.19 g) as a white solid also containing triphenylphosphine oxide as an impurity; NMR $\delta_H$ (400 MHz, $d_6$-DMSO) inter alia 8.22 (1 H, d, J 8.5 Hz), 7.81 (1 H, t, J 7.5 Hz), 7.28 (1 H, d, J 7.5 Hz), 4.63 (2 H, s), 3.98 (2 H, t, J 7.0 Hz), 2.58 (2 H, t, J 8.0 Hz) and 2.08-2.00 (2 H, m); $(M+H)^+$ 255, 257.

1-(6-Azidomethylpyridin-2-yl)pyrrolidin-2-one

A solution of 1-(6-bromomethylpyridin-2-yl)pyrrolidin-2-one (10.19 g, 39.94 mol) containing triphenylphosphine oxide impurity in DMF (80 mL) was treated with sodium azide (2.60 g, 39.94 mmol), stirred for 18 h and partitioned between EtOAc and water. The organic phase was separated and the aqueous phase re-extracted with EtOAc (×2). The combined organic extracts were dried ($MgSO_4$) and concentrated in vacuo to give the title compound as a yellow oil, contaminated with triphenylphosphine oxide; used in the next step without further purification; LC-MS retention time 2.19 min, $(M+H)^+$ 218.

1-(6-Aminomethylpyridin-2-yl)pyrrolidin-2-one

A solution of crude 1-(6-azidomethyl-pyridin-2-yl)pyrrolidin-2-one (containing triphenylphosphine oxide), in ethanol (100 mL) was treated with platinum (5% on carbon), stirred under hydrogen at 45° C. and ambient pressure for 18 h, filtered through a pad of Celite, concentrated in vacuo then co-evaporated with toluene and then chloroform to give the title compound (11.32 g) as a white solid, contaminated with triphenylphosphine oxide; LC-MS retention time 0.66 min, $(M+H)^+$ 192.

N-(2-Amino-4-chloro-6-{[6-(2-oxopyrrolidin-1-yl)pyridin-2-ylmethyl]amino}pyrimidin-5-yl)formamide A mixture of N-(2-amino-4,6-dichloropyrimidin-5-yl)formamide (3.61 g, 17.43 mmol) and 1-(6-aminomethylpyridin-2-yl)pyrrolidin-2-one (containing triphenylphosphine oxide) (10.00 g, ca. 50 mmol) and triethylamine (4.86 mL, 34.86 mmol) in propan-2-ol (100 mL) was heated at reflux for 18 h, cooled and the resulting precipitate filtered to give the title compound (3.41 g) as an off-white solid; NMR $\delta_H$ (400 MHz, $d_6$-DMSO) 9.21 (1 H, s), 8.20 (1 H, d, J 1 Hz), 8.12 (1 H, d, J 8.5 Hz), 7.73 (1 H, t, J 7.5 Hz), 7.38 (1 H, t, J 6 Hz), 7.02 (1 H, d, J 7.5 Hz), 6.45 (2 H, br s), 4.53 (2 H, d, J 6.0 Hz), 4.00-3.95 (2 H, m), 2.57 (2 H, t, 8.0 Hz) and 2.08-2.00 (2 H, m).

1-{6-[(2,5-diamino-6-chloro-pyrimidin-4-ylamino)methyl]pyridin-2-yl}pyrrolidin-2-one A mixture of as N-(2-amino-4-chloro-6-{[6-(2-oxo-pyrrolidin-1-yl)pyridin-2-ylmethyl]amino}pyrimidin-5-yl)formamide (3.41 g, 9.43 mmol) in ethanol (36 mL) was treated with hydrochloric acid (6-M, 8 mL), heated at reflux for 2 h, cooled and the pH adjusted to 13 with aqueous sodium hydroxide (5-M). The mixture was extracted with EtOAc (×3) and the combined organic extracts were dried ($Na_2SO_4$) and concentrated in vacuo to give the title compound (2.12 g, 68%) as a coral pink solid; LC-MS retention time 1.64 min; $(M+H)^+$ 334.

1-[6-(5-Amino-7-chloro[1,2,3]triazolo[4,5-d]pyrimidin-3-ylmethyl)-pyridin-2-yl]-pyrrolidin-2-one A suspension of 1-{6-[(2,5-diamino-6-chloro-pyrimidin-4-ylamino)methyl]pyridin-2-yl}pyrrolidin-2-one (2.10 g, 6.29 mmol) in glacial acetic acid (6 mL) and EtOH (24 mL) at 0° C. was treated with a solution of sodium nitrite (0.564 g, 8.17 mmol) in water (1.5 mL), stirred for 2 h, warmed to room temperature and the resulting precipitate filtered and dried to give the title compound (1.67 g, 77%) as an off-white solid; LC-MS retention time 1.99 min, $(M+H)^+$ 345.

1-[6-(5-Amino-7-phenyl[1,2,3]triazolo[4,5-d]pyrimidin-3-ylmethyl)pyridin-2-yl]pyrrolidin-2-one A mixture of 1-[6-(5-amino-7-chloro[1,2,3]triazolo[4,5-d]pyrimidin-3-ylmethyl)pyridin-2-yl]pyrrolidin-2-one (0.50 g, 1.45 mmol) and phenylboronic acid (0.354 g, 2.90 mmol) in saturated aqueous sodium hydrogen carbonate (5 mL) and 1,4-dioxane (20 mL) was degassed with a stream of nitrogen for 10 min then treated with tetrakis(triphenylphosphine)palladium(0) (0.083 g, 0.0725 mmol), refluxed for 2 h then partitioned between EtOAc and water. The organic phase was separated and the aqueous phase re-extracted with EtOAc (×2). The combined organic extracts were dried ($MgSO_4$), concentrated in vacuo to give a yellow solid (1.00 g) which was purified by column chromatography [$SiO_2$; EtOAc-hexane (1:1) then EtOAc]. The resulting yellow solid (0.68 g) was triturated with diethyl ether to give the title compound (0.38 g, 68%) as an off-white solid.

NMR $\delta_H$ (400 MHz, $d_6$-DMSO) 8.77-8.74 (2H, m), 8.19 (1H, d, J 8.5 Hz), 7.79 (1H, t, J 7.5 Hz), 7.66-7.65 (2H, m), 7.32 (2H, br s), 6.96 (1H, d, J 7.5 Hz), 5.77 (2H, s), 3.67 (2H, t, J 7 Hz) and 1.99-1.89 (2H, m); LC-MS Retention time 2.32 min; $(M+H)^+$ 387.

Biological Methods
Adenosine Receptor Binding: Binding Affinities at $hA_1$ Receptors The compounds were examined in an assay measuring in vitro binding to human adenosine $A_1$ receptors by determining the displacement of the adenosine $A_1$ receptor selective radioligand 8-Cyclopentyl-1,3-dipropylxanthine ([$^3$H]DPCPX) using standard techniques. See, for example, Lohse M J, et al., (1987), 8-Cyclopentyl-1,3-dipropylxanthine (DPCPX)—a selective high affinity antagonist radioligand for A1 adenosine receptors. *Naunyn Schmiedebergs Arch Pharmacol.*, 336(2):204-10, which is incorporated by reference in its entirety.

Frozen CHO-K1 cells (transfected with a human adenosine $A_1$ recepter expression vector) were homogenized in 130 mL of 50 mM Tris HCl buffer (pH 7.5) containing 10 mM $MgCl_2$, and 0.1 IU/mL adenosine deaminase per pellet using a Ultra-Turrax homogeniser. The resultant homogenate was kept for immediate use in the binding.

Binding assays were performed in a total volume of 250 μL, containing [$^3$H]-DPCPX (3.0 nM), membranes and additional drugs. Total binding was determined using drug dilution buffer (50 mM Tris-HCl pH: 7.5, 10 mM $MgCl_2$, 5% DMSO). Non-specific binding was determined using 300 μM N6-cyclohexyladenosine (CHA). Following incubation for 90 minutes at 21° C., assays were terminated by rapid filtration with GF/B filters (presoaked in 0.1% (w/v) polyethylenimine) using a Canberra Packard filtermate 196, washed 3 times with ice-cold Tris-HCl (pH 7.4). Filters were left to dry overnight, and Microscint-0 scintillation fluid was then added to the filters. The filters were then left for at least 2 hours before the radioactivity was assessed using a Canberra Packard TopCount microplate scintillation counter.

To determine the free ligand concentration, three vials were counted with 25 μL of [$^3$H]DPCPX containing 4 mL of Ultima-Gold MV scintillant on a Beckman LS6500 multi-purpose scintillation counter.

Data was analysed using a 4 parameter logistical equation and non-linear regression which yields affinity constants (pIC$_{50}$), and slope parameters:

$$E = NSB + \frac{Total - NSB}{1 + \left(\frac{\log[IC_{50}]}{\log[A]}\right)^{slope}}$$

where E is the quantity of binding and [A] is the competitor concentration. The K$_i$ is then determined using the Cheng-Prusoff equation:

$$K_i = \frac{IC_{50}}{1 + \left(\frac{[L]}{[K_D]}\right)}$$

Adenosine Receptor Binding: Binding Affinities at hA$_{2A}$ Receptors

The compounds were examined in an assay measuring in vitro binding to human adenosine A$_{2A}$ receptors by determining the displacement of the adenosine A$_{2A}$ receptor selective radioligand 4-[2-[[6-Amino-9-(N-ethyl-β-D-ribo-furanuronamidosyl)-9H-purin-2-yl]amino]ethyl]benzenepropanoic acid hydrochloride ([$^3$H]CGS-21680) using standard techniques. See, for example, Jarvis et al., *J Pharmacol Exp Ther.*, 251(3):888-93, which is incorporated by reference in its entirety.

Frozen HEK-293 cells were homogenized in 65 mL of 50 mM Tris HCl buffer (pH 7.5) containing 10 mM MgCl$_2$, and 0.1 IU/mL adenosine deaminase per pellet using a Ultra-Turrax homogenizer. The resultant homogenate was kept for immediate use in the binding assay. Binding assays were performed in a total volume of 250 μL, containing [$^3$H]-CGS21680 (20.0 nM), membranes and additional drugs. Total binding was determined using drug dilution buffer (50 mM Tris-HCl pH 7.5, 10 mM MgCl$_2$, 5% DMSO). Non-specific binding was determined using 300 μM CHA. Following incubation for 90 minutes at 21° C., assays were terminated by rapid filtration with GF/B filters (presoaked in 0.1% (w/v) polyethylenimine) using a Canberra Packard filtermate 196, washed 3 times with ice-cold Tris-HCl (pH 7.4). Filters were left to dry overnight, and Microscint-0 scintillation fluid was then added to the filters. The filters were then left for at least 2 hours before the radioactivity was assessed using a Canberra Packard TopCount microplate scintillation counter.

To determine the free ligand concentration, three vials were counted with 25 μL of [$^3$H]CGS21680 containing 4 mL of Ultima-Gold MV scintillant on a Beckman LS6500 multi-purpose scintillation counter.

Data was analysed using a 4 parameter logistical equation and non-linear regression which yields affinity constants (pIC$_{50}$), and slope parameters:

$$E = NSB + \frac{Total - NSB}{1 + \left(\frac{\log[IC_{50}]}{\log[A]}\right)^{slope}}$$

where E is the quantity of binding and [A] is the competitor concentration. The K$_i$ is then determined using the Cheng-Prusoff equation:

$$K_i = \frac{IC_{50}}{1 + \left(\frac{[L]}{[K_D]}\right)}$$

Adenosine Receptor Binding: Binding Affinities at hA$_{2B}$ Receptors

The compounds were examined in an assay measuring in vitro binding to human adenosine A$_3$ receptors by determining the displacement of the adenosine A$_{2B}$ receptor radioligand 4-(2-[7-Amino-2-(2-furyl)[1,2,4]triazolo[2,3-a][1,3,5]triazin-5-ylamino]ethyl)phenol ([$^3$H]-ZM241385) using standard techniques. See, for example, Ji and Jacobson., *Drug Design and Discovery.*, 16:217-226, which is incorporated by reference in its entirety.

Frozen HEK-293 cells were homogenized in 65 mL of 50 mM Tris HCl buffer (pH 7.5) containing 10 mM MgCl$_2$, 10 mM EDTA, 0.1 mM Benzamidine and 0.1 IU/mL adenosine deaminase per pellet using a Ultra-Turrax homogenizer. The resultant homogenate was kept for immediate use in the binding assay.

Binding assays were performed in a total volume of 250 μL, containing [$^3$H]-ZM 241385 (20 nM), membranes and additional drugs. Total binding was determined using drug dilution buffer (50 mM Tris-HCl pH 7.5, 10 mM MgCl$_2$, 5% DMSO). Non-specific binding was determined using 10 μM ZM 241385. Following incubation for 60 minutes at 21° C., assays were terminated by rapid filtration with GF/B filters (presoaked in 0.1% (w/v) polyethylenimine) using a Canberra Packard filtermate 196, washed 3 times with ice-cold Tris-HCl (pH 7:4). Filters were left to dry overnight, and Microscint-0 scintillation fluid was then added to the filters. The filters were then left for at least 2 hours before the radioactivity was assessed using a Canberra Packard Top-Count microplate scintillation counter.

To determine the free ligand concentration, three vials were counted with 25 μL of [$^3$H]-ZM 241385 containing 4 mL of Ultima-Gold MV scintillant on a Beckman LS6500 multi-purpose scintillation counter.

Data was analysed using a 4 parameter logistical equation and non-linear regression which yields affinity constants (pIC$_{50}$), and slope parameters:

$$E = NSB + \frac{Total - NSB}{1 + \left(\frac{\log[IC_{50}]}{\log[A]}\right)^{slope}}$$

where E is the quantity of binding and [A] is the competitor concentration. The K$_i$ is then determined using the Cheng-Prusoff equation $$K_i = \frac{IC_{50}}{1 + \left(\frac{[L]}{[K_D]}\right)}$$

Adenosine Receptor Binding: Binding Affinities at hA$_3$ Receptors

The compounds were examined in an assay measuring in vitro binding to human adenosine A$_3$ receptors by determining the displacement of the adenosine A$_3$ receptor selective radioligand 4-aminobenzyl-5'-N-methylcarboxamidoadenosine ([$^{125}$I]-AB MECA) using standard techniques. See, for example, Olah et al., Mol Pharmacol., 45(5):978-82, which is incorporated by reference in its entirety.

Frozen CHO-K1 cells were homogenized in 45 mL of 50 mM Tris HCl buffer (pH 7.5) containing 10 mM MgCl$_2$, 1 mM EDTA and 0.1 IU/mL adenosine deaminase per pellet using a Ultra-Turrax homogenizer. The resultant homogenate was kept for immediate use in the binding assay. Binding assays were performed in a total volume of 250 µL, containing [$^{125}$I]-AB MECA (0.04-0.08 nM), membranes and additional drugs. Total binding was determined using drug dilution buffer (50 mM Tris-HCl pH 7.5, 10 mM MgCl$_2$, 5% DMSO). Non-specific binding was determined using 10 µM IB-MECA. Following incubation for 60 minutes at 21° C., assays were terminated by rapid filtration with GF/B filters (presoaked in 0.1% (w/v) polyethylenimine) using a Canberra Packard filtermate 196, washed 3 times with ice-cold Tris-HCl (pH 7.4). Filters were left to dry overnight, and Microscint-0 scintillation fluid was then added to the filters. The filters were then left for at least 2 hours before the radioactivity was assessed using a Canberra Packard TopCount microplate scintillation counter.

To determine the free ligand concentration, three vials were counted with 25 µL of [$^{125}$I]-AB MECA containing 4 mL of Ultima-Gold MV scintillant on a Beckman LS6500 multi-purpose scintillation counter.

Data was analysed using a 4 parameter logistical equation and non-linear regression which yields affinity constants (pIC$_{50}$), and slope parameters:

$$E = NSB + \frac{Total - NSB}{1 + \left(\frac{\log[IC_{50}]}{\log[A]}\right)^{slope}}$$

where E is the quantity of binding and [A] is the competitor concentration. The K$_i$ is then determined using the Cheng-Prusoff equation:

$$K_i = \frac{IC_{50}}{1 + \left(\frac{[L]}{[K_D]}\right)}$$

Using the assays described above, binding data were collected for a number of the exemplified compounds of the present invention. These data are shown in Table 1, below.

TABLE 1

| Example no. | Binding Affinity | | | | Binding Selectivity | | |
|---|---|---|---|---|---|---|---|
| | hA1- Ki | hA2A- Ki | hA2B- Ki | hA3- Ki | A1/A2a | A2b/A2a | A3/A2a |
| 1 (S isomer) | 192 | 3.4 | 3975 | 2498 | 56 | 1157 | 727 |
| 1 (R isomer) | 143 | 3.4 | 5513 | 2516 | 42 | 1605 | 733 |
| 2 | 360.3 | 1.9 | 2192.3 | 706.3 | 192 | 1165 | 375 |
| 3 | 366.2 | 1.6 | 976.2 | 754.1 | 226 | 602 | 465 |
| 4 | 196.5 | 3.1 | 1134.3 | 1635.1 | 63 | 366 | 528 |
| 5 | 852.6 | 4.3 | 4199.7 | 8521.5 | 199 | 980 | 1989 |
| 6 | 354.1 | 1.1 | 1373.4 | 1498.2 | 313 | 1216 | 1326 |
| 7 | 731.2 | 13.4 | 1244.7 | 8522.8 | 54 | 93 | 634 |
| 8 | 214.3 | 4.8 | 1299.2 | 3762.2 | 44 | 269 | 780 |
| 9 | 706.1 | 9.8 | 3405.9 | NT | 72 | 347 | NT |
| 11 | 319.9 | 5.2 | 3265.6 | 4304.6 | 62 | 634 | 836 |
| 12 | 270.2 | 2.8 | 1000.3 | 8173.7 | 96 | 354 | 2893 |
| 14 | 498.4 | 6.0 | 437.1 | 612.9 | 83 | 73 | 102 |
| 17 | 385.7 | 9.9 | 4688.7 | 1947.4 | 39 | 472 | 196 |
| 20 | 731.2 | 13.4 | 1244.7 | 8522.8 | 54 | 93 | 634 |
| 21 | 2389.1 | 23.9 | 2047.7 | NT | 100 | 86 | NT |
| 23 | 1333.3 | 14.8 | 6821.6 | NT | 90 | 462 | NT |
| 27 | 1729.3 | 11.3 | 5741.2 | 7523.2 | 154 | 510 | 668 |
| 30 | 798.6 | 4.8 | 2373.4 | 4599.9 | 168 | 498 | 965 |
| 32 | 333.7 | 4.6 | 2022.4 | 2495.9 | 73 | 442 | 545 |
| 33 | 298.9 | 7.2 | 1975.7 | 2178.5 | 42 | 274 | 303 |
| 34 | 164.4 | 4.1 | 1893.9 | 2123.5 | 40 | 457 | 513 |
| 35 | 357.2 | 4.5 | 3452.9 | 2396.4 | 79 | 761 | 528 |
| 36 | 421.6 | 4.5 | NT | 939.3 | 93 | NT | 208 |
| 37 | 231.2 | 4.4 | 2383.9 | 2489.3 | 52 | 536 | 560 |
| 38 | 2089.3 | 28.4 | 2979.8 | NT | 73 | 105 | NT |

NT = not tested.

For comparative purposes, several known adenosine A$_{2A}$ antagonists that are described in International Patent Application Publication WO 02/055083 were also tested. The results obtained are shown in Table 2, below.

TABLE 2

| WO 02/055083 Example no. | Binding Affinity | | | | Binding Selectivity | | |
|---|---|---|---|---|---|---|---|
| | hA1- Ki | hA2A- Ki | hA2B- Ki | hA3- Ki | A1/A2a | A2b/A2a | A3/A2a |
| 151 | 101.5 | 5.3 | 276.3 | 830.8 | 19 | 52 | 156 |
| 183 | 84.1 | 1.3 | 231.0 | 655.6 | 67 | 183 | 519 |
| 213 | 584.5 | 2.7 | 270.7 | 1695.3 | 216 | 100 | 625 |
| 217 | 153.1 | 2.9 | 381.7 | 475.5 | 53 | 131 | 163 |
| 247 | 276.0 | 3.0 | 453.8 | 1461.2 | 92 | 151 | 487 |

Example 151=3-(3-aminobenzyl)-7-phenyl-3H-[1,2,3]triazolo[4,5-d]pyrimidine-5-amine Example 183=3-(6-methoxymethyl-2-pyridylmethyl)-7-(5-methyl-2-furyl)-3H-[1,2,3]triazolo[4,5-d]pyrimidine-5-amine Example 213=7-(2-furyl)-3-(6-hydroxymethyl-2-pyridylmethyl)-3H-[1,2,3]triazolo[4,5-d]pyrimidine-5-amine hydrochloride Example 217=7-(2-furyl)-3-(6-isobutyloxymethyl-2-pyridylmethyl)-3H-[1,2,3]triazolo[4,5-d]pyrimidine-5-amine Example 247=7-(2-furyl)-3-(6-isopropoxymethyl-2-pyridylmethyl)-3-[1,2,3]triazolo[4,5-d]pyrimidine-5-amine Evaluation of Potential Anti-Parkinsonian Activity In Vivo: Haloperidol-Induced Hypolocomotion Model It has previously been demonstrated that adenosine antagonists, such as theophylline, can reverse the behavioral depressant effects of dopamine antagonists, such as haloperidol, in rodents (see, for example, Mandhane S. N. et al., Adenosine $A_2$ receptors modulate haloperidol-induced catalepsy in rats. *Eur. J. Pharmacol.* 1997, 328, 135-141, which is incorporated by reference in its entirety). This approach is also considered a valid method for screening drugs with potential antiparkinsonian effects. Thus, the ability of novel adenosine antagonists to block haloperidol-induced deficits in locomotor activity in mice can be used to assess both in vivo and potential antiparkinsonian efficacy.

Female TO mice (25-30 g) are used for all experiments. Animals are housed in groups of 8 (cage size-40 cm (width) by 40 cm (length) by 20 cm (height)) under 12 hour light/dark cycle (lights on 08:00), in a temperature (20±2° C.) and humidity (55±15%) controlled environment. Animals have free access to food and water, and are allowed at least 7 days to acclimatize after delivery before experimental use.

Liquid injectable haloperidol (e.g., 1 mL Serenance ampoules from Baker Norton, Harlow, Essex, each containing haloperidol BP 5 mg) are diluted to a final concentration of 0.02 mg/mL using saline. Test compounds are typically prepared as aqueous suspensions in 8% Tween. All compounds are administered intraperitoneally in a volume of 10 mL/kg.

1.5 hours before testing, mice are administered 0.2 mg/kg haloperidol, a dose that reduces baseline locomotor activity by at least 50%. Test substances are typically administered 5-60 minutes prior to testing. The animals are then placed individually into clean, clear polycarbonate cages (20 cm (width) by 40 cm (length) by 20 cm (height), with a flat perforated, Perspex lid). Horizontal locomotor activity is determined by placing the cages within a frame containing a 3 by 6 array of photocells linked to a computer, which tabulates beam breaks. Mice are left undisturbed to explore for 1 hour, and the number of beams breaks made during this period serves as a record of locomotor activity which is compared with data for control animals for statistically significant differences.

A number of the exemplified compounds of the present invention were tested in this assay and the results obtained are shown in Table 3, below.

TABLE 3

| Example no. | In Vivo activity HaloLMA MED (mg/kg) |
| --- | --- |
| 1 | 0.3 |
| 2 | 1 |
| 3 | 1 |

TABLE 3-continued

| Example no. | In Vivo activity HaloLMA MED (mg/kg) |
| --- | --- |
| 4 | 3 |
| 5 | 3 |
| 6 | 1 |
| 8 | 3 |
| 9 | 10 |
| 12 | 10 |
| 14 | 30 |
| 18 | <30 |
| 20 | 3 |
| 24 | 10 |
| 25 | 3 |
| 27 | 10 |
| 30 | 3 |
| 31 | 1 |
| 32 | 1 |
| 33 | 3 |
| 34 | 1 |
| 36 | 1-3 |
| 37 | 1 |
| 38 | 10 |

Evaluation of Potential Anti-Parkinsonian Activity In Vivo: 6-OHDA Model

Parkinson's disease is a progressive neurodegenerative disorder characterized by symptoms of muscle rigidity, tremor, paucity of movement (hypokinesia), and postural instability. It has been established for some time that the primary deficit in PD is a loss of dopaminergic neurons in the substantia nigra which project to the striatum, and indeed a substantial proportion of striatal dopamine is lost (ca 80-85%) before symptoms are observed. The loss of striatal dopamine results in abnormal activity of the basal ganglia, a series of nuclei which regulate smooth and well coordinated movement (see, e.g., Blandini F. et al., Glutamate and Parkinson's Disease. *Mol. Neurobiol.* 1996, 12, 73-94, which is incorporated by reference in its entirety). The neurochemical deficits seen in Parkinson's disease can be reproduced by local injection of the dopaminergic neurotoxin 6-hydroxydopamine into brain regions containing either the cell bodies or axonal fibers of the nigrostriatal neurons.

By unilaterally lesioning the nigrostriatal pathway on only one-side of the brain, a behavioral asymmetry in movement inhibition is observed. Although unilaterally-lesioned animals are still mobile and capable of self maintenance, the remaining dopamine-sensitive neurons on the lesioned side become supersenstive to stimulation. This is demonstrated by the observation that following systemic administration of dopamine agonists, such as apomorphine, animals show a pronounced rotation in a direction contralateral to the side of lesioning. The ability of compounds to induce contralateral rotations in 6-OHDA lesioned rats has proven to be a sensitive model to predict drug efficacy in the treatment of Parkinson's Disease.

Male Sprague-Dawley rats, obtained from Charles River, are used for all experiments. Animals are housed in groups of 5 under 12 hour light/dark cycle (lights on 08:00), in a temperature (20±2° C.) and humidity (55±5%) controlled environment. Animals have free access to food and water, and are allowed at least 7 days to acclimatize after delivery before experimental use.

Ascorbic acid, desipramine, 6-OHDA and apomorphine are obtained commercially. 6-OHDA is freshly prepared as a solution in 0.2% ascorbate at a concentration of 4 mg/mL prior to surgery. Desipramine is dissolved in warm saline, and administered in a volume of 1 mL/kg. Apomorphine is dissolved in 0.02% ascorbate and administered in a volume of 2 mL/kg. Test compounds are suspended in 8% Tween and injected in a volume of 2 mL/kg.

15 minutes prior to surgery, animals are given an intraperitoneal injection of the noradrenergic uptake inhibitor desipramine (25 mg/kg) to prevent damage to nondopamine neurons. Animals are then placed in an anaesthetic chamber, and anaesthetised using a mixture of oxygen and isoflurane. Once unconscious, the animals are transferred to a stereotaxic frame, where anaesthesia is maintained through a mask. The top of the animal's head is shaved and sterilized using an iodine solution. Once dry, a 2 cm long incision is made along the midline of the scalp and the skin retracted and clipped back to expose the skull. A small hole is then drilled through the skill above the injection site. In order to lesion the nigrostriatal pathway, the injection cannula is slowly lowered to position above the right medial forebrain bundle at −3.2 mm anterior posterior, −1.5 mm medial lateral from bregma, and to a depth of 7.2 mm below the duramater. 2 minutes after lowing the cannula, 2 VAL of 6-OHDA is infused at a rate of 0.5 μL/min over 4 minutes, yielding a final dose of 8 μg. The cannula is then left in place for a further 5 minutes to facilitate diffusion before being slowly withdrawn. The skin is then sutured shut using Ethicon W501 Mersilk, and the animal removed from the strereotaxic frame and returned to its homecage. The rats are allowed 2 weeks to recover from surgery before behavioral testing.

Rotational behavior is measured using an eight station rotameter system, such as one sold by Med Associates, San Diego, USA. Each station is comprised of a stainless steel bowl (45 cm diameter by 15 cm high) enclosed in a transparent Plexiglas cover running around the edge of the bowl, and extending to a height of 29 cm. To assess rotation, rats are placed in cloth jacket attached to a spring tether connected to optical rotameter positioned above the bowl, which assesses movement to the left or right either as partial (45°) or full (360°) rotations. All eight stations are interfaced to a computer that tabulated data.

To reduce stress during drug testing, rats are initially habituated to the apparatus for 15 minutes on four consecutive days. On the test day, rats are given an intraperitoneal injection of test compound 30 minutes prior to testing. Immediately prior to testing, animals are given a subcutaneous injection of a subthreshold dose of apomorphine, then placed in the harness and the number of rotations recorded for one hour. The total number of full contralatral rotations during the hour test period serves as an index of antiparkinsonian drug efficacy.

The invention claimed is:
1. A compound of formula

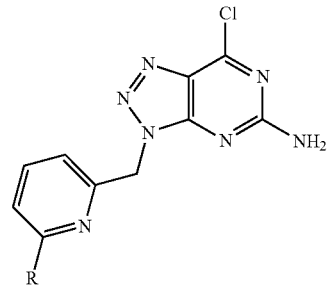

or a tautomer, stereoisomer, or pharmaceutically acceptable salt thereof, wherein
R is —(CR$^a$R$^b$)—O—R$^2$;
R$^a$ is H or alkyl;
R$^b$ is H or alkyl; or R$^a$ and R$^b$ together with the atom to which they are attached form a 3 to 8 membered saturated or partially saturated hydrocarbon ring or form a 4 to 8 membered saturated or partially saturated heterocylic ring comprising a ring member selected from O, N(R$^3$) and S;
R$^2$ is H, alkyl, cycloalkyl or heterocycloalkyl, wherein said alkyl or cycloalkyl may optionally be substituted with halo, alkoxy or heterocycloalkyl;
R$^3$ is H or alkyl;
wherein
heteroaryl is a 5 or 6 membered aromatic ring, comprising one or two ring members selected from N, N(R$^4$), S and O;
alkyl (or the alkyl group of the alkoxy group) is a linear or branched saturated hydrocarbon containing up to 10 carbon atoms;
heterocycloalkyl is a C-linked or N-linked 3 to 10 membered non-aromatic, monocyclic ring, wherein said heterocycloalkyl ring comprises 1, 2 or 3 ring members independently selected from N, N(R$^4$), S(O)$_q$ and O;
R$^4$ is H or alkyl; and
q is 0, 1 or 2.
2. The compound of claim 1, wherein
R$^a$ and R$^b$ are independently H; and
R$^2$ is tetrahydrofuranyl.
3. The compound of claim 1, wherein R$^a$ and R$^b$ are independently H.
4. The compound of claim 1, wherein R is

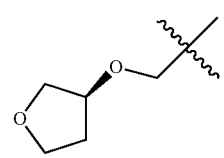

* * * * *